(12) United States Patent
Poznansky et al.

(10) Patent No.: US 9,789,171 B2
(45) Date of Patent: *Oct. 17, 2017

(54) ANTI-FUGETACTIC AGENTS FOR THE TREATMENT OF OVARIAN CANCER

(75) Inventors: Mark C. Poznansky, Charlestown, MA (US); John T. Potts, Jr., West Newton, MA (US); Fabrizio Vianello, Padua (IT); Natalia Papeta, Brookline, MA (US)

(73) Assignee: THE GENERAL HOSPITAL CORPORATION, Boston, MA (US)

( * ) Notice: Subject to any disclaimer, the term of this patent is extended or adjusted under 35 U.S.C. 154(b) by 1360 days.

This patent is subject to a terminal disclaimer.

(21) Appl. No.: 11/667,410

(22) PCT Filed: Nov. 4, 2005

(86) PCT No.: PCT/US2005/040218
§ 371 (c)(1),
(2), (4) Date: Apr. 11, 2008

(87) PCT Pub. No.: WO2006/137934
PCT Pub. Date: Dec. 28, 2006

(65) Prior Publication Data
US 2008/0300165 A1 Dec. 4, 2008

Related U.S. Application Data

(60) Provisional application No. 60/625,733, filed on Nov. 5, 2004.

(51) Int. Cl.
| | | |
|---|---|---|
| *A01N 43/00* | (2006.01) |
| *A61K 31/33* | (2006.01) |
| *A61K 39/00* | (2006.01) |
| *A61K 38/19* | (2006.01) |
| *C07K 16/28* | (2006.01) |
| *A61K 31/00* | (2006.01) |
| *A61K 31/337* | (2006.01) |
| *A61K 31/395* | (2006.01) |
| *A61K 33/24* | (2006.01) |

(52) U.S. Cl.
CPC .......... *A61K 39/0011* (2013.01); *A61K 31/00* (2013.01); *A61K 31/33* (2013.01); *A61K 31/337* (2013.01); *A61K 31/395* (2013.01); *A61K 33/24* (2013.01); *A61K 38/19* (2013.01); *C07K 16/2866* (2013.01); *G01N 2333/726* (2013.01); *G01N 2500/02* (2013.01)

(58) Field of Classification Search
CPC .... A61K 31/00; A61K 38/19; C07K 16/2866; G01N 2333/726; G01N 2500/02
See application file for complete search history.

(56) References Cited

U.S. PATENT DOCUMENTS

| | | |
|---|---|---|
| 4,737,413 A | 4/1988 | Buchanan |
| 5,510,418 A | 4/1996 | Rhee et al. |
| 5,514,555 A | 5/1996 | Springer et al. |
| 5,573,934 A | 11/1996 | Hubbell et al. |
| 5,621,671 A | 4/1997 | Bodnar |
| 5,756,084 A | 5/1998 | Honjo et al. |
| 5,760,084 A | 6/1998 | Swan et al. |
| 5,919,776 A | 7/1999 | Hagman et al. |
| 5,994,298 A | 11/1999 | Tsai et al. |
| 6,238,874 B1 | 5/2001 | Jarnagin et al. |
| 6,399,569 B1 | 6/2002 | Cohen et al. |
| 6,448,054 B1 * | 9/2002 | Poznansky ........... C07K 14/521 424/184.1 |
| 6,987,102 B2 | 1/2006 | Bridger et al. |
| 7,141,363 B2 | 11/2006 | Poznansky et al. |
| 7,775,469 B2 | 8/2010 | Poznansky et al. |
| RE42,152 E | 2/2011 | Bridger et al. |
| 7,897,590 B2 | 3/2011 | Bridger et al. |
| 2002/0098187 A1 | 7/2002 | Ferrara et al. |
| 2002/0131953 A1 | 9/2002 | Takashima et al. |
| 2003/0017141 A1 * | 1/2003 | Poznansky ........... C07K 14/521 424/93.7 |

FOREIGN PATENT DOCUMENTS

| | | |
|---|---|---|
| FR | 2706771 | 12/1994 |
| GB | 2151924 | 7/1985 |
| WO | WO 95/07985 | 3/1995 |
| WO | WO 98/09642 | 3/1998 |
| WO | WO 98/44021 | 10/1998 |
| WO | WO 00/09678 | 2/2000 |
| WO | WO 00/59941 | 10/2000 |
| WO | WO 03011277 A2 * | 2/2003 |

OTHER PUBLICATIONS

Devine et al "Rapid mobilization of CD34+ cells following administration of the CXCR4 antagonist AMD3100 to patients with myeloma and Non-Hodgkin's lymphoma", Journal of Clinical oncology, vol. 22, No. 6, Mar. 15, 2004.*
Hendrix et al "Pharmacokinetics and Safety and AMD-3100, a novel antagonist of the CXCR-4 chemokine receptor, in human volunteers", Antimicrobial agents and chemotherapy, Jun. 2000, p. 1667-1673.*
Dipersio "Stem cell stat, please!" bold, Oct. 15, 2003, vol. 102, No. 8. p. 2711.*
Clercq, the bicyclam AMD3100 story, Nature Review, Drug Discovery, vol. 2, Jul. 2003, 581-587.*
du Bois et al , J Natl Cancer Inst 2003;95:1320-30.*
Hendrix et al, Antimicrob. Agents Chemother. Jun. 2000, vol. 44, No. 6 1667-1673.*
Yopp et al, The Journal of Immunology, Jul. 15, 2004, vol. 173, No. 2, 855-865.*
Devine et al, J Clin Oncol vol. 22, No. 6, Mar. 15, 2004.*
Donahue, Robert E. et al., "Plerixafor (AMD3100) and granulocyte colony-stimulating factor (G-CSF) mobilize different CD34, cell populations based on global gene and microRNA expression signatures", Blood, 2009 114:2530-2541.

(Continued)

Primary Examiner — Jean Cornet

(57) ABSTRACT

This invention provides methods and compositions for modulating movement of eukaryotic cells with migratory capacity. More specifically, the invention provides anti-fugetactic agents and methods for the use thereof in enhancing an immune response.

6 Claims, 20 Drawing Sheets

(56) References Cited

OTHER PUBLICATIONS

Lapidot, T. et al., "The essential roles of the chemokine SDF-1 and its receptor CXCR4 in human stem cell homing and repopulation of transplanted immune-deficient NOD/SCID and NOD/SCID/B2m null mice", Leukemia (2002) 16, 1992-2003. doi:10.1038/sj:leu.2402684.
PCT/ISA/210, WO, The General Hospital Corporation, ISR.
PCT/ISA/237, WO, The General Hospital Corporation, Written Opinion.
Schneider et al. Suradista NSC 651016 Inhibits the Angiogenic Activity of CXCL12-Stromal Cell-derived Factor 1 alpha. Clinical Cancer Research. Dec. 2002, vol. 8, pp. 3955-3960, especially pp. 3955 and 3958.
Zlatopolskiy et al. Reverse gear cellular movement mediated by chemokines Immunology and Cell Biology, Aug. 2001, vol. 79, pp. 340-344, especially p. 342.
C. J. Scotton et al. "Multiple Actions of the Chemokine CXCL12 on Epithelial Tumor Cells in Human Ovarian Cancer" Cancer Research 62: 5930-59-38 (Oct. 15, 2002).
Block, L. H. et al., Human Migration Inhibitory Factor: Purification and Immunochemical Characterization, The Journal of Experimental Medicine 47: 541-553 (1978).
Weisbart, R. H. et al., Neutrophil Migration Inhibition Factor from T Lymphocytes (NIF-T): Selective Removal of Biologic Activity by Human Peripheral Blood Neutrophils, Myelocytic Leukemia Cells, and Differentiated HL-60 Cells, The Journal of Immunology 128(10): 457-462 (Jan. 1982).
Office Action issued in EP 00922067.4, Received Aug. 6, 2011.
Bardon, S., et al. "Monoterpenes Inhibit Cell Growth Cell Cycle Cell Progression and Cyclin D1 Gene Expression in Human Breast Cancer Cell Lines". Nutrition and Cancer 32(1), 1-7 (1998).
Yang et al. "Efficient Lysis of Human Immunodeficiency Virus Type 1-Infected Cells by Cytotoxic T Lymphocytes." Journal of Virology (1996) 5799-5806.
Cao et al. "Cytotoxic T-Lymphocyte Cross-Reactivity among Different Human Immunodeficiency Virus Type-1 Clades: Implications for Vaccine Development." Journal of Virology (1997) 8615-8623.
Yang et al. "Suppression of Human Immunodeficiency Virus Type-1 Replication by CD8+ Cells: Evidence for HLA Class I-Restricted Triggering of Cytolytic and Noncytolytic Mechanisms." Journal of Virology (1997) 3120-3128.
Wunderlich et al. "Assays for T Cell Function, Induction and Measurement of Cytotoxic T Lymphocyte Activity." Current Protocols in Immunology (1997) 3.11.1-3.11.20 Supplement 21.
Oyaizu et al. "Human Immunodeficiency Virus Type 1 Envelope Glycoprotein gp120 Produces Immune Defects in CD4+ T Lymphocytes by Inhibiting Interleukin2 mRNA." Proc. Natl. Acad. Sci. (1990) 87: 2379-2383.
Schols et al. "Human Immunodeficiency Virus Type 1 gp120 Induces Anergy in Human Peripheral Blood Lymphocytes by Inducing Interleukin-10 Production." Journal of Virology (1996) 4953-4960.
Liegler et al. "HIV-1 gp120 and anti-gp120 induce reversible unresponsiveness in peripheral CD4 T lymphocytes." J Acquire Immune Defic Syndr (1994) 7(4): 340-8.
Manca et al. "Inhibitory activity of HIV envelope gp120 dominates over its antigenicity for human T cells." Clin. Exp. Immunol. (1992) 88, 17-22.
Chirmule et al. "Inhibition of Functional Properties of Tetanus Antigen-Specific T-Cell Clones by Envelope Glycoprotein GP120 of Human Immunodeficiency Virus." Blood (1990) 75(1) 152-159.
Lavergne et al. "Leukocyte Migration Inhibition in Vitro in Bladder Carcinoma." Cancer Research 39 (1979) 1985-1988.
Wright wt. Al. "Cell-Mediated Immunity in Patients with Renal Cell Carcinoma as Measured by Leukocyte Migration Inhibition Test." Urology (1978) XII(5): 525-531.
Buening "Cell-Mediated Immune Response in Anaplasmosis as Measured by a Micro Cell-Mediated Cytotoxicity Assay and Leukocyte Migration-Inhibition Test." Am J Vet Res (1976) 37(10); 12156-1218.
Potter et al. "Lymphocyte proliferation and cytotoxic assays using flat-bed scintillation counting." Journal of Immunological Methods (1987): 105 171-177.
Kimpton et al. "Lymphocyte Migration during the Development of Regional Lymph Node Anergy in Experimental Tumor Growth." Cellular Immunology (1983) 75, 13-21.
Kristensen "A Comparative Study of Natural Cytotoxicity and the Leukocyte Migration Inhibition in Human Melanoma Stages I and II." J. Cancer Res. Clin. Oncol. (1980) 96: 181-191.
Sano et al. "A new Fluorochromasia method using a fluorescence microplate reader for assay of cytotoxic activity of carp leucocytes." Veterinary Immunology and Immunopathology (1995);47, 173-178.
Rajkovic et al. "Rapid Microassays of Phagocytosis, Bacterial Killing, Superoxide and Hydrogen Peroxide Production by Human Neutrophils in Vitro." Journal of Immunological Methods (1985): 78, 35-47.
Miller et al. "Killing of Cryptococcus neoformans Strains by Human Neutrophils and Monocytes." Infection and Immunnology (1991) 59(1): 24-28.
Suzuki et al. "Diverse Transcriptional Response of CD4+ T Cells to Stromal Cell-Derived Factor (SDF)-1: Cell Survival Promotion and Priming Effects of SDF-1 on CD4+ T Cells." The Journal of Immunology (2001), 167: 3064-3073.
Staudt et al. "Genomic Views of the Immune System." Annu. Rev. Immunol. (2000), 18:829-859.
Laster et al. "Target-induced changes in macrophage migration may explain differences in lytic sensitivity among simian virus 40-transformed fibroblasts." J. Immunol. (1988) Jul. 1: 141(1):221-7.
Gurdon et al. "Morphogen gradient interpretation." Nature (2001) 413(6858):797-803.
Dyson et al. "The interpretation of position in a morphogen gradient as revealed by occupancy of activin receptors." Cell (1998) 93(4): 557-68.
McDowell et al. "Formation of a functional morphogen gradient by a passive process in tissue from the early Xenopus embryo." Int. J. Dev. Biol. (2001) 45(1 Spec No): 199-207.
Cadigan "Regulating morphogen gradients in the *Drosophila* wing." Semin Cell Dev Biol (2002) 13(2): 83-90.
Shimizu et al. "A quantitative analysis of signal transduction from activin receptor to nucleus and its relevance to morphogen gradient interpretation." Proc Natl Acad Sci USA (1999) 96(12): 6791-6.
McDowell et al. "Activin has direct long-range signalling activity and can form a concentration gradient by diffusion." Curr Biol (1997) 7(9): 671-81.
Ryan et al. "The Xenopus eomesodermin promoter and its concentration-dependent response to activin." Mech Dev (2000) 94(1-2): 133-46.
Temaru et al. "High glucose enhances the gene expression of interleukin-8 in human endothelial cells, but not in smooth muscle cells: possible role of interleukin-8 in diabetic macroangiopathy." Diabetologia (1997) 40(5): 610-3.
TONETTIi et al. "Neutrophil migration into the gingival sulcus is associated with transepithelial gradients of interleukin-8 and ICAM-1." J. Periodontol (1998) 69(10): 1139-47.
Braisted et al. "graded and lamina-specific distributions of ligands of EphB receptor tyrosine kinases in the developing retinotectal system." Dev Biol (1997) 191 (1): 14-28.
Christopherson et al. "Transgenic overexpression of the CC chemokine CCL21 disrupts T-cell migration." Blood (2001) 98(13): 3562-8.
Turner et al. "Hypoxia inhibits macrophage migration." Eur J Immunol. (1999) 29(7): 2280-7.
Janowska-Wieczorek et al. "Differential MMP and TIMP production by human marroe and peripheral blood CD34(+) cells in response to chemokines." Exp Haematol (2000) 28(11): 1274-84.
Nellen et al. "Direct and long-range action of a DPP morphogen gradient." Cell (1996) 85(3): 357-68.
Campbell et al. "Transducing the Dpp morphogen gradient in the wing of *Drosophilia*: regulation of Dpp targets by brinker." Cell (1999) 96(4): 553-62.
Grimm et al. "Control of the gene optomotor-blind in *Drosophilia* wing development by decapentaplegic and wingless." Science (1996) 271(5255): 1601-4.

(56) References Cited

OTHER PUBLICATIONS

Jazwinska et al. "The *Drosophilia* gene brinker reveals a novel mechanism of Dpp target gene regulation." Cell (1999) 96(4): 563-73.
Staehling-Hampton et al. "Dpp induces mesodermal gene expression in *Drosophilia* ." Nature (1994) 372(6508): 783-6.
Kiecker et al. "A morphogen gradient of Wnt/beta-catenin signalling regulates anteroposterior neural patterning in Xenopus." Development (2001) 128(21): 4189-201.
Papageorgiou "A physical force may expose Hox genes to express in a morphogenetic density gradient." Bull Math Biol (2001) 63(1): 185-200.
Tomoyasu et al. "The decapentaplegic morphogen gradient regulates the notal wingless expression through induction of pannier and u-shaped in *Drosophilia* ." Mech Dev (2000) 96(1): 37-49.
Gurdon et al. "Single cells can sense their position in a morphogen gradient." Development (1999) 126(23):5309-17.
Gurdon et al."An experimental system for analyzing response to a morphogen gradient." Proc. Natl. Acad. Sci. USA (1996) 93: 9334-9338.
Bao et al. "Temporal Gradient in Shear but not Steady Shear Stress Induces PDGF-A and MCP-1 Expression in Endothelial Cells." Arterioscler Thromb Vasc Biol. (1999) 19: 996-1003.
Rutishauser, R, et al., T-Cells Differentially Express Genes Encoding Molecules Involved in Chemokine Signal Transduction When Migrating Towards or Away from Gradients of SDF-1(CXCL 12) Abstract, Jan. 7, 2003.
Bagnard et al. "Semaphorins act as attractive and repulsive guidance signals during the development of cortical projections." Development 125, 5043-5053 (1998).
Shioi et al. "Oxygen as Attractant and Repellent in Bacterial Chemotaxis." Journal of Bacteriology 169(7) 3118-3123 (1987).
Klein et al. "Perlecan in Human Bone Marrow: A Growth-Factor-Presenting, but Anti-Adhesive, Extracellular Matrix Component for Hematopoietic Cells." Matrix Biology 14, 457-465 (1994).
Zaitseva et al. "CXCR4 and CCR5 on Human Thymocytes: Biological Function and Role in HIV-1 Infection." The Journal of Immunology 3103-3113 (1998).
Bailey, et al., "Chemotaxis by Entamoeba Histolytica" J. Protozool (1985) 32(2):341-346. Abstract.
Berman, et al., "Functional characteristics of histamine receptor-bearing mononuclear cells. II Identification and characterization of two histamine-induced human lymphokines that inhibit lymphocyte migration. "J Immunol., Sep.;133(3):1495-504 (1984).
Chaffin, K.E. and Perlmutter, RM. "A Pertussis Toxin-Sensitive Process Controls Thymocyte Emigration" JImmunol. (1991) 21(10):2565-73. Abstract.
Friedl, et al., "Locomotor recruitment and negative chemotaxis of human lymphocytes confronted with autologous primary cancer explants in three-dimensional (3-D) collagen lattices in vitro", Proceedings of the America Assoc. for Cancer Res. Annual, 37:446 (1996). Abstract.
Gebhard, R., et al., "Inter-Alpha-Trypsin Inhibitor Complex Component II Precursor-Human", PIR Protein Sequence, from "Complementary DNA and Derived Amino Acid Sequence of the Precursor of One of Three Protein Components of the Inter-Alfpha Trypsin Inhibitor Complex" FEBS Lett. 229: 63-67 (1988).
Keating, M.T, and Bonner, J.T. Negative-Chemotaxis-in-Cellular-Slime Molds J Bacterial. (1977)⁻ 130(1):1-44-147Abstract.
Khan, et al., "Chemotactic Signal Integration in Bacteria" Proc. Natl. Acad. Sci. USA (1995) 92(21):9757-9761Abstract.
Keller, et al., "Diverging effects of chemo tactic serum peptides and synthetic formylmethionylleucyl phenyl alanine on neutrophil locomotion and adhesion", Immunolo• , 42(3):379-384(1981) Abstract.
Luster "Chemokines-chemotactic cytokines that mediate inflammation." New England Journal of Medicine 338(7): 436-445 (1998).
Liu, et al., "Analysis of chemokine (S) produced by mouse thymic stromal cell lines" Shili Yen Sheng Wu Hsueh Pao_ Mar. 1996;29(1):25-32. Chinese Abstract.

McFadden, et al., "Rat lymphokines control the migration of nonsensitized lymphocytes", Cellular Immunology, 118(2):345-357(1989) Abstract.
Baggiolini, "Chemokines and leukocyte traffic", Nature, 392:565-568, 1998.
Bleul, et al. "A highly efficacious lymphocyte chemoattractant, stromal cell derived factor 1 (SDF-I)" J Exp Med184(3):1101-1109, 1996.
Bleul et al., "The lymphocyte chemoattractant SD—is a ligand for LESTR/ fusion and blocks HIV-1 entry", Nature,382(6594):829-833, 1996.
Kim et a "Differential Chemotactic Behavior of Developing T Cells in Response to Thymic Chemokines", Blood, 91(12)4434-4443,1998.
Kim et al . "CKB-I /Macrophage Inflammatory Protein-3B/EBI:1-Ligand Chemokine Is an Efficacious Chemoattractant for T and B Cells" J Immunol, 160:2418-2424, 1998.
Colamarino-et al., TheAzonal Chemoattractant Netrin-1 Is Also a Chemorepellent for Trochlear Motor Axons, Cell, 8 1 :621-629, 1995.
Wells, T.N., et al., "Definition, Function and Pathophysiological Significance of Chemokine Receptors", TIPS 19:376-380, 1998.
Arakaki et al., "T134, a Small-Molecule CXCR4 Inhibitor, Has No Cross-Drug Resistance with AMD3100, a CXCR4 Antagonist with a Different Structure", J Viro173(2):1719-1723, 1999.
Heveker et al., "Dissociation of the signaling and antiviral properties of SDF-1-derived small peptides", Current Biol, 8(7):369-376, 1998.
Loetscher et al., "N-terminal Peptides of Stromal Cell-derived Factor-1 with CXC Chemokine Receptor 4 Agonist and Antagonist Activities", J Biol Chem, 273(35):22279-22283, 1998.
Luo et al., "Attachment of C-Terminus of SDF-1 Enhances the Biological Activity of Its N-Terminal Peptide", Biochem Biophys Res Cormmun, 264(1):42-47, 1999.
Murakami et al., "A Small Molecule CXCR4 Inhibitor that Blocks T Cell Line-tropic HIV-1 Infection", JExp Med, 186(8);1389-1393,1997.
Poznansky et al., "Thymocyte emigration is mediated by active movement away from stroma-derived factors", J Clin Invest, 109(8):1101-1110, 2002.
Poznansky et al., "Active movement of T cells away from a chemokine", Nat Med, 6(5):543-548, 2000 Abstract Only.
Poznansky et al., "Tissue source dictates lineage outcome of human fetal CD34(+) CD38(-) cells", Exp Hematol, 29(6):766-77 , 2 01 Abstract Only.
Poznansky et al., "Efficient generation of human T. cells from a tissue-engineered thymic organoid", Nat Biotechnol, 18(7):729:734,2000 Abstract Only.
Olszak, et al., "Extracellular calcium elicits a chemokinetic response from monocytes in vitro and in vivo", J Clin Invest, 105(9):1299-1305, 2000 Abstract Only.
Poznansky et al., " Inhibition of human immunodeficiency virus replication and growth ad⁻ vantage of CD4+ T cells and moncytes derived from CD34+ cells transduced with an intracellular antibody directed against human immunodeficiency virus type 1 Tat", Hum Gene Ther, 10(15):2505-2514,1999 Abstract Only.
Adams et al, "Isolation and transduction of CD34+ cells-from small quantities of peripheral blood form HIV-1 infected patients not treated with hemopoietic growth factors", J Acquir Immune Defic Syndr, 21(1):1-8, 1999 Abstract Only.
Adams et al., "Heterologous cells cooperate to augment stem cell migration, homing, and engraftment", Blood, 10 I (I):45-51, 2003 Abstract Only.
Niggemann et al. "Locomotory phenotypes of human tumor cell lines and T lymphocytes in a three-dimensional collagen lattice." Cancer Lett., 118(2): 173-80 (1997).
International Search Report, mailed Sep. 13, 2000.
Definition for Repellent, http://www.the freedictonary.com/repellent, pp. 1-2, The American Heritage Dictionary of the English Language, fourth edtion, 2009, published by the Hougtho Mifflin Company.

(56) References Cited

OTHER PUBLICATIONS

Bielenberg et al., "Semaphorin 3F, a Chemorepulsant for Endothelial Cells, Induces a Poorly Vascularized, Encapsulated, Nonmetastatic Tumor Phenotype", Nov. 2004, J Clin Invest, vol. 114, No. 9, pp. 1260-1271.

Brainard et al., "Migration of Antigen-Specific T Cells Away from CXCR4-Binding Human Immunodeficiency Virus Type 1 gp120", May 2004, Journal of Virology, vol. 27, No. 10, pp. 5184-5193.

Damas et al., "Stromal Cell-Derived Factor-13B1 in Unstable Angina Potential Antiinflammatory and Matrix-Stabilizing Effects", Jul. 2, 2002, Circulation, 106(1), 36 013 42.

Gajewski, Thomas, "Failure at the Effector Phase: Immune Barriers at the Level of the Melanoma Tumor Microenvironment", Sep. 15, 2007, Clin Cancer Res, 13(18), pp. 5256-5261.

Hovav et al, "X4 Human Immunodeficiency Virus Type 1 gp120 Down-Modulates Expression and Immunogenicity of Codelivered Antigens", Nov. 2009, Journal of Virology, vol. 83, No. 21, pp. 10941-10950.

Ishii et al., "Chemorepulsion by Blood S1P Regulates Osteoclast Precursor Mobilization and Bone Remodeling in Vivo", Dec. 2010, J Exp Med, 207(13), pp. 2793-27988.

Kohrgruber et al., "Plasmacytoid Dendritic Cell Recruitment by Immobilized CXCR3 Ligands", Dec. 2004, J Immunol, vol. 73, No. 11, pp. 6592-6602.

Mathias et al., "Resolution of Inflammation by Retrograde Chemotaxis of Neutrophils in Transgenic Zebrafish", Dec. 2006, J. Leuk. Biol., vol. 80, No. 6, pp. 1281-1288.

Misslitz et al., "Thymic T Cell Development and Progenitor Localization Depend on CCR7", Aug. 9, 2004, J Exp Med, vol. 200, No. 4, pp. 481-491.

Papeta et al., "Long-Term Survival of Transplanted Allogeneic Cells Engineered to Express a T Cell Chemorepellent", Jan. 27, 2007, Transplantation, 83(2), pp. 174-183.

Righi et al., "CXCL/CXCR4 Blockade Induces Multimodal Antitumor Effects That Prolong Survival in an Immunocompetent Mouse Model of Ovarian Cancer", Aug. 15, 2011, Cancer Res, 71(16), pp. 5522-5534.

Santosuosso et al., "R5-SHIV Induces Multiple Defect in T Cell Function During Early Infection of Rhesus Macaques Including Accumulation of T Reg Cells in Lymph Nodes", Apr. 2011, PLoS One, 6(4), e18465.

Shiao et al., "Immune Microenvironmental in Solid Tumors: New Targets for Therapy", 2011, Genes & Dev, 25, pp. 2559-2572.

Sroussi et al., "Oxidation of Methionine 63 and 83 Regulates the Effect of A10019 on the Migration of Neutrophils in Vitro", Mar. 2007, J Leuk Biol, 81(3), pp. 818-824.

Stevceva et al., "The Efficacy of T Cell-Mediated Immune Responses is Reduced by the Envelope Protein of the Chimeric HIV-1/SIV-KB9 Virus in Vivo", Oct. 15, 2008, J Immunol, 181(8), pp. 5510-5521.

Tharp et al., Neutrophil Chemorepulsion in Defined Interleukin-8 Gradients in Vitro and in Vivo, Mar. 2006, J Leukoc Biol, 79(3), pp. 539-554.

Vianello et al., "Murine B16 Melanomas Expressing High Levels of the Chemokine Stromal-DerivedFactor-1/CXCL12 Induce Tumor-Specific T Cell Chemorepulsion and Escape From Immune Contro"l, Mar. 2006, J Immunol, 176(5), pp. 2902-2914.

Witt et al., "The Ins and Outs of CCR7 in the Thymus", Aug. 16, 2004, J Exp Med, 200(4), pp. 405-409.

Holtan et al. "AMD3100 Affects Autograft Lymphocyte Collection and Progression-Free Survival After Autologous Stem Cell Transplantation in Non-Hodgkin Lymphoma", 2007, Clin Lymphoma Myeloma, 7, pp. 315-318. (PubMed id:17324341).

Gazitt et al. "Improved Mobilization of Peripheral Blood CD34+ Cells and Dendritic cells by AMD3100 Plus Granulocyte-Colony-Stimulating Factor in Non-Hodgkin's Lymphoma Patients", 2007, Stem Cells Dev, 16, pp. 657-666. (PubMed id:17784839).

Calandra et al. "AMD3100 Plus G-CSF Can Successfully Mobilize CD34+ Cells from Non-Hodgkin's Lymphoma, Hodgkin's Disease and Multiple Myeloma Patients Previously Failing Mobilization with Chemotherapy and/or Cytokine Treatment: Compassionate Use Data", 2008, Bone Marrow Transplant,41, pp. 331-338. (PubMed id:17994119).

Cashen et al. "A Phase II Study of Plerixafor (AMD3100) Plus G-CSF for Autologous Hematopoietic Progenitor Cell Mobilization in Patients with Hodgkin Lymphoma", 2008, Biol Blood Marrow Transplant, 14, pp. 1253-1261. (PubMed id:18940680).

Wagstaff. "Plerixafor: in Patients with Non-Hodgkin's Lymphoma or Multiple Myeloma", 2009, Drugs, 69, pp. 319-326. (PubMed id:19275275).

Dipersio et al. "3102 Investigators. Plerixafor and G-CSF Versus Placebo and G-CSF to Mobilize Hematopoietic Stem Cells for Autologous Stem Cell Transplantation in Patients with Multiple Myeloma", 2009, Blood, 113, pp. 5720-5726. (PubMed id:19363221).

Dipersio et al. "3101 Investigators. Phase III Prospective Randomized Double-Blind Placebo-Controlled Trial of Plerixafor Plus Granulocyte Colony-Stimulating Factor Compared with Placebo Plus Granulocyte Colony-Stimulating Factor for Autologous Stem-Cell Mobilization and Transplantation for Patients with Non-Hodgkin's Lymphoma", 2009, J Clin Oncol, 27, pp. 4767-4773. (PubMed id:19720922).

Ogilvie et al., "Eotaxin-3 is a Natural Antagonist for CCR and Exerts a Repulsive Effect on Human Monocytes, Aug. 2003, Blood, vol. 102, No. 3, pp. 789-794.

O'Hayre et al. "Emerging Concepts and Approaches for Chemokine-Receptor Drug Discovery", 2010, Expert Opinion on Drug Discovery, 5(11), pp. 1109-1122.

Karin, Nathan, The Multiple Faces of CXCL12 (SDF-I3B1) in the Regulation of Immunity During Health and Disease, Sep. 2010, J Leuk Biol, vol. 88, pp. 463-473.

Balkwill, Fran, "Cancer and the Chemokine Network," Nature Reviews, vol. 4, Jul. 2004, pp. 540-550.

Dunussi-Joannopoulos et al., "Efficacious immunomodulatory activity of the chemokine stromal cell-derived factor 1 (SDF-1): local secretion of SDF-1 at the tumor site serves as T-cell chemoattractant and mediates T-cell-dependent antitumor responses," Blood, vol. 100, No. 5, 2002, pp. 1551-1558.

Hatse et al., "Chemokine receptor inhibition by AMD3100 is strictly confined to CXCR4," FEBS, vol. 527, 2002, pp. 255-262.

Ilhan et al., "CSCL12/SDF-1 over-expression in human insulinomas and its biological relevance," Molecular and Cellular Endocrinology, vol. 298, No. 1-2 ISSN: 0303-7207, (2009) pp. 1-10.

Koshiba et al., "Expression of Stromal Cell-derived Factor 1 and CXCR4 Ligand Receptor System in Pancreatic Cancer: A Possible Role for Tumor Progression," Clinical Cancer Research, vol. 6, 3530-3535, Sep. 2000.

* cited by examiner

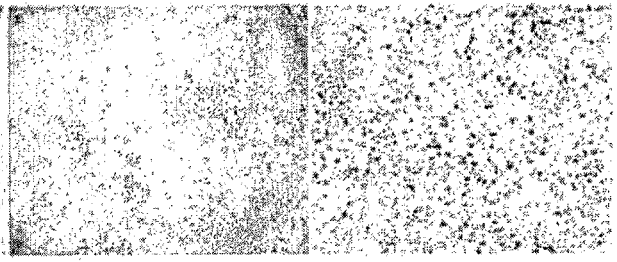
FIG. 5A  FIG. 5B  FIG. 5C
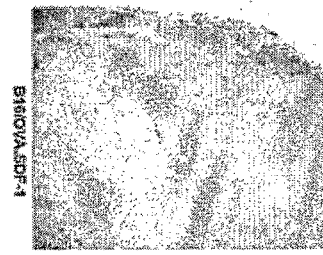
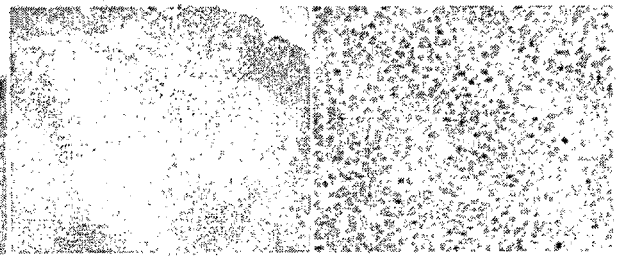
FIG. 5D  FIG. 5E  FIG. 5F FIG. 8A FIG. 8B FIG. 8C
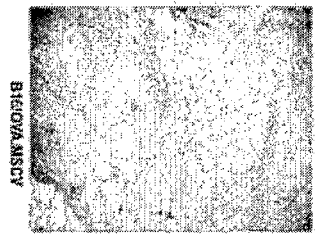 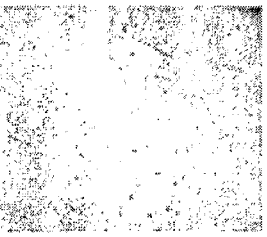 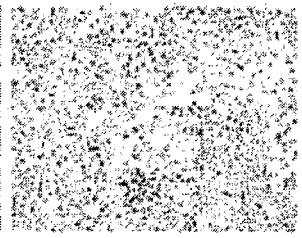
  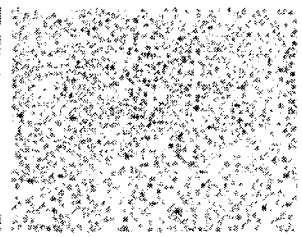
FIG. 8D FIG. 8E FIG. 8F
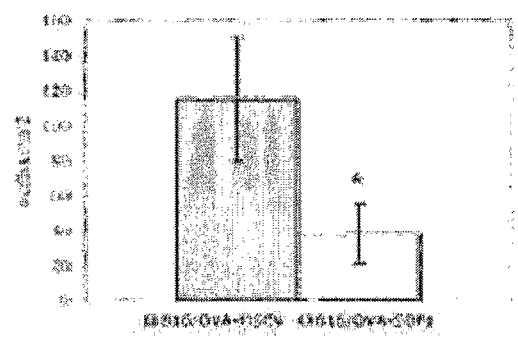
FIG. 8G FIG. 10A  FIG. 10B  FIG. 10C
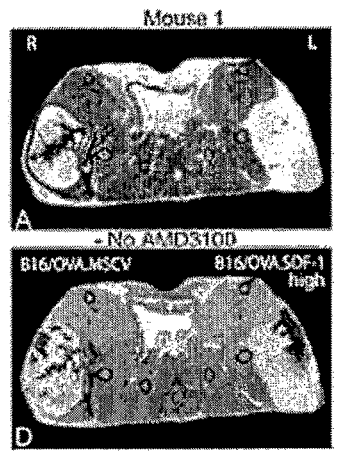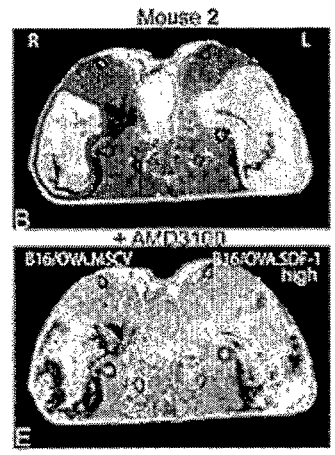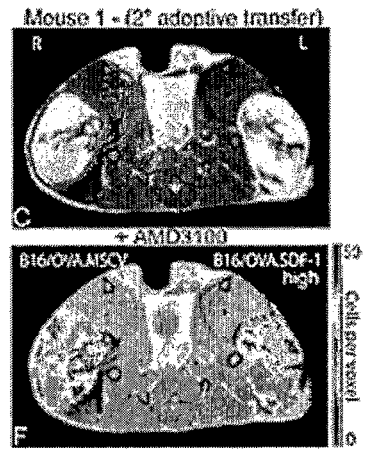
FIG. 10D  FIG. 10E  FIG. 10F
FIG. 10G  FIG. 10H  FIG. 10K  FIG. 10L
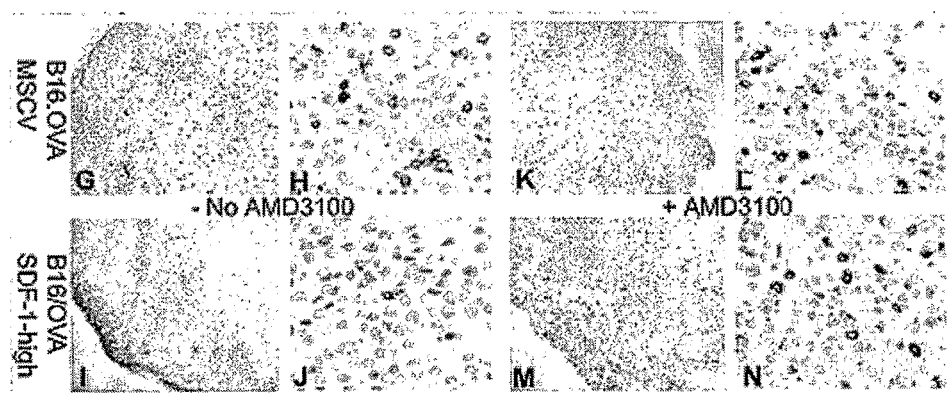
FIG. 10I  FIG. 10J  FIG. 10M  FIG. 10N FIG. 11A  FIG. 11B
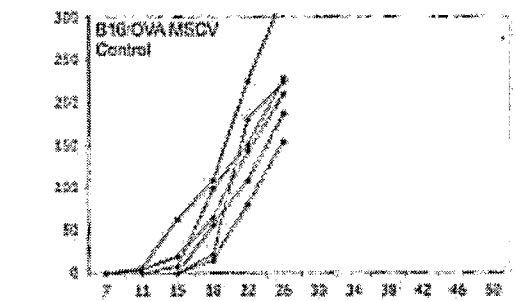
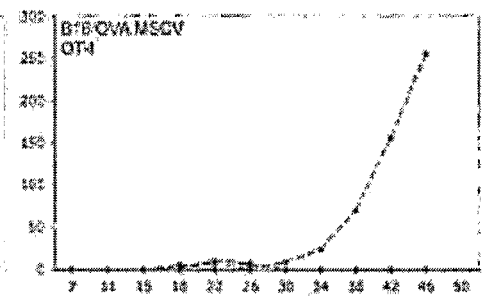
FIG. 11C  FIG. 11D
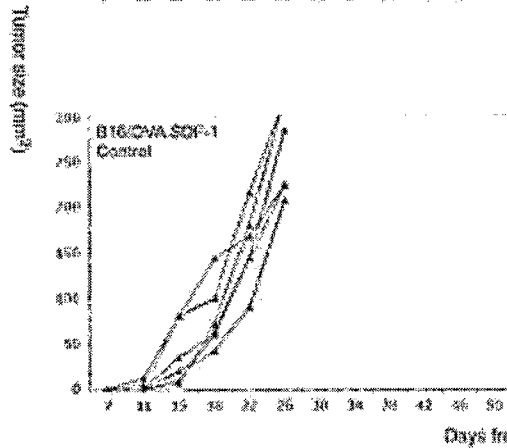
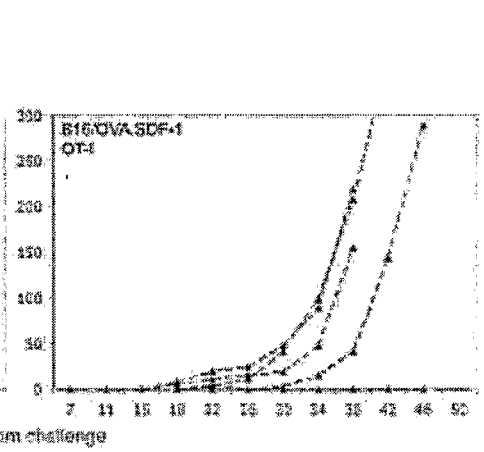
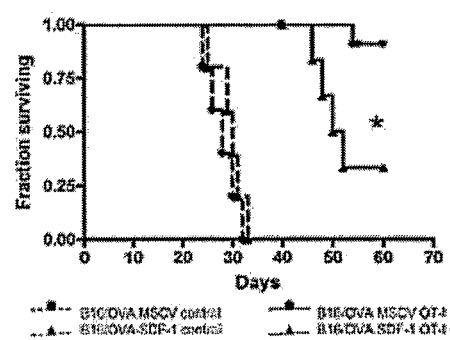
FIG. 11E FIG. 12A          FIG. 12B
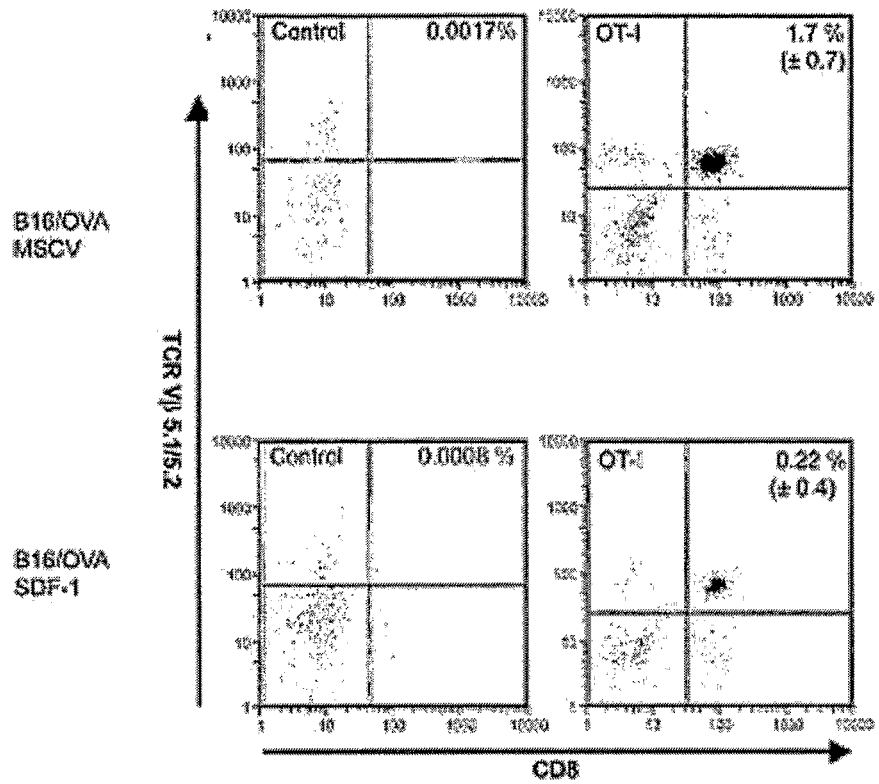
FIG. 12C          FIG. 12D
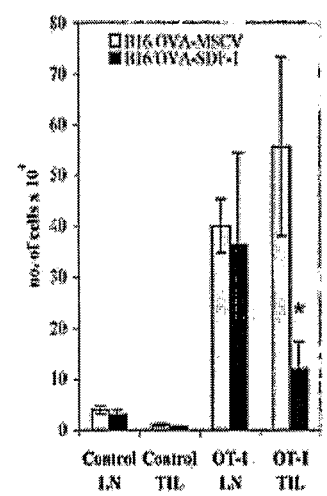
FIG. 12E FIG. 15A
FIG. 15C
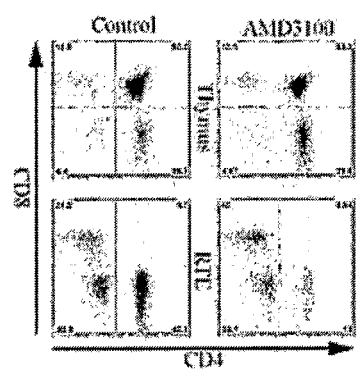
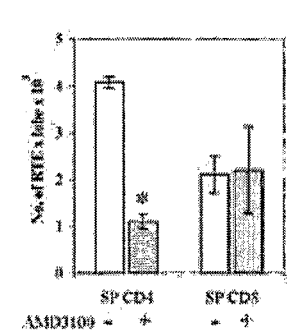
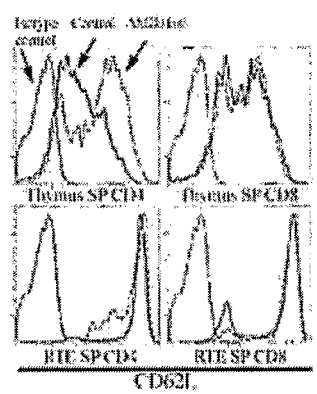
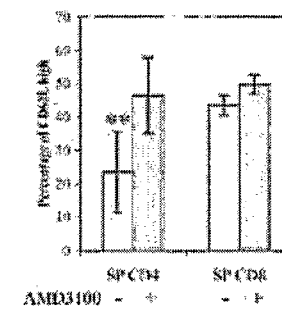
FIG. 15B
FIG. 15D Time (sec)

ANTI-FUGETACTIC AGENTS FOR THE TREATMENT OF OVARIAN CANCER

RELATED APPLICATIONS/PATENTS & INCORPORATION BY REFERENCE

This application is the U.S. national phase application, pursuant to 35 U.S.C. §371, of PCT international application Ser. No. PCT/US2005/040218, filed Nov. 4, 2005, designating the United States and published in English on Dec. 28, 2006 as publication WO 2006/137934 A2, which claims priority to U.S. provisional application Ser. No. 60/625,733, filed Nov. 5, 2004. The entire contents of the aforementioned patent applications are incorporated herein by this reference.

STATEMENT OF GOVERNMENTAL INTEREST

This work was funded in part by grant number NHLBI-44851 from the National Institutes of Health. Accordingly, the United States Government may have certain rights to this invention.

BACKGROUND OF THE INVENTION

Cell movement in response to specific stimuli is observed to occur in prokaryotes and eukaryotes (Doetsch R N and Seymour W F., 1970; Bailey G B et al., 1985). Cell movement seen in these organisms has been classified into three types: chemotaxis or the movement of cells along a gradient towards an increasing concentration of a chemical; negative chemotaxis which has been defined as the movement down a gradient of a chemical stimulus; and chemokinesis or the increased random movement of cells induced by a chemical agent. The receptors and signal transduction pathways for the actions of specific chemotactically active compounds have been extensively defined in prokaryotic cells. Study of *E. Coli* chemotaxis has revealed that a chemical which attracts the bacteria at some concentrations and conditions may also act as a negative chemotactic chemical or chemorepellent at others (Tsang N et al., 1973; Repaske D) and Adler J. 1981; Tisa L S and Adler J., 1995; Taylor B L and Johnson M S., 1998).

Chemotaxis and chemokinesis have been observed to occur in mammalian cells (McCutcheon M W, Wartman W and H M Dixon, 1934; Lotz M and H Harris 1956; Boyden S V 1962) in response to the class of proteins, called chemokines (Ward S G and Westwick J; 1998; Kim C H et al., 1998; Baggiolini M, 1998; Farber J M; 1997). Additionally, Poznansky et al. (U.S. Pat. No. 6,448,054 and WO 2004/053165, which are incorporated by reference in their entirety) have observed chemorepellent, or fugetactic, activity in mammalian cells. Improved control over chemotaxis, chemokinesis and fugetaxis, such as in mammalian systems, is desirable.

SUMMARY OF THE INVENTION

Agents with migratory-cell repellant activity (hereinafter "fugetactic agents" and "fugetactic activity," and/or "chemo-fugetaxis") are described herein. The invention provides pharmaceutical compositions containing the foregoing fugetactic agents, and various therapeutic and diagnostic methods utilizing the foregoing fugetactic agents. The invention also provides fugetactic polypeptides and agents which bind such polypeptides, including antibodies. The foregoing can be used, inter alia, in the treatment of conditions characterized by a need to modulate migratory-cell movement in specific sites in a subject. Important such sites include inflammation sites. The invention also provides methods for identifying agents useful in the modulation of such fugetactic activity.

The present invention is based, in part, upon the appreciation that dimerization of a G protein coupled receptor and/or receptor ligand is important for imparting fugetactic activity. Thus, the invention relates to fugetactic compounds which comprise ligand dimers, functional fragments and derivatives thereof and methods of inducing fugetaxis by contacting such compounds with a cell which expresses the corresponding G protein coupled receptor. The ligand dimers can be made from native or synthetic ligands of the G protein coupled receptor. For example, the ligands can be chemokines. Preferably, the ligand dimers are dimers of native ligands. In a particularly preferred embodiment, the fugetactic compounds are stable in vivo (e.g., resistant to degradation to the monomeric ligand), selectively fugetactic and are substantially inactive as chemoattractant compounds.

The fugetactic compounds can be any compound resulting in or causing chemokine and/or chemokine receptor dimerization. Chemokines can act as monomers on chemokine receptors at concentrations below 100 nM, thereby functioning as chemoattractants. Certain chemokines, including IL-8 and SDF-1 can also serve as chemorepellents at high concentrations (e.g., above 100 nM) where much of the chemokine exists as a dimer. Dimerization of the chemokine elicits a differential response in cells, causing dimerization of chemokine receptors, an activity which is interpreted as a chemorepellent signal. Thus, binding of the dimeric chemokine and dimerization of the cognate chemokine receptor on the cell surface can elicit a differential signal in the cell, including an increased calcium flux and concomitant alterations of secondary messenger molecules, to thereby induce fugetaxis.

In another aspect, the invention relates to anti-fugetactic compounds which inhibit fugetaxis by inhibiting receptor dimerization. Such compounds can include antibodies that target the amino acids in the receptor necessary for dimerization. In a particularly preferred example, such anti-fugetactic compounds possess selective antifugetactic activity, leaving the chemoattractant properties of the receptor substantially intact. For example, the anti-fugetactic compound can interfere with fugetactic ligand activity or receptor binding, thereby allowing the receptor to receive chemoattractant signals.

In one embodiment, the anti-fugetactic compound can be a compound which inhibits interaction between native ligand dimers and the G protein coupled receptor. Preferably the inhibition is selective. For example, a compound that competitively inhibits the native ligand dimer can be used. Compounds that competitively inhibit the native ligand dimer may comprise two protein chains wherein at least one protein chain is a ligand derivative which has been modified to delete the receptor binding function. The second protein chain can be a polypeptide that binds the receptor. Together, the compound is capable of binding to but not activating the fugetactic activity of the receptor.

Anti-fugetactic agents therefore include any agents that specifically inhibit chemokine and/or chemokine receptor dimerization, thereby blocking the chemorepellent response to a fugetactic agent. Blocking the chemorepellent effect of high concentrations of a chemokine secreted by a tumor can be accomplished by anti-fugetactic agents which inhibit chemokine dimer formation or chemokine receptor dimer formation. For example, antibodies that target and block chemokine receptor dimerization, for example, by interfering with the dimerization domains or ligand binding can be anti-fugetactic agents. Where desired, this effect can be achieved without inhibiting the chemotactic action of monomeric chemokine.

In other embodiments, the anti-fugetactic agent is a CXCR4 antagonist, CXCR3 antagonist, CXCR4/SDF-1 antagonist or selective PKC inhibitor. Such compounds include AMD3100, KRH-1636, T-20, T-22, T-140, TE-14011, 14012 and TN14003; TAK-779, AK602 and SCH-351125; and Tannic acid and NSC 651016 and thalidomide and GF109230X.

In another aspect, the invention further relates to assays for identifying the compounds described above. Such assays can include contacting cells (e.g., T-cells) which express the receptor, the receptor and/or a receptor ligand in the presence of a test compound and detecting the presence or absence of dimerization of the receptor and/or ligand. Preferably, the assay includes the step of detecting the presence or absence of fugetaxis of cells (e.g., T-cells) under conditions wherein the cells fugetactically respond to the receptor and ligand in the absence of such test compound. The assay can optionally comprise the step of detecting the presence or absence of chemotaxis or chemokinesis of cells (e.g., T-cells) under conditions wherein the cells chemotactically or chemokinetically respond to the receptor and ligand in the absence of such test compound.

In one embodiment, the invention provides a method of identifying a fugetactic agent, the method comprising the steps of: contacting an agent suspected of being a fugetactic agent with a cell with migratory capacity, measuring the zone of clearance relative to the cell; and determining that the zone of clearance is of a sufficient size to thereby identify the fugetactic agent. In certain embodiments, the cell with migratory capacity is a hematopoietic cell, a neural cell, an epithelial cell, a mesenchymal cell, an embryonic stem cell or a germ cell.

In another embodiment, the invention includes a method of identifying an anti-fugetactic agent comprising the steps of contacting an agent suspected of being an anti-fugetactic agent with a polypeptide, such as a polypeptide ligand for a G protein coupled receptor, that will dimerize in the presence of a fugetactic agent, contacting the polypeptide with a fugetactic agent; and determining that dimerization of the polypeptide is inhibited, thereby identifying an anti-fugetactic agent.

In yet another embodiment, a method of identifying an anti-fugetactic agent is provided, the method comprising the steps of contacting an agent suspected of being an anti-fugetactic agent with a cell with migratory capacity in the presence of a fugetactic agent, measuring movement of the cell with migratory capacity relative to the fugetactic agent, and determining whether the movement of the cell with migratory capacity is inhibited, thereby identifying an anti-fugetactic agent.

In yet another aspect, the invention further relates to methods of modulating fugetactis to provide a therapeutic response in a subject. In one embodiment, a method of enhancing an immune response in a subject having a condition that involves a specific site, is provided. The method involves locally administering to a specific site in a subject in need of such treatment an anti-fugetactic agent described herein in an amount effective to inhibit immune cell-specific fugetactic activity at the specific site in the subject. In some embodiments, the specific site is a site of a pathogenic infection. In certain embodiments, the specific site is a germ cell-containing site. In further embodiments, the specific site is an area immediately surrounding a tumor. In certain embodiments, the anti-fugetactic agent is a cytokine binding agent. In other embodiments, the cytokine binding agent is an anti-cytokine antibody or a cytokine agonist. In a preferred embodiment the cytokine is SDF-1α.

In another embodiment, a method of increasing migration of immune cells to a tumor site is provided, the method comprising administering to an area immediately surrounding a tumor an anti-fugetactic agent described herein in an amount effective to inhibit immune cell-specific fugetactic activity, thereby increasing migration of immune cells to a tumor site.

According to a further aspect of the invention, a method of inhibiting tumor cell metastasis in a subject, is provided. The method involves locally administering to a tumor site in a subject in need of such treatment an anti-fugetactic agent described herein in an amount effective to inhibit metastasis of tumor cells from the tumor site in the subject. In certain embodiments, the anti-fugetactic agent is a cytokine binding agent. In other embodiments, the cytokine binding agent is an anti-cytokine antibody or a cytokine agonist. In a preferred embodiment the cytokine is SDF-1α.

In yet another embodiment, a method for treating cancer in a subject is provided, the method comprising inhibiting cell metastasis in the subject by administering to a tumor site in the subject an anti-fugetactic agent described herein in an amount effective to decrease movement of tumor cells away from the tumor site, thereby inhibiting tumor cell metastasis in the subject and thereby treating cancer in the subject. The cancer or tumor type can be one presently known to escape immune recognition in the absence of the methods described herein.

According to a further aspect of the invention, a method of contraception in a subject, is provided. The method involves administering to a subject in need of such treatment, an anti-fugetactic agent described herein in an amount effective to inhibit germ cell migration in the subject. In certain embodiments, the anti-fugetactic agent is a cytokine binding agent. In some embodiments, the cytokine binding agent is an anti-cytokine antibody or a cytokine agonist. In a preferred embodiment the cytokine is SDF-1α.

The invention also relates to kits for using the compounds as described above comprising the compounds and instructions for use.

These and other aspects of the invention, as well as various advantages and utilities, will be more apparent with reference to the detailed description of the preferred embodiments.

BRIEF DESCRIPTION OF THE DRAWINGS

The following Detailed Description, given by way of example, but not intended to limit the invention to specific embodiments described, may be understood in conjunction with the accompanying drawings, incorporated herein by reference. Various preferred features and embodiments of the present invention will now be described by way of non-limiting example and with reference to the accompanying drawings in which:

FIG. 5: Paraffin-embedded sections of tumors from immunized mice were stained with H&E (A and D) or with polyclonal α-CD3 Ab (B,C,E, and F).

FIG. 8: Immunohistochemical studies of T-cell infiltration in B16/OVA tumors correlates with MR imaging.

FIG. 11: Potent antitumor activity of persistent adoptively transferred OT-I CD8+ cells is overcome when SDF-1 is locally expressed.

FIG. 12: FACScan identification of adoptively transferred OT-I CTL from recovered tumors and lymph nodes (LN).

FIG. 15: FACS plots and graphic analyses depicting CD4, CD8, and CD62L staining of thymic cells and recent thymic emigrants (RTE) from untreated vs. AMD3100-treated fetal thymus organ cultures (FTOC).

DETAILED DESCRIPTION OF THE INVENTION

I. Definitions

Figure 1A:
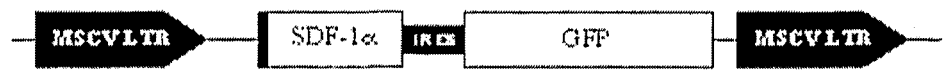
FIG. 1: SDF-1 expression construct used for transduction of B16/OVA melanoma cells.

"Antibodies" as used herein include polyclonal, monoclonal, single chain, chimeric, humanized and human antibodies, prepared according to conventional methodology.

"Cytokine" is a generic term for nonantibody soluble proteins which are released from one cell subpopulation and which act as intercellular mediators, for example, in the generation or regulation of an immune response. See Human Cytokines: Handbook for Basic & Clinical Research (Agrawal, et al. eds., Blackwell Scientific, Boston, Mass. 1991) (which is hereby incorporated by reference in its entirety for all purposes).

"CXCR4/SDF-1 antagonist" refers to a compound that antagonizes SDF-1 binding to CXCR4.

By "fugetactic activity" it is meant the ability of an agent to repel (or chemorepel) a eukaryotic cell with migratory capacity (i.e., a cell that can move away from a repellant stimulus). Accordingly, an agent with fugetactic activity is a "fugetactic agent." Such activity can be detected using any of the transmigration systems described herein (see Examples), or a variety of other systems well known in the art (see, e.g., U.S. Pat. No. 5,514,555, entitled: "Assays and therapeutic methods based on lymphocyte chemoattractants," issued May 7, 1996, to Springer, T A, et al.). A preferred system for use herein is described in U.S. Pat. No. 6,448,054 by Poznansky et al., which is incorporated herein by reference in its entirety.

"Immune cells" as used herein are cells of hematopoietic origin (see later discussion), that are involved in the specific recognition of antigens. Immune cells include antigen presenting cells (APCs), such as dendritic cells or macrophages, B cells, T cells, etc. "Mature T cells" as used herein include T cells of a $CD4^{lo}$ $CD8^{hi}$ CD69+ TCR+, $CD4^{hi}$ $CD8^{lo}$ CD69+ TCR+, CD4+ CD3+ RO+ and/or CD8+ CD3+ RO+ phenotype. The fugetactic response of the mature T cells to the compounds of the invention can be measured as described above, or according to the transmigration assays described in greater detail in the U.S. Pat. No. 6,448,054. Other suitable methods will be known to one of ordinary skill in the art and can be employed using only routine experimentation.

As used herein, a "subject" is a human, non-human primate, cow, horse, pig, sheep, goat, dog, cat or rodent. In all embodiments, human subjects are preferred.

II. Compositions and Methods of the Invention

The present invention is based, in part, upon the appreciation that dimerization of a G protein coupled receptor and/or receptor ligand is important for imparting fugetactic activity. Without being bound by theory, it is believed that these receptor ligands and/or the receptors dimerize to activate fugetaxis. Thus, the invention relates to fugetactic compounds which comprise ligand dimers, functional fragments and derivatives thereof and methods of inducing fugetaxis by contacting such compounds with a cell which expresses the corresponding G protein coupled receptor. The invention further relates to anti-fugetactic compounds which modulate the fugetactic effect of such G protein coupled receptors and/or receptor ligands, for example, by inhibiting ligand and/or receptor dimerization.

The invention involves polypeptides of numerous size and type that bind specifically to chemokine G protein coupled receptors (CXCR-4 and the like) and the binding partners thereof (chemokines (e.g., SDF-1 and IL-8). Cytokines include, e.g., interleukins IL-1 through IL-15, tumor necrosis factors alpha and beta, interferons alpha, beta, and gamma, tumor growth factor beta (TGF-β), colony stimulating factor (CSF) and granulocyte monocyte colony stimulating factor (GM-CSF). SDF-1α is a cytokine (chemokine) produced by thymic and bone marrow stroma (References 12-15 and U.S. Pat. No. 5,756,084, entitled: "Human stromal derived factor 1α and 1β," issued May 26, 1998, to Honjo, et al.), that has been reported as a highly efficacious and highly potent lymphocyte chemoattractant at concentrations lower than about 100 ng/ml.

The action of each cytokine on its target cell is mediated through binding to a cell surface receptor. Cytokines share many properties of hormones, but are distinct from classical hormones in that in vivo, they generally act locally on neighboring cells within a tissue. The activities of cytokines range from promoting cell growth (e.g., IL-2, IL-4, and IL-7), and arresting growth (IL-10, tumor necrosis factor and TGF-β), to inducing viral resistance (IFN α, β, and γ). See Fundamental Immunology (Paul ed., Raven Press, 2nd ed. 1989): Encyclopedia of Immunology. (Roitt ed., Academic Press 1992) (which are hereby incorporated by reference in their entirety for all purposes). In certain embodiments, the cytokine is a cytokine with chemoattractant and/or chemokinetic properties. Examples of such cytokines include: PAF, N-formylated peptides, C5a, LTB$_4$, LXA$_4$, chemokines: CXC, IL-8, GCP-2, GROα, GROβ, GROγ, ENA-78, NAP-2, IP-10, MIG, I-TAC, SDF-1α, BCA-1, PF4, Bolekine, MIP-1α, MIP-1β, RANTES, HCC-1, MCP-1, MCP-2, MCP-3, MCP-4, MCP-5 (mouse only), Leukotactin-1 (HCC-2, MIP-5), Eotaxin, Eotaxin-2 (MPIF2), Eotaxin-3 (TSC), MDC, TARC, SLC (Exodus-2, 6CKine), MIP-3α (LARC, Exodus-1), ELC (MIP-3β), I-309, DC-CK1 (PARC, AMAC-1), TECK, CTAK, MPIF1 (MIP-3), MIP-5 (HCC-2), HCC-4 (NCC-4), MIP-1γ (mouse only), C-10 (mouse only); C: Lymphotactin; CX$_3$ C: Fracktelkine (Neurotactin). More preferably, the cytokine is a member of the Cys-X-Cys family of chemokines (chemokines that bind to the CXCR-4 receptor). Preferred such agents of the invention include SDF-1α, SDF-1β, and met-SDF-1β. In further preferred embodiments, such fugetactic agents include other CXCR-4 receptor ligands. CXCR-4 ligands include, but are not limited to, HIV-1$_{IIIB}$ gp120, small molecules T134, and/or T22 ([Tyr5,12,Lys7]-polyphemusin II) (Heveker et al., Curr Biol, 1998, 8:369-76).

The polypeptides of the invention, including dimers thereof and polypeptides that modulate dimerization, may be derived from sources known in the art, such as peptide libraries. Such polypeptides can be provided by degenerate peptide libraries which can be readily prepared in solution, in immobilized form or as phage display libraries. Libraries further can be synthesized of peptides and non-peptide synthetic moieties.

Standard recombinant techniques can also be used to produce polypeptides of the invention. The practice of the present invention employs, unless otherwise indicated, conventional techniques of molecular biology (including recombinant techniques), microbiology, cell biology, biochemistry and immunology, which are within the skill of the art. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology", "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polypeptides of the invention, and, as such, may be considered in making and practicing the invention.

According to one aspect of the invention fugetactic compounds described herein can be used to achieve a therapeutic result in a subject. In one embodiment, a method of inhibiting migration of immune cells to a specific site in a subject is provided. The method involves locally administering to a specific site in a subject in need of such treatment a fugetactic agent described herein in an amount effective to inhibit migration of immune cells to the specific site in a subject.

Thus, the invention provides a method of inhibiting migration of immune cells to a site of inflammation in the subject, "inflammation" as used herein, is a localized protective response elicited by a foreign (non-self) antigen, and/or by an injury or destruction of tissue(s), which serves to destroy, dilute or sequester the foreign antigen, the injurious agent, and/or the injured tissue. Inflammation occurs when tissues are injured by viruses, bacteria, trauma, chemicals, heat, cold, or any other harmful stimuli. In such instances, the classic weapons of the immune system (T cells, B cells, macrophages) interface with cells and soluble products that are mediators of inflammatory responses (neutrophils, eosinophils, basophils, kinin and coagulation systems, and complement cascade).

A typical inflammatory response is characterized by (i) migration of leukocytes at the site of antigen (injury) localization; (ii) specific and nonspecific recognition of "foreign" and other (necrotic/injured tissue) antigens mediated by B and T lymphocytes, macrophages and the alternative complement pathway; (iii) amplification of the inflammatory response with the recruitment of specific and nonspecific effector cells by complement components, lymphokines and monokines, kinins, arachidonic acid metabolites, and mast cell/basophil products; and (iv) macrophage, neutrophil and lymphocyte participation in antigen destruction with ultimate removal of antigen particles (injured tissue) by phagocytosis. The ability of the immune system to discriminate between "self" and "non-self" (foreign) antigens is therefore vital to the functioning of the immune system as a specific defense against non-self antigens.

Non-self antigens are those antigens on substances entering a subject, or exist in a subject but are detectably different or foreign from the subject's own constituents, whereas self antigens are those which, in the healthy subject, are not detectably different or foreign from its constituents.

In another important embodiment, the inflammation is caused by an immune response against self-antigen, and the subject in need of treatment according to the invention has an autoimmune disease. Autoimmune disease as used herein, results when a subject's immune system attacks its own organs or tissues, producing a clinical condition associated with the destruction of that tissue, as exemplified by diseases such as rheumatoid arthritis, uveitis. insulin-dependent diabetes mellitus, hemolytic anemias, rheumatic fever, Crohn's disease. Guillain-Bane syndrome, psoriasis, thyroiditis, Graves' disease, myasthenia gravis. glomerulonephritis, autoimmune hepatitis, multiple sclerosis, systemic lupus erythematosus, etc.

Autoimmune disease may be caused by a genetic predisposition alone, by certain exogenous agents (e.g., viruses, bacteria, chemical agents, etc.), or both. Some forms of autoimmunity arise as the result of trauma to an area usually not exposed to lymphocytes, such as neural tissue or the lens of the eye. When the tissues in these areas become exposed to lymphocytes, their surface proteins can act as antigens and trigger the production of antibodies and cellular immune responses which then begin to destroy those tissues. Other autoimmune diseases develop after exposure of a subject to antigens which are antigenically similar to, that is cross-reactive with, the subject's own tissue. In rheumatic fever, for example, an antigen of the streptococcal bacterium, which causes rheumatic fever, is cross-reactive with parts of the human heart. The antibodies cannot differentiate between the bacterial antigens and the heart muscle antigens, consequently cells with either of those antigens can be destroyed.

Other autoimmune diseases, for example, insulin-dependent diabetes mellitus (involving the destruction of the insulin producing beta-cells of the islets of Langerhans), multiple sclerosis (involving the destruction of the conducting fibers of the nervous system) and rheumatoid arthritis (involving the destruction of the joint-lining tissue), are characterized as being the result of a mostly cell-mediated autoimmune response and appear to be due primarily to the action of T cells (See, Sinha et al., Science, 1990, 248:1380). Yet others, such as myesthenia gravis and systemic lupus erythematosus, are characterized as being the result of primarily a humoral autoimmune response. Nevertheless, inhibition of migration of immune cells to a specific site of inflammation involved in any of the foregoing conditions according to the invention, is beneficial to the subject since it inhibits escalation of the inflammatory response, protecting the specific site (e.g., tissue) involved, from "self-damage." In preferred embodiments, the subject has rheumatoid arthritis, multiple sclerosis, or uveitis.

In a further important embodiments, the inflammation is caused by an immune response against non-self-antigens (including antigens of necrotic self-material), and the subject in need of treatment according to the invention is a transplant recipient, has atherosclerosis, has suffered a myocardial infarction and/or an ischemic stroke, has an abscess, and/or has myocarditis. This is because after cell (or organ) transplantation, or after myocardial infarction or ischemic stroke, certain antigens from the transplanted cells (organs), or necrotic cells from the heart or the brain, can stimulate the production of immune lymphocytes and/or autoantibodies, which later participate in inflammation/rejection (in the case of a transplant), or attack cardiac or brain target cells causing inflammation and aggravating the condition (Johnson et al., Sem. Nuc. Med. 1989, 19:238: Leinonen et al., Microbiol. Path., 1990, 9:67; Montalban et al., Stroke, 1991, 22:750).

According to another aspect of the invention, a method of inhibiting endothelial cell migration to a tumor site in a subject, is provided. The method involves locally administering to an area surrounding a tumor site in a subject in need of such treatment a fugetactic agent described herein in an amount effective to inhibit endothelial cell migration to the tumor site in the subject. In certain embodiments, the area surrounding the tumor site is not immediate to the tumor site. Important fugetactic agents are as described above.

According to another aspect of the invention, a method of treating infertility and premature labor, including premature delivery and impending miscarriage, is provided. The method involves administering to a subject in need of such treatment a fugetactic agent described herein in an amount effective to inhibit immune cells from migrating close to a germ cell (including an egg, a sperm, a fertilized egg, or an implanted embryo) in the subject. A germ cell is a cell specialized to produce haploid gametes. It is a cell further differentiated than a stem cell, that can still give rise to more differentiated germ-line cells. In further embodiments, the administration is local to a germ cell-containing site of the subject. The foregoing methods of therapy may include co-administration of a non-fugetactic agent together with a fugetactic agent of the invention that can act cooperatively, additively, or synergistically with the fugetactic agent of the invention to inhibit migration of immune cells to the site of inflammation in the subject. According to some embodiments, a fugetactic agent is administered substantially simultaneously with a non-fugetactic agent to inhibit migration of immune cells to a site of inflammation. By substantially simultaneously, it is meant that the fugetactic agent is locally administered to the subject close enough in time with the administration of the non-fugetactic agent, whereby the non-fugetactic agent may exert a potentiating effect on migration inhibiting activity of the fugetactic agent. Thus, by substantially simultaneously it is meant that the fugetactic agent is administered before, at the same time, and/or after the administration of the non-fugetactic agent. The fugetactic agent can be administered as a polypeptide, and/or a nucleic acid which expresses a fugetactic agent.

In certain embodiments, the non-fugetactic agents are immunosuppressants. Such immunosuppressants include: Azathioprine; Azathioprine Sodium: Cyclosporine; Daltroban; Gusperimus Trihydrochloride; Sirolimus; Tacrolimus.

In other embodiments, the non-fugetactic agents are anti-inflammatory agents. Such anti-inflammatory agents include: Alclofenac; Alclometasone Dipropionate; Algestone Acetonide; Alpha Amylase; Amcinafal; Amcinafide; Amfenac Sodium; Amiprilose Hydrochloride; Anakinra; Anirolac; Anitrazafen; Apazone; Balsalazide Disodium; Bendazac; Benoxaprofen; Benzydamine Hydrochloride; Bromelains; Broperamole; Budesonide; Carprofen; Cicloprofen; Cintazone; Cliprofen; Clobetasol Propionate; Clobetasone Butyrate; Clopirac; Cloticasone Propionate; Cormethasone Acetate; Cortodoxone; Deflazacort; Desonide; Desoximetasone; Dexamethasone Dipropionate; Diclofenac Potassium; Diclofenac Sodium; Diflorasone Diacetate; Diflumidone Sodium; Diflunisal; Difluprednate; Diftalone; Dimethyl Sulfoxide; Drocinonide; Endrysone; Enlimomab; Enolicam Sodium; Epirizole; Etodolac; Etofenamate; Felbinac; Fenamole; Fenbufen; Fenclofenac; Fenclorac; Fendosal; Fenpipalone; Fentiazac; Flazalone; Fluazacort; Flufenamic Acid; Flumizole; Flunisolide Acetate; Flunixin; Flunixin Meglumine; Fluocortin Butyl; Fluorometholone Acetate; Fluquazone; Flurbiprofen; Fluretofen; Fluticasone Propionate; Furaprofen; Furobufen; Halcinonide; Halobetasol Propionate; Halopredone Acetate; Ibufenac; Ibuprofen; Ibuprofen Aluminum; Ibuprofen Piconol; Ilonidap; Indomethacin; Indomethacin Sodium; Indoprofen; Indoxole; Intrazole; Isoflupredone Acetate; Isoxepac; Isoxicam; Ketoprofen; Lofemizole Hydrochloride; Lornoxicam; Loteprednol Etabonate; Meclofenamate Sodium; Meclofenamic Acid; Meclorisone Dibutyrate; Mefenamic Acid; Mesalamine; Meseclazone; Methylprednisolone Suleptanate; Morniflumate; Nabumetone; Naproxen; Naproxen Sodium; Naproxol; Nimazone; Olsalazine Sodium; Orgotein; Orpanoxin; Oxaprozin; Oxyphenbutazone; Paranyline Hydrochloride; Pentosan Polysulfate Sodium; Phenbutazone Sodium Glycerate; Pirfenidone; Piroxicam; Piroxicam Cinnamate; Piroxicam Olamine; Pirprofen; Prednazate; Prifelone; Prodolic Acid; Proquazone; Proxazole; Proxazole Citrate; Rimexolone; Romazarit; Salcolex; Salnacedin; Salsalate; Sanguinarium Chloride; Seclazone; Sermetacin; Sudoxicam; Sulindac; Suprofen; Talmetacin; Talniflumate; Talosalate; Tebufelone; Tenidap; Tenidap Sodium; Tenoxicam; Tesicam; Tesimide; Tetrydamine; Tiopinac; Tixocortol Pivalate; Tolmetin; Tolmetin Sodium; Triclonide; Triflumidate; Zidometacin; Zomepirac Sodium.

According to another aspect, the invention involves a method of repelling immune cells from a material surface. "Material surfaces" as used herein, include, but are not limited to, dental and orthopedic prosthetic implants, artificial valves, and organic implantable tissue such as a stent, allogeneic and/or xenogeneic tissue, organ and/or vasculature.

Implantable prosthetic devices have been used in the surgical repair or replacement of internal tissue for many years. Orthopedic implants include a wide variety of devices, each suited to fulfill particular medical needs. Examples of such devices are hip joint replacement devices, knee joint replacement devices, shoulder joint replacement devices, and pins, braces and plates used to set fractured bones. Some contemporary orthopedic and dental implants, use high performance metals such as cobalt-chrome and titanium alloy to achieve high strength. These materials are readily fabricated into the complex shapes typical of these devices using mature metal working techniques including casting and machining.

The material surface is coated with an amount of a fugetactic agent described herein effective to repel immune cells. In important embodiments, the material surface is part of an implant. In important embodiments, in addition to a fugetactic agent, the material surface may also be coated with a cell-growth potentiating agent, an anti-infective agent, and/or an antiinflammatory agent. A cell-growth potentiating agent as used herein is an agent which stimulates growth of a cell and includes growth factors such as PDGF, EGF, FGF, TGF, NGF, CNTF, and GDNF.

According to another aspect of the invention, a method of identifying a fugetactic agent, is provided. The method involves contacting an agent suspected of being a fugetactic agent with a cell with migratory capacity, measuring the zone of clearance relative to the cell; and determining that the zone of clearance is of a sufficient size to thereby identify the fugetactic agent. In certain embodiments, the cell with migratory capacity is a hematopoietic cell, a neural cell, an epithelial cell, a mesenchymal cell, an embryonic stem cell or a germ cell.

Cells of hematopoietic origin include, but are not limited to, pluripotent stem cells, multipotent progenitor cells and/or progenitor cells committed to specific hematopoietic lineages. The progenitor cells committed to specific hematopoietic lineages may be of T cell lineage, B cell lineage, dendritic cell lineage, Langerhans cell lineage and/or lymphoid tissue-specific macrophage cell lineage. The hematopoietic cells may be derived from a tissue such as bone marrow, peripheral blood (including mobilized peripheral blood), umbilical cord blood, placental blood, fetal liver, embryonic cells (including embryonic stem cells), aortal-gonadal-mesonephros derived cells, and lymphoid soft tissue. Lymphoid soft tissue includes the thymus, spleen, liver, lymph node, skin, tonsil and Peyer's patches. In other embodiments, the "hematopoietic origin" cells may be derived from in vitro cultures of any of the foregoing cells, and in particular in vitro cultures of progenitor cells.

Cells of neural origin, include neurons and glia, and/or cells of both central and peripheral nervous tissue that express RR/B (sec, U.S. Pat. No. 5,863,744, entitled: "Neural cell protein marker RR/B and DNA encoding same," issued Jan. 26, 1999, to Avraham, et al.).

Cells of epithelial origin, include cells of a tissue that covers and lines the free surfaces of the body. Such epithelial tissue includes cells of the skin and sensory organs, as well as the specialized cells lining the blood vessels, gastrointestinal tract, air passages, ducts of the kidneys and endocrine organs.

Cells of mesenchymal origin include cells that express typical fibroblast markers such as collagen, vimentin and fibronectin.

An embryonic stem cell is a cell that can give rise to cells of all lineages; it also has the capacity to self-renew.

According to yet another aspect of the invention, an anti-fugetactic agent is provided. In one embodiment, the anti-fugetactic agent is any agent that inhibits chemokine and/or chemokine receptor dimerization. Chemokines act as monomers on chemokine receptors at concentrations below 100 nM, thereby functioning as chemoattractants. Certain chemokines, including IL-8 and SDF-1 can also serve as chemorepellents at high concentrations (e.g., above 100 nM) where much of the chemokine exists as a dimer. Dimerization of the chemokine elicits a differential response in cells, causing dimerization of chemokine receptors, an activity which is interpreted as a chemorepellent signal. Thus, binding of the dimeric chemokine and dimerization of the cognate chemokine receptor on the cell surface can elicit a differential signal in the cell, including an increased calcium flux and concomitant alterations of secondary messenger molecules, to thereby induce fugetaxis.

Anti-fugetactic agents therefore include any agents that specifically inhibit chemokine and/or chemokine receptor dimerization, thereby blocking the chemorepellent response to a fugetactic agent. Blocking the chemorepellent effect of high concentrations of a chemokine secreted by a tumor can be accomplished by anti-fugetactic agents which inhibit chemokine dimer formation or chemokine receptor dimer formation. For example, antibodies that target and block chemokine receptor dimerization, for example, by interfering with the dimerization domains or ligand binding can be anti-fugetactic agents. Where desired, this effect can be achieved without inhibiting the chemotactic action of monomeric chemokine.

In other embodiments, the anti-fugetactic agent is a CXCR4 antagonist, CXCR3 antagonist, CXCR4/SDF-1 antagonist or selective PKC inhibitor.

Anti-fugetactic agents of the invention can be but are not limited to CXCR4 antagonists, CXCR3 antagonists, CXCR4/SDF-1 antagonists or selective PKC inhibitors.

The CXCR4 antagonist can be but is not limited to AMD3100 (Proc Natl Acad Sci USA. 2003; 100(23):13513-8), KRH-1636 (Proc Natl Acad Sci USA. 2003; 100(7): 4185-90), T-20 (Org Biomol Chem. 2004; 2(5):660-4), T-22 (J Med. Virol. 2002 October; 68(2):147-55), T-140 (FEBS Lett. 2003; 550(1-3):79-83; Curr Drug Targets Infect Disord. 2004; 4(2):103-10), TE-14011 (Biochem Biophys Res Commun. 2004; 320(1):226-32), T-14012 (Curr Opin Investig Drugs. 2001; 2(9):1198-202), or TN14003 (FEBS Lett. 2004; 569(1-3):99-104; Cancer Res. 2004; 64(12):4302-8) or an antibody that interferes with the dimerization of CXCR4.

The CXCR3 antagonist can be but is not limited to TAK-779 (J Leukoc Biol. 2003; 73(2):273-80), AK602 (J. Virol. 2004; 78(16):8654-62), or SCH-351125 (J. Virol. 2004; 78(8):4134-44; J. Virol. 2003; 77(9):5201-8) or an antibody that interferes with the dimerization of CXCR3.

The CXCR4/SDF-1 antagonist can be but is not limited to Tannic acid (Clin Cancer Res. 2003; 9(8):3115-23), NSC 651016 or (Clin Cancer Res. 2002; 8(12):3955-60) or an antibody that interferes with the dimerization of CXCR4 and/or SDF-1.

The selective PKC inhibitor can be but is not limited to thalidomide or GF109230X (J Biol Chem 1991; 266:15771-81).

The invention may also provide an anti-fugetactic compound, such as an anti-cytokine or cytokine receptor antibody. Various kinds of antibodies, and methods for their production are well known in the air. Thus, anti-cytokine or cytokine receptor antibodies of the invention may comprise a fragmented or unfragmented antibody that recognizes an epitopic region on a cytokine of interest. As is well-known in the art, only a small portion of an antibody molecule, the paratope, is involved in the binding of the antibody to its epitope (see, in general, Clark, W. R. (1986) The Experimental Foundations of Modern Immunology Wiley & Sons. Inc., New York; Roitt, I. (1991) Essential Immunology, 7th Ed., Blackwell Scientific Publications, Oxford). The pFc' and Fc regions, for example, are effectors of the complement cascade but are not involved in antigen binding. An antibody from which the pFc' region has been enzymatically cleaved, or which has been produced without the pFc' region, designated an F(ab')$_2$ fragment, retains both of the antigen binding sites of an intact antibody. Similarly, an antibody from which the Fc region has been enzymatically cleaved, or which has been produced without the Fc region, designated an Fab fragment, retains one of the antigen binding sites of an intact antibody molecule. Proceeding further, Fab fragments consist of a covalently bound antibody light chain and a portion of the antibody heavy chain denoted Fd. The Fd fragments are the major determinant of antibody specificity (a single Fd fragment may be associated with up to ten different light chains without altering antibody specificity) and Fd fragments retain epitope-binding ability in isolation.

Within the antigen-binding portion of an antibody, as is well-known in the art, there are complementarity determining regions (CDRs), which directly interact with the epitope of the antigen, and framework regions (FRs), which maintain the tertiary structure of the paratope (see, in general, Clark, 1986; Roitt, 1991). In both the heavy chain Fd fragment and the light chain of IgG immunoglobulins, there are four framework regions (FR1 through FR4) separated respectively by three complementarity determining regions (CDR1 through CDR3). The CDRs, and in particular the CDR3 regions, and more particularly the heavy chain CDR3, are largely responsible for antibody specificity.

It is now well-established in the art that the non-CDR regions of a mammalian antibody may be replaced with similar regions of conspecific or heterospecific antibodies while retaining the epitopic specificity of the original antibody. This is most clearly manifested in the development and use of "humanized" antibodies in which non-human CDRs are covalently joined to human FR and/or Fc/pFc' regions to produce a functional antibody. Thus, for example, PCT International Publication Number WO 92/04381 teaches the production and use of humanized murine RSV antibodies in which at least a portion of the murine FR regions have been replaced by FR regions of human origin. Such antibodies, including fragments of intact antibodies with antigen-binding ability, are often referred to as "chimeric" antibodies.

Thus, as will be apparent to one of ordinary skill in the art, the present invention also provides for F(ab')$_2$, Fab, Fv and Fd fragments; chimeric antibodies in which the Fc and/or FR and/or CDR1 and/or CDR2 and/or light chain CDR3 regions have been replaced by homologous human or non-human sequences; chimeric F(ab')$_2$ fragment antibodies in which the FR and/or CDR1 and/or CDR2 and/or light chain CDR3 regions have been replaced by homologous human or non-human sequences; chimeric Fab fragment antibodies in which the FR and/or CDR1 and/or CDR2 and/or light chain CDR3 regions have been replaced by homologous human or non-human sequences; and chimeric Fd fragment antibodies in which the FR and/or CDR1 and/or CDR2 regions have been replaced by homologous human or non-human sequences.

In yet another aspect, the invention further relates to methods of modulating fugetactis to provide a therapeutic response in a subject. Thus, a method of enhancing an immune response in a subject having a condition that involves a specific site, is provided. The method involves locally administering to a specific site in a subject in need of such treatment an anti-fugetactic agent in an amount effective to inhibit immune cell-specific fugetactic activity at a specific site in the subject. In some embodiments, the specific site is a site of a pathogenic infection. Efficient recruitment of immune cells to help eliminate the infection is therefore beneficial.

Infection can result from exposure to infectious pathogens. Pathogens include, for example, viruses, bacteria, parasites, and fungi.

Examples of viruses that have been found in humans include but are not limited to: Retroviridae (e.g. human immunodeficiency viruses, such as HIV-1 (also referred to as HDTV-III, LAVE or HTLV-III/LAV, or HIV-III; and other isolates, such as HIV-LP; Picornaviridae (e.g. polio viruses, hepatitis A virus; enteroviruses, human Coxsackie viruses, rhinoviruses, echoviruses); Calciviridae (e.g. strains that cause gastroenteritis); Togaviridae (e.g. equine encephalitis viruses, rubella viruses); Flaviridae (e.g. dengue viruses, encephalitis viruses, yellow fever viruses); Coronoviridae (e.g. coronaviruses); Rhabdoviridae (e.g. vesicular stomatitis viruses, rabies viruses); Filoviridae (e.g. ebola viruses); Paramyxoviridae (e.g. parainfluenza viruses, mumps virus, measles virus, respiratory syncytial virus); Orthomyxoviridae (e.g. influenza viruses); Bungaviridae (e.g. Hantaan viruses, bunga viruses, phleboviruses and Nairo viruses); Arena viridae (hemorrhagic fever viruses); Reoviridae (e.g. reoviruses, orbiviruses and rotaviruses); Birnaviridae; Hepadnaviridae (Hepatitis B virus); Parvovirida (parvoviruses); Papovaviridae (papilloma viruses, polyoma viruses); Adenoviridae (most adenoviruses); Herpesviridae (herpes simplex virus (HSV) 1 and 2, varicella zoster virus, cytomegalovirus (CMV), herpes virus; Poxyviridae (variola viruses, vaccinia viruses, pox viruses); and Iridoviridae (e.g. African swine fever virus); and unclassified viruses (e.g. the agent of delta hepatitis (thought to be a defective satellite of hepatitis B virus), the agents of non-A, non-B hepatitis (class 1=internally transmitted; class 2=parenterally transmitted (i.e. Hepatitis C); Norwalk and related viruses, and astroviruses).

Both gram negative and gram positive bacteria serve as antigens in vertebrate animals. Such gram positive bacteria include, but are not limited to, *Pasteurella* species, *Staphylococci* species, and *Streptococcus* species. Gram negative bacteria include, but are not limited to, *Escherichia coli, Pseudomonas* species, and *Salmonella* species. Specific examples of infectious bacteria include but are not limited to, *Helicobacter pyloris, Borelia burgdorferi, Legionella pneumophilia, Mycobacteria* sps (e.g. *M. tuberculosis, M. avium, M. intracellulare, M. kansaii, M. gordonae*), *Staphylococcus aureus, Neisseria gonorrhoeae, Neisseria meningitidis, Listeria monocytogenes, Streptococcus pyogenes* (Group A *Streptococcus*), *Streptococcus agalactiae* (Group B *Streptococcus*), *Streptococcus* (viridans group), *Streptococcus faecalis, Streptococcus bovis, Streptococcus* (anaerobic sps.), *Streptococcus pneumoniae*, pathogenic *Campylobacter* sp., *Enterococcus* sp., *Haemophilus influenzae, Bacillus antracis, corynebacterium diphtheriae, corynebacterium* sp., *Erysipelothrix rhusiopathiae, Clostridium perfringers, Clostridium tetani, Enterobacter aerogenes, Klebsiella pneumoniae, Pasturella multocida, Bacteroides* sp., *Fusobacterium nucleatum, Streptobacillus moniliformis, Treponema pallidium, Treponema pertenue, Leptospira, Rickettsia*, and *Actinomyces israelli*.

Examples of fungi include *Cryptococcus neoformans, Histoplasma capsulatum, Coccidioides immitis, Blastomyces dermatitidis, Chlamydia trachomatis, Candida albicans.*

Other infectious organisms (i.e., protists) include *Plasmodium* spp. such as *Plasmodium falciparum, Plasmodium malariae, Plasmodium ovale,* and *Plasmodium vivax* and *Toxoplasma gondii.* Blood-borne and/or tissues parasites include *Plasmodium* spp., *Babesia microti, Babesia divergens, Leishmania tropica, Leishmania* spp., *Leishmania braziliensis, Leishmania donovani, Trypanosoma gambiense* and *Trypanosoma rhodesiense* (African sleeping sickness), *Trypanosoma cruzi* (Chagas' disease), and *Toxoplasma gondii.*

Other medically relevant microorganisms have been described extensively in the literature, e.g., see C. G. A Thomas, *Medical Microbiology*, Bailliere Tindall, Great Britain 1983, the entire contents of which is hereby incorporated by reference.

In certain embodiments, the specific site is a germ cell containing site. In this case the recruitment of immune cells to these specific sites will help eliminate unwanted germ cells, and/or implanted and non-implanted embryos. In further embodiments, co-administration of contraceptive agents other than anti-fugetactic agents is also provided. Non-anti-fugetactic contraceptive agents are well known in the art.

In further embodiments, the specific site is an area immediately surrounding a cancer or tumor. Since most of the known tumors escape immune recognition, it is beneficial to enhance the migration of immune cells to the tumor site.

Cancers or tumors include biliary tract cancer; brain cancer, including glioblastomas and medulloblastomas; breast cancer; cervical cancer; choriocarcinoma; colon cancer; endometrial cancer; esophageal cancer; gastric cancer; hematological neoplasms, including acute lymphocytic and myelogenous leukemia; multiple myeloma; AIDS associated leukemias and adult T-cell leukemia lymphoma; intraepithelial neoplasms, including Bowen's disease and Paget's disease; liver cancer (hepatocarcinoma); lung cancer; lymphomas, including Hodgkin's disease and lymphocytic lymphomas; neuroblastomas; oral cancer, including squamous cell carcinoma; ovarian cancer, including those arising from epithelial cells, stromal cells, germ cells and mesenchymal cells; pancreas cancer; prostate cancer; rectal cancer; sarcomas, including leiomyosarcoma, rhabdomyosarcoma, liposarcoma, fibrosarcoma and osteosarcoma; skin cancer, including melanoma, Kaposi's sarcoma, basocellular cancer and squamous cell cancer; testicular cancer, including germinal tumors (seminoma, non-seminoma[teratomas, choriocarcinomas]), stromal tumors and germ cell tumors; thyroid cancer, including thyroid adenocarcinoma and medullar carcinoma; and renal cancer including adenocarcinoma and Wilms tumor. In important embodiments, cancers or tumors escaping immune recognition include glioma, colon carcinoma, colorectal cancer, lymphoid cell-derived leukemia, choriocarcinoma, and melanoma.

In further embodiments, co-administration of anti-cancer agents other than anti-fugetactic agents is also provided. Non-anti-fugetactic anti-cancer agents include: Acivicin; Aclarubicin; Acodazole Hydrochloride; Acronine; Adozelesin; Aldesleukin; Altretamine; Ambomycin; Ametantrone Acetate; Aminoglutethimide; Amsacrine; Anastrozole; Anthramycin; Asparaginase; Asperlin; Azacitidine; Azetepa; Azotomycin; Batimastat; Benzodepa; Bicalutamide; Bisantrene Hydrochloride; Bisnafide Dimesylate; Bizelesin; Bleomycin Sulfate; Brequinar Sodium; Bropirimine; Busulfan; Cactinomycin; Calusterone; Caracemide; Carbetimer; Carboplatin; Carmustine; Carubicin Hydrochloride; Carzelesin; Cedefingol; Chlorambucil; Cirolemycin; Cisplatin; Cladribine; Crisnatol Mesylate; Cyclophosphamide; Cytarabine; Dacarbazine; Dactinomycin; Daunorubicin Hydrochloride; Decitabine; Dexormaplatin; Dezaguanine; Dezaguanine Mesylate; Diaziquone; Docetaxel; Doxorubicin; Doxorubicin Hydrochloride; Droloxifene; Droloxifene Citrate; Dromostanolone Propionate; Duazomycin; Edatrexate; Eflornithine Hydrochloride; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Etoposide; Etoposide Phosphate; Etoprine; Fadrozole Hydrochloride; Fazarabine; Fenretinide; Floxuridine; Fludarabine Phosphate; Fluorouracil; Fluorocitabine; Fosquidone; Fostriecin Sodium; Gemcitabine; Gemcitabine Hydrochloride; Hydroxyurea; Idarubicin Hydrochloride; Ifosfamide; Ilmofosine; Interferon Alfa-2a; Interferon Alfa-2b; Interferon Alfa-n1; Interferon Alfa-n3; Interferon Beta-I a; Interferon Gamma-I b; Iproplatini; Irinotecan Hydrochloride; Lanreotide Acetate; Letrozole; Leuprolide Acetate; Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Metoprine; Meturedepa; Mitindomide; Mitocarcin; Mitocromin; Mitogillin; Mitomalcin; Mitomycin; Mitosper; Mitotane; Mitoxantrone Hydrochloride; Mycophenolic Acid; Nocodazole; Nogalamycin; Ormaplatin; Oxisuran; Paclitaxel; Pegaspargase; Peliomycin; Pentamustine; Peplomycin Sulfate; Perfosfamide; Pipobroman; Piposulfan; Piroxantrone Hydrochloride; Plicamycin; Plomestane; Podofilox; Porfimer Sodium; Porfiromycin; Prednimustine; Procarbazine Hydrochloride; Puromycin; Puromycin Hydrochloride; Pyrazofurin; Riboprine; Rogletimide; Safingol; Safingol Hydrochloride; Semustine; Simtrazene; Sparfosate Sodium; Sparsomycin; Spirogermanium Hydrochloride; Spiromustine; Spiroplatin; Streptonigrin; Streptozocin; Sulofenur; Talisomycin; Taxotere; Tecogalan Sodium; Tegafur, Teloxantrone Hydrochloride; Temoporfin; Teniposide; Teroxirone; Testolactone; Thiamiprine; Thioguanine; Thiotepa; Tiazofurin; Tirapazamine; Topotecan Hydrochloride; Toremifene Citrate; Trestolone Acetate; Triciribine Phosphate; Trimetrexate; Trimetrexate Glucuronate; Triptorelin; Tubulozole Hydrochloride; Uracil Mustard; Uredepa; Vapreotide; Verteporlin; Vinblastine Sulfate; Vincristine Sulfate; Vindesine; Vindesine Sulfate; Vinepidine Sulfate; Vinglycinate Sulfate; Vinleurosine Sulfate; Vinorelbine Tartrate Virlrosidine Sulfate; Vinzolidine Sulfate; Vorozole; Zeniplatin; Zinostatin; Zorubicin Hydrochloride.

According to a further aspect of the invention, a method of inhibiting tumor cell metastasis in a subject is provided. The method involves locally administering to a tumor site in a subject in need of such treatment an anti-fugetactic agent in an amount effective to inhibit metastasis of tumor cells from the tumor site in the subject. In certain embodiments, the anti-fugetactic agent is a cytokine dimer. In other embodiments, the cytokine binding agent is an anti-cytokine antibody or a cytokine agonist. In a preferred embodiment the cytokine is SDF-1α. In further embodiments, co-administration of anti-cancer agents other than anti-fugetactic agents is also provided. Anti-cancer and anti-fugetactic agents are as described above.

Tumor cells move through tissues and away from the primary tumor as a result of chemokines released by adjacent tissues. Tumor cells metastasize to specific tissues releasing chemokines which bind the cognate chemokine receptors on the invading tumor cell. Tumor cells (as well as stromal tissues within the tumor itself) can produce high concentrations of chemokines that also cause chemorepulsion of tumor cells at the periphery of the tumor, resulting in both local invasion and metastasis. Anti-fugetactic agents of the invention can block the chemorepulsion of tumor cells, thereby reducing or preventing the invasion and metastasis that cause the spread of cancer.

According to a further aspect of the invention, a method of contraception in a subject, is provided. The method involves administering to a subject in need of such treatment, an anti-fugetactic agent in an amount effective to inhibit migration of germ cells in the subject. In certain embodiments, the anti-fugetactic agent is a cytokine binding agent. In some embodiments, the cytokine binding agent is an anti-cytokine antibody or a cytokine agonist. In a preferred embodiment the cytokine is SDF-1α. In further embodiments, the administration is local to a germ cell-containing site of the subject.

The compositions, as described above, are administered in effective amounts. The effective amount will depend upon the mode of administration, the particular condition being treated and the desired outcome. It will also depend upon, as discussed above, the stage of the condition, the age and physical condition of the subject, the nature of concurrent therapy, if any, and like factors well known to the medical practitioner. For therapeutic applications, it is that amount sufficient to achieve a medically desirable result. In some cases this is a local (site-specific) reduction of inflammation. In other cases, it is inhibition of tumor growth and/or metastasis.

Generally, doses of active compounds of the present invention would be from about 0.01 mg/kg per day to 1000 mg/kg per day. It is expected that doses ranging from 50-500 mg/kg will be suitable. A variety of administration routes are available. The methods of the invention, generally speaking may be practiced using any mode of administration that is medically acceptable, meaning any mode that produces effective levels of the active compounds without causing clinically unacceptable adverse effects. Such modes of administration include oral, rectal, topical, nasal, interdermal, or parenteral routes. The term "parenteral" includes subcutaneous, intravenous, intramuscular, or infusion. Intravenous or intramuscular routes are not particularly suitable for long-term therapy and prophylaxis. They could, however, be preferred in emergency situations. Oral administration will be preferred for prophylactic treatment because of the convenience to the patient as well as the dosing schedule. When peptides are used therapeutically, in certain embodiments a desirable route of administration is by pulmonary aerosol. Techniques for preparing aerosol delivery systems containing peptides are well known to those of skill in the art. Generally, such systems should utilize components which will not significantly impair the biological properties of the antibodies, such as the paratope binding capacity (see, for example, Sciarra and Cutie, "Aerosols," in Remington's Pharmaceutical Sciences, 18th edition, 1990, pp 1694-1712; incorporated by reference). Those of skill in the art can readily determine the various parameters and conditions for producing antibody or peptide aerosols without resort to undue experimentation.

Compositions suitable for oral administration may be presented as discrete units, such as capsules, tablets, lozenges, each containing a predetermined amount of the active agent. Other compositions include suspensions in aqueous liquids or non-aqueous liquids such as a syrup, elixir or an emulsion.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like. Lower doses will result from other forms of administration, such as intravenous administration. In the event that a response in a subject is insufficient at the initial doses applied, higher doses (or effectively higher doses by a different, more localized delivery route) may be employed to the extent that patient tolerance permits. Multiple doses per day are contemplated to achieve appropriate systemic levels of compounds.

The fugetactic agents, fugetactic binding agents, fragments thereof or and/or anti-fugetactic agents may be combined, optionally, with a pharmaceutically-acceptable carrier. The term "pharmaceutically-acceptable carrier" as used herein means one or more compatible solid or liquid filler, diluents or encapsulating substances which are suitable for administration into a human. The term "carrier" denotes an organic or inorganic ingredient, natural or synthetic, with which the active ingredient is combined to facilitate the application. The components of the pharmaceutical compositions also are capable of being co-mingled with the molecules of the present invention, and with each other, in a manner such that there is no interaction which would substantially impair the desired pharmaceutical efficacy.

The invention in other aspects includes pharmaceutical compositions of fugetactic agents and anti-fugetactic agents.

When administered, the pharmaceutical preparations of the invention are applied in pharmaceutically-acceptable amounts and in pharmaceutically-acceptably compositions. Such preparations may routinely contain salt, buffering agents, preservatives, compatible carriers, and optionally other therapeutic agents. When used in medicine, the salts should be pharmaceutically acceptable, but non-pharmaceutically acceptable salts may conveniently be used to prepare pharmaceutically-acceptable salts thereof and are not excluded from the scope of the invention. Such pharmacologically and pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts.

Fugetactic and/or anti-fugetactic molecules (nucleic acids or polypeptides) preferably are produced recombinantly, although such molecules may be isolated from biological extracts. Alternatively, direct administration of cells encoding fugetactic and/or anti-fugetactic agents is also contemplated.

Recombinantly produced fugetactic agents such as SDF-1α polypeptides, include chimeric proteins comprising a fusion of a SDF-1α protein with another polypeptide, e.g., a polypeptide capable of providing or enhancing protein-protein binding, sequence specific nucleic acid binding (such as GAL4), enhancing stability of the SDF-1α polypeptide under assay conditions, or providing a detectable moiety, such as green fluorescent protein. A polypeptide fused to a SDF-1α polypeptide or fragment may also provide means of readily detecting the fusion protein, e.g., by immunological recognition or by fluorescent labeling.

Various techniques may be employed for introducing nucleic acids of the invention (SDF-1α sense and anti-sense, dominant negative) into cells, depending on whether the nucleic acids are introduced in vitro or in vivo in a host. Such techniques include transfection of nucleic acid-$CaPO_4$ precipitates, transfection of nucleic acids associated with DEAE, transfection with a retrovirus including the nucleic acid of interest, liposome mediated transfection, and the like. For certain uses, it is preferred to target the nucleic acid to particular cells. In such instances, a vehicle used for delivering a nucleic acid of the invention into a cell (e.g., a retrovirus, or other virus; a liposome) can have a targeting molecule attached thereto. For example, a molecule such as an antibody specific for a surface membrane protein on the target cell or a ligand for a receptor on the target cell can be bound to or incorporated within the nucleic acid delivery vehicle. For example, where liposomes are employed to deliver the nucleic acids of the invention, proteins which bind to a surface membrane protein associated with endocytosis may be incorporated into the liposome formulation for targeting and/or to facilitate uptake. Such proteins include capsid proteins or fragments thereof tropic for a particular cell type, antibodies for proteins which undergo internalization in cycling, proteins that target intracellular localization and enhance intracellular half life, and the like. Polymeric delivery systems also have been used successfully to deliver nucleic acids into cells, as is known by those skilled in the art. Such systems even permit oral delivery of nucleic acids.

Other delivery systems can include time-release, delayed release or sustained release delivery systems. Such systems can avoid repeated administrations of the fugetactic agent, increasing convenience to the subject and the physician. Many types of release delivery systems are available and known to those of ordinary skill in the art. They include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono- di- and tri-glycerides; hydrogel release systems; sylastic systems; peptide based systems; wax coatings; compressed tablets using conventional binders and excipients; partially fused implants; and the like. Specific examples include, but are not limited to: (a) erosional systems in which the anti-inflammatory agent is contained in a form within a matrix such as those described in U.S. Pat. Nos. 4,452,775, 4,667,014, 4,748,034 and 5,239,660 and (b) diffusional systems in which an active component permeates at a controlled rate from a polymer such as described in U.S. Pat. Nos. 3,832,253, and 3,854,480.

A preferred delivery system of the invention is a colloidal dispersion system. Colloidal dispersion systems include lipid-based systems including oil-in-water emulsions, micelles, mixed micelles, and liposomes. A preferred colloidal system of the invention is a liposome. Liposomes are artificial membrane vessels which are useful as a delivery vector in vivo or in vitro. It has been shown that large unilamellar vessels (LUV). which range in size from 0.2-4.0 um can encapsulate large macromolecules. RNA, DNA, and intact virions can be encapsulated within the aqueous interior and be delivered to cells in a biologically active form (Fraley, et al., Trends Biochem. Sci., (1981) 6:77). In order for a liposome to be an efficient gene transfer vector, one or more of the following characteristics should be present: (1) encapsulation of the gene of interest at high efficiency with retention of biological activity; (2) preferential and substantial binding to a target cell in comparison to non-target cells: (3) delivery of the aqueous contents of the vesicle to the target cell cytoplasm at high efficiency: and (4) accurate and effective expression of genetic information.

Liposomes may be targeted to a particular tissue by coupling the liposome to a specific ligand such as a monoclonal antibody, sugar, glycolipid, or protein. Liposomes are commercially available from Gibco BRL, for example, as LIPOFECTIN™ and LIPOFECTACE™, which are formed of cationic lipids such as N-[1-(2,3 dioleyloxy)-propyl]-N, N,N-trimethylammonium chloride (DOTMA) and dimethyl dioctadecylammonium bromide (DDAB). Methods for making liposomes are well known in the art and have been described in many publications. Liposomes also have been reviewed by Gregoriadis, G. in Trends in Biotechnology, (1985) 3:235-241.

In one embodiment, the vehicle is a biocompatible microparticle or implant that is suitable for implantation into the mammalian recipient. Exemplary bioerodible implants that are useful in accordance with this method are described in PCT International application No. PCT/US/03307 (Publication No. WO 95/24929, entitled "Polymeric Gene Delivery System"). PCT/US/03307 describes a biocompatible, preferably biodegradable polymeric matrix for containing an exogenous gene under the control of an appropriate promoter. The polymeric matrix is used to achieve sustained release of the exogenous gene in the patient. In accordance with the instant invention, the fugetactic and/or anti-fugetactic agents described herein are encapsulated or dispersed within the biocompatible, preferably biodegradable polymeric matrix disclosed in PCT/US/03307.

The polymeric matrix preferably is in the form of a microparticle such as a microsphere (wherein a fugetactic and/or anti-fugetactic agent is dispersed throughout a solid polymeric matrix) or a microcapsule (wherein a fugetactic and/or anti-fugetactic agent is stored in the core of a polymeric shell). Other forms of the polymeric matrix for containing a fugetactic agent include films, coatings, gels, implants, and stents. The size and composition of the polymeric matrix device is selected to result in favorable release kinetics in the tissue into which the matrix is introduced. The size of the polymeric matrix further is selected according to the method of delivery which is to be used. Preferably when an aerosol route is used the polymeric matrix and fugetactic agent are encompassed in a surfactant vehicle. The polymeric matrix composition can be selected to have both favorable degradation rates and also to be formed of a material which is bioadhesive, to further increase the effectiveness of transfer. The matrix composition also can be selected not to degrade, but rather, to release by diffusion over an extended period of time.

In another important embodiment the delivery system is a biocompatible microsphere that is suitable for local, site-specific delivery. Such microspheres are disclosed in Chickering et al., Biotech. And Bioeng., (1996) 52:96-101 and Mathiowitz et al., Nature, (1997) 386:410-414.

Both non-biodegradable and biodegradable polymeric matrices can be used to deliver the fugetactic agents of the invention to the subject. Biodegradable matrices are preferred. Such polymers may be natural or synthetic polymers. Synthetic polymers are preferred. The polymer is selected based on the period of time over which release is desired, generally in the order of a few hours to a year or longer. Typically, release over a period ranging from between a few hours and three to twelve months is particularly desirable. The polymer optionally is in the form of a hydrogel that can absorb up to about 90% of its weight in water and further, optionally is cross-linked with multivalent ions or other polymers.

In general, fugetactic and/or anti-fugetactic agents are delivered using a bioerodible implant by way of diffusion, or more preferably, by degradation of the polymeric matrix. Exemplary synthetic polymers which can be used to form the biodegradable delivery system include: polyamides, polycarbonates, polyalkylenes, polyalkylene glycols, polyalkylene oxides, polyalkylene terepthalates, polyvinyl alcohols, polyvinyl ethers, polyvinyl esters, poly-vinyl halides, polyvinylpyrrolidone, polyglycolides, polysiloxanes, polyurethanes and co-polymers thereof, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly(methyl methacrylate), poly(ethyl methacrylate), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), polyethylene, polypropylene, poly(ethylene glycol), poly(ethylene oxide), poly(ethylene terephthalate), poly(vinyl alcohols), polyvinyl acetate, poly vinyl chloride, polystyrene, polyvinylpyrrolidone, and polymers of lactic acid and glycolic acid, polyanhydrides, poly(ortho)esters, poly(butic acid), poly(valeric acid), and poly(lactide-cocaprolactone), and natural polymers such as alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins, zein and other prolamines and hydrophobic proteins, copolymers and mixtures thereof. In general, these materials degrade either by enzymatic hydrolysis or exposure to water in vivo, by surface or bulk erosion.

Examples of non-biodegradable polymers include ethylene vinyl acetate, poly(meth)acrylic acid, polyamides, copolymers and mixtures thereof.

Bioadhesive polymers of particular interest include bioerodible hydrogels described by H. S. Sawhney, C. P. Pathak and J. A. Hubell in Macromolecules. (1993) 26:581-587, the teachings of which are incorporated herein, polyhyaluronic acids, casein, gelatin, glutin, polyanhydrides, polyacrylic acid, alginate, chitosan, poly(methyl methacrylates), poly(ethyl methacrylates), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate).

In addition, important embodiments of the invention include pump-based hardware delivery systems, some of which are adapted for implantation. Such implantable pumps include controlled-release microchips. A preferred controlled-release microchip is described in Santini, J T Jr. et al., Nature, 1999, 397:335-338, the contents of which are expressly incorporated herein by reference.

Use of a long-term sustained release implant may be particularly suitable for treatment of chronic conditions. Long-term release, are used herein, means that the implant is constructed and arranged to delivery therapeutic levels of the active ingredient for at least 30 days, and preferably 60 days. Long-term sustained release implants are well-known to those of ordinary skill in the art and include some of the release systems described above.

In certain embodiments, the isolated fugetactic agents of the invention are delivered directly to the site at which there is inflammation, e.g., the joints in the case of a subject with rheumatoid arthritis, the blood vessels of an atherosclerotic organ, etc. For example, this can be accomplished by attaching an isolated fugetactic molecule (nucleic acid or polypeptide) to the surface of a balloon catheter; inserting the catheter into the subject until the balloon portion is located at the site of inflammation, e.g. an atherosclerotic vessel, and inflating the balloon to contact the balloon surface with the vessel wall at the site of the occlusion. In this manner, the compositions can be targeted locally to particular inflammatory sites to modulate immune cell migration to these sites. In another example the local administration involves an implantable pump to the site in need of such treatment.

Preferred pumps are as described above. In a further example, when the treatment of an abscess is involved, the fugetactic agent may be delivered topically, e.g., in an ointment/dermal formulation. Optionally, the fugetactic molecules of the invention are delivered in combination with a non-fugetactic molecule (e.g., anti-inflammatory, immunosuppressant, etc).

In a preferred embodiment of the invention, the isolated fugetactic agents of the invention are administered to a subject in combination with a balloon angioplasty procedure. A balloon angioplasty procedure involves inserting a catheter having a deflated balloon into an artery. The deflated balloon is positioned in proximity to the atherosclerotic plaque and the site of inflammation, and is inflated such that the plaque is compressed against the arterial wall. As a result, the layer of endothelial cells on the surface of the artery is disrupted, thereby exposing the underlying vascular smooth muscle cells. The isolated fugetactic molecule is attached to the balloon angioplasty catheter in a manner which permits release of the isolated fugetactic molecule at the site of the atherosclerotic plaque and the site of inflammation. The isolated fugetactic molecule may be attached to the balloon angioplasty catheter in accordance with standard procedures known in the art. For example, the isolated fugetactic molecule may be stored in a compartment of the balloon angioplasty catheter until the balloon is inflated, at which point it is released into the local environment. Alternatively, the isolated fugetactic molecule may be impregnated on the balloon surface, such that it contacts the cells of the arterial wall as the balloon is inflated. The fugetactic molecule also may be delivered in a perforated balloon catheter such as those disclosed in Flugelman, et al., Circulation, v. 85, p, 1110-1117 (1992). See, also, e.g., published PCT Patent Application WO 95/23161, for an exemplary procedure for attaching a therapeutic protein to a balloon angioplasty catheter. This procedure can be modified using no more that routine experimentation to attach a therapeutic nucleic acid to the balloon angioplasty catheter.

Those skilled in the art will recognize, or be able to ascertain using no more than routine experimentation, many equivalents to the specific embodiments of the invention described herein. Such equivalents are intended to be encompassed by the following claims. All references disclosed herein are incorporated by reference in their entirety.

The invention will be more fully understood by reference to the following examples. These examples, however, are merely intended to illustrate the embodiments of the invention and are not to be construed to limit the scope of the invention.

EXAMPLES

Example I: Anti-fugetactic Agents Decrease Immune Evasion by Melanomas

T-cells are repelled by SDF-1 by a concentration-dependent and CXCR4 receptor-mediated mechanism. Repulsion of tumor antigen-specific T-cells from a tumor expressing SDF-1 allows the tumor cells to evade immune control. As shown herein, anti-fugetactic agents restore immune defenses against tumors.

I. Materials and Methods

A. C57Bl/6 and OT-I mice

C57Bl/6 mice between 6 and 10 weeks old were used in all experiments (Jackson Laboratory, Bar Harbor, Me.). The OT-I TCR transgenic mice were kindly provided by W. R. Heath and F. Carbone (Walter and Eliza Hall Institute, Melbourne, Australia). The OT-I TCR is expressed on CD8+ T cells and is specific for the peptide $OVA_{257\text{-}264}$ (SIINFEKL) bound to the class I MHC molecule H2-Kb (Hogquist, K. A., et al. 1994 Cell 76:17-2).

B. Cell Lines and Preparation of OT-I CTLs

B16 melanoma cells ($H2^b$) stably expressing chicken OVA (B16/OVA.pc) were provided by Drs. E. Lord and J. Frelinger (Brown, D. M., et al. 2001 Immunology 102:486-497). OT-I CD8+ T-cells were isolated from the spleens and lymph nodes of OT-I mice using the Magnetic Cell Sorting and Separation of Biomolecules (MACS) system (Miltenyi Biotec, Auburn, Calif.) and cultured and expanded (Delfs, M. W., et al. 2001 Transplantation 71:606-610). For CXCR4 expression, B16 cells and naïve or effector OT-I CD8+ T cells were immunostained using anti-CXCR4-FITC Ab (clone 2B11, BD Pharmingen) and analyzed on a FACS (Beckton Dickinson) using FlowJo Software (Tree Star, Inc. Ashland, Oreg.). Activated OT-I CD8+ T-cells were also exposed to murine rSDF-1α (PeproTech, Rocky Hill, N.J.) for 24 or 72 hours at final concentrations of 10, 100 and 1000 ng/ml. Cells were incubated with FITC-conjugated annexin V and propidium iodide (Detection Kit I, BD Pharmingen). Quantitation of CD69 (clone H1-2F3) and CD25 (clone PC61, all from BDPharmingen) expression and CFSE staining, was also employed for evaluation of the effect of SDF-1 on OT-1 CD8+ T-cell apoptosis, activation, and proliferation. The percentage of apoptotic cells was analyzed by FACS using FlowJo Software.

In order to analyze the effect of SDF-1 on T-cell proliferation, $2\times10^5$ OT-I total splenocytes or purified CD8+ T-cells were allowed to proliferate for 3 days in 96 round-bottom well plates precoated with 10 μg/ml anti-CD3 mAb (BD PharMingen) in the presence of 2 μg/ml soluble anti-CD28 mAb and 50 U/ml murine rIL-2. OT-I T-cells were preincubated for 3 hours with murine SDF-1 at final concentrations of 500 or 1000 ng/ml. SDF-1 at each concentration was also added every 24 hours to proliferating T-cells.

For CFSE analysis, T-cells were preincubated with 1 μM CFSE (Molecular Probe, Inc., Eugene, Oreg.) in PBS for 10 minutes. At the time of harvest, cells were washed twice in cold PBS buffer and incubated for 15 minutes at 4° C. with anti-CD69 and anti-CD25 mAb, and flow cytometry was performed on a FACSCalibur (BD Biosciences). Data analysis was performed with the FlowJo software (Tree Star, Inc. Ashland, Oreg.). For each marker, the threshold of positivity was found beyond the non-specific binding observed in the presence of irrelevant isotype matched control antibody. Mean log fluorescence intensity (MFI) values were obtained by subtracting the MFI of the isotype control from the MFI of the positively stained sample. To evaluate whether the differences between the peaks of cells were statistically significant with respect to controls, the Kolmogorov-Smirnov (K-S) test for analysis of histograms was used.

C. Generation of Genetically Modified B16 Cells Expressing SDF-1

Figure 1B:
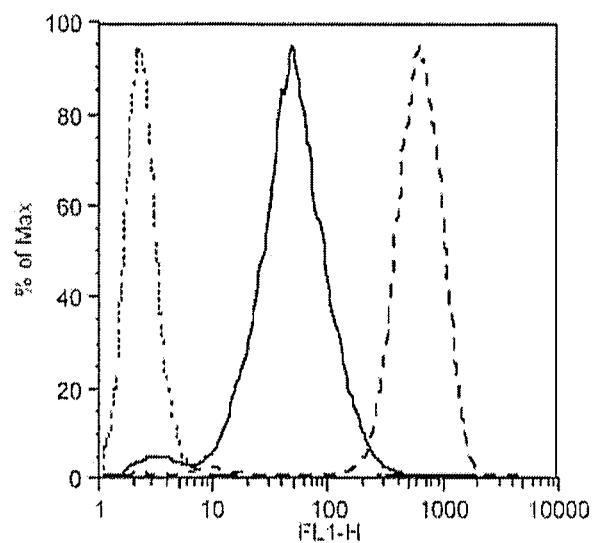

The coding region of murine SDF-1α (82-232 bp) was amplified by PCR and cloned into the EGFP encoding bicistronic murine stem cell virus derived retroviral transfer vector MSCV2.2, using XhoI and EcoRI cloning sites (FIG. 1A). Cloning results were confirmed by DNA sequencing. 293T HEK packaging cells were co-transfected with the following vectors using the calcium-phosphate method: EGFP encoding vectors MSCV2.2-SDF-1 or MSCV2.2, a packaging vector pKat, and pCMV-VSV-G (encoding the vesicular stomatitis virus G-glycoprotein). VSV-G pseudotyped retroviral vectors encoding SDF-1 and GFP or GFP alone were collected at 48 and 72 hours post-transfection and used for transduction of B16/OVA melanoma cells (Carlesso, N., et al. 1999. Blood 93:838-848). Cell sorting was performed using a FACS Vantage cells sorter (Becton Dickenson, Franklin Lakes, N.J.) in order to select the brightest 10% of B16/OVA.MSCV and two cell populations with bright and low levels of fluorescence termed B16/OVA.SDF-1-high and B16/OVA.SDF-1-low cells (FIG. 1B).

D. Quantitation of SDF-1 Production and Bioactivity

B16/OVA.MSCV and B16/OVA.SDF-1 cells were grown until they were 80-90% confluent. Cells were incubated for a further 24 hours in medium containing 0.5% FCS. Conditioned media (CM) were harvested and concentrated using Biomax 5K NMWL filter units (Millipore, Bedford, Mass.). Conditioned media were analyzed by Western blotting using mouse monoclonal anti-SDF-1 Ab (R&D Systems, Minneapolis, Minn.), HRP labeled sheep anti-mouse Ab (Amersham Biosciences Corp, Piscataway, N.J.), and ECL detection kit (Amersham). The level of SDF-1 in conditioned media was also determined by sandwich ELISA (QUANTIKINE, R&D Systems Inc., Minneapolis, Minn.). Levels of OVA secreted in conditioned media from B16/OVA.MCSV and B16/OVA.SDF-1 cells cultured for 24 hours were also measured by Elisa (Alpha Diagnostic Int. San Antonio, Tex.).

Quantitative transmigration assays were performed using a transwell system as described (Poznansky, M. C., et al. 2000 Nature Med 6:543-548). Purified murine CD8+ T cells ($6\times10^4$ cells) were added to the upper chamber of each well in a total volume of 150 μl Iscove's modified medium. Conditioned media, 20-fold concentrated, undiluted, or diluted 1:10 in DMEM containing 0.5% FCS was added in the lower, upper, or both lower and upper chambers of the transwell to generate a standard "checkerboard" analysis of cell migration. Further control wells assessed the chemotactic and fugetactic activity of rSDF-1 at concentrations of 100 ng/ml and 1 µg/ml. Migration of cells was quantitated as previously described (Poznansky, M. C., et al. 2000 *Nature Med* 6:543-548). Chemotactic index (CI) and fugetactic index (FI) were determined as a ratio between the number of cells migrating in experimental conditions divided by the number of cells migrating in the control setting with conditioned media in both upper and lower chambers.

E. Tumorigenicity of B16/OVA Cells in Naïve and Immunized Mice

For in vitro growth, $5 \times 10^5$ tumor cells were seeded in T25 flasks (Becton Dickinson, Le Pont De Claix, France). Cultures were harvested daily for 3 consecutive days and viable cell yield determined. Tumorigenicity was determined by subcutaneous (s.c.) injection of $2 \times 10^5$ viable cells into the flank of mice in a total volume of 200 µl PBS using a 27 G needle. Tumor growth was also evaluated in naïve mice challenged with B16/OVA.MSCV or B16/OVA.SDF-1-high cells and injected twice a day s.c. with the CXCR4 antagonist, AMD3100 (1.25 mg/kg s.c., Sigma). Tumor growth was measured every three or four days using a caliper. Tumor volume was recorded as the product of two orthogonal diameters (a×b; a=longest diameter; b=orthogonal width) (Hanson, H. L., et al. 2000 *Immunity* 13:265-276). In immunization studies, mice were injected s.c. (at multiple sites) with $1 \times 10^6$ irradiated (8568 cGy) B16/OVA.pc cells in a volume of 200 µl at d 0 and d 10. Fourteen days after immunization, mice were challenged s.c. in both flanks with $2 \times 10^5$ B16/OVA.MSCV or B16/OVA.SDF-1-high cells, and tumor growth was measured as described above (Dranoff, G., et al. 1993 *Proc Natl Acad Sci USA* 90:3539-3543). In some experiments, mice were immunized with B16/OVA.SDF-1-high cells and then challenged with B16/OVA.SDF-1-high or B16/OVA.SDF-1-low cells. Mice were sacrificed when one or both tumors reached 200 mm² in volume.

F. Adoptive Immunotherapy, Transfer of Nanoparticle Labeled CTL, and Survival Analysis For survival analysis, mice received $1 \times 10^7$ OT-I CD8+ T-cells in 500 µl of HBSS via tail vein injection. Two groups of mice received HBSS as control. 21 d after adoptive transfer of OT-I CTL, each group of experimental and control mice was challenged s.c. in the right flank with $2 \times 10^5$ B16/OVA.SDF-1 cells or B16/OVA.MSCV control cells in 200 µl of HBSS using a 27 G needle (Bathe, O. F., et al. 2001 *J Immunol* 167:4511-4517). Tumor cell growth was recorded every 3-4 days. Detectable tumor was considered to be >5 mm². Mice were sacrificed when tumors reached 400 mm² in size.

Tat peptide derivatized CLIO (CLIO-HD) was synthesized as described (Kircher, M. F., et al. 2003 *Cancer Res* 63:6838-6846). For each experiment, mice were injected s.c. in the right and left flank respectively with $5 \times 10^5$ B16/OVA.MSCV and B16/OVA.SDF-1-high cells. When tumors reached 10-15 mm in at least one diameter, OT-I CD8+ T cells expanded in vitro (Brown, D. M. et al. 2001 Immunology 102:486-497) were harvested, incubated with CLIO-HD (300 µg/ml/$1 \times 10^7$ cells), and $3 \times 10^7$ labeled cells were injected i.p. into mice bearing bilateral tumors of similar size. Distribution of CLIO-HD labeled cells over time was assessed via MR imaging (Bruker Pharmascan, 4.7 T) at 24 and 48 hours after adoptive transfer. T2 images were used to generate 3D reconstructions, and T2 measurements were used to quantitate tumoral recruitment of labeled cells as described. (Kircher, M. F. 2003 *Cancer Res* 63:6838-6846).

Mice were anesthetized throughout imaging with 1-2% isoflurane at 1.5 liter/min. For the analysis of T cell recruitment, an axial T2-weighted gradient echo sequence (TR=600 ms, TE=6.0, FOV 4.24×2.12 cm, MTX 256×128, 4 averages) and an axial T2-weighted fast spin echo sequence (TR=2000 ms, TE=48.6 ms, FOV 4.24×2.12 cm, MTX 256×128, 8 averages) were used. T2 fit values were derived from a multislice multiecho sequence (TR=2000 ms, TE=6.5×16 ms, FOV 4.24×2.12 cm, MTX 128×128, 2 averages). Regions of interest for the tumors were drawn by hand, and T2 fit values were calculated using an in-house program, CMIR-Image (Kircher, M. F., et al. 2003. *Cancer Res* 63:6838).

In some experiments, activated OT-1 CD8+ T cells were also preincubated with the CXCR4 antagonist, AMD3100, at concentrations of 0.08 and 0.25 µg/ml (15 min at RT) in a 12-well plate at a density of $1 \times 10^7$ cells/well prior to adoptive transfer (Hatse, S., et al. 2002. *FEBS Lett* 527:255). Survival analysis was evaluated in mice after in vivo generation of a tumor-specific memory T cell compartment (Bathe, O. F., et al. 2001. *J Immunol* 167:4511). 21 days after adoptive transfer of $1 \times 10^7$ OT-1 CD8+ T cells (in 500 µl of HBSS via tail vein injection), two groups of mice (4 or 6 per group) were challenged s.c. in the right flank with $2 \times 10^5$ B 16/OVA.SDF-1-high cells or B16/OVA.MSCV control cells in 200 µl of HBSS using a 27 G needle (Bathe, O. F., et al. 2001. *J Immunol* 167:4511). As controls, two groups of mice which did not receive adoptive transfer were challenged with tumors. Detectable tumor was considered to be >5 mm². Mice were sacrificed when tumors reached 400 mm² in size.

G. Tumor Immunohistochemistry and FACS Analysis of Tumor-Infiltrating Lymphocytes.

Immunized mice and mice that received adoptive transfer of OT-I CD8+ T-cells were evaluated for T cell infiltration of tumors by immunohistochemistry. Animals were sacrificed and tumors excised with preservation of the capsule. Resected tumors were fixed in 10% neutral buffered formalin and embedded in paraffin. Serial 5 µm sections of tumors were stained with H & E or with polyclonal anti-CD3 Ab or isotype control Ab, followed by incubation with secondary HRP-labeled anti-rabbit Dako EnVision Ab (DakoCytomation). T-cell infiltration was quantified by counting four random 200× field powers of the tumor sections, each 0.5 mm² in area.

Quantitation of tumor-infiltrating lymphocytes (TIL) by FACS was performed in all mice that received OT-I CD8+ T cells for survival analysis (Shrikant, P., et al. 1999. *Immunity* 11:483-493). Mice were sacrificed, and tumors and two draining lymph nodes were harvested. The total number of CD8/TCR-Vβ-5-1/Vα-2-positive cells was calculated from the percentage of the total number of cells recovered from 100 mg of tumor. 100 mg of tumor tissue was treated with DMEM medium containing DNAse I 270 IU/ml, collagenase 200 IU/ml, and hyaluronidase 35 IU/ml for 1 hour at 37° C., filtered and washed 3 times with HBSS.

After Fc binding by 2.4G2 Ab, $5 \times 10^5$ cells were stained with anti-CD8-APC (clone 53-6.7), Vα-2-TCR-PE (clone B20-1), Vβ-5,1,5,2-TCR-FITC (clone MR9-4) (BD Pharmingen) Abs and examined on a FACS. Melanin-containing B16 tumor cells were clearly distinguished from TIL by their side and forward scatter by FACS. The total number of OT-I CD8+ cells in each tumor fragment was calculated from the percentage of CD8/TCR-Vβ-5-1/Vα-2-positive cells in the total number of cells recovered from 100 mg of tumor.

H. Quantitation of CTL Efficacy in Vitro

Cytotoxicity of OT-I CD8+ cells was measured in a standard $^{51}$Cr-release assay in round-bottom wells as previously described (Brainard, D. M., et al. 2004. *J Virol* 78:5184-5193). The assay was also modified and performed in flat-bottom wells in order to determine the effects of CTL migration on killing efficacy in the context of target cells expressing SDF-1 (Hahne, M., et al. 1996 *Science* 274:1363-1366). B16/OVA.MSCV or B16/OVA.SDF-1-high target cells were labeled with 100 µCi of $^{51}$Cr per 10[6] cells for 1 hour at 37° C. After pulsing with 1 µM OVA-specific SIINFEKL-peptide, dilutions of effector cells were added to $^{51}$Cr-labeled target cells in 100 µl aliquots to give the indicated effector-to-target cell ratios (from 30:1 to 1:1) and then incubated at 37° C. in 5% $CO_2$ for 5 hours. 30 µl of supernatant were harvested, and the radioactivity was counted in a γ-radiation counter. Cytotoxicity was expressed either as percent of lysis or as Lytic Unit 30 (LU30) as previously described (Brainard, D. M., et al. 2004. *J Virol* 78:5184-5193, Bryant, J., et al. 1992. *J Immunol Meth* 146:91-103). [51]Cr release assays were also performed in flat-bottom wells after preincubation of OT-I CD8+ T cells with the CXCR4 antagonist AMD3100 at concentrations of 0.25 and 1 µg/ml (Hatse, S. 2002 *FEBS Lett* 527:255-262).

The effect of SDF-1 on CTL efficacy was also measured after proliferating OT-I CD8+ T cells were cocultured with B16/OVA.SDF-1-high or B16/OVA.MSCV cells. In this assay, 5×10[6] OT-I CD8+ T cells were allowed to proliferate for 5 days in 12 well plates in the presence of 10 µg/ml anti-CD3, 2 µg/ml anti-CD28 and 50 U/ml IL-2. 5×10[5] B16/OVA.MSCV or B16/OVA. SDF-1-high cells were seeded in a 0.4 µM pore polycarbonate membrane (Corning Life Sciences, Acton, Mass.) and placed in the upper chamber from the first day of culture.

In a parallel experiment, OT-I CD8+ T cells were allowed to proliferate for 5 days in the presence of rSDF-1 at 500 or 1000 ng/ml concentrations added daily to each well. In this set of experiments, CTL killing activity was measured against B16/OVA.MSCV or B16/OVA. SDF-1-high not pulsed with the SIINFEKL antigen.

I. Analysis of Activation, Proliferation and Apoptosis of OT-1 T-Cells Exposed to SDF-1

Activated OT-1 CD8+ T-cells were exposed to murine rSDF-1α (PeproTech, Rocky Hill, N.J.) for 24 or 72 hours at final concentrations of 10, 100 and 1000 ng/ml. Cells were incubated with FITC-conjugated annexin V and propidium iodide (Detection Kit I, BD Pharmingen). The percentage of apoptotic cells was analyzed by FACS using FlowJo Software (Colamussi, M. L., et al. 2001. *J Leukoc Biol* 69:263). In order to analyze the effect of SDF-1 on T-cell proliferation, 2×10[5] OT-1 total splenocytes or purified CD8+ T-cells were allowed to proliferate for 3 days in 96 round-bottom well plates precoated with 10 µg/ml anti-CD3 mAb (BD PharMingen) in the presence of 2 µg/ml soluble anti-CD28 mAb and 50 U/ml murine rIL-2. OT-1 T-cells were preincubated for 3 hours with murine rSDF-1 at final concentrations of 500 or 1000 ng/ml. SDF-1 at each concentration was also added every 24 hours to proliferating T-cells.

For CFSE analysis, T cells were preincubated with 1 µM CFSE (Molecular Probe, Inc., Eugene, Oreg.) in PBS for 10 minutes. At the time of harvest, cells were washed twice in cold PBS buffer and incubated for 15 minutes at 4° C. with anti-CD69 and anti-CD25 mAb, and flow cytometry was performed on a FACSCalibur (BD Biosciences). Data analysis was performed with the FlowJo software (Tree Star, Inc. Ashland, Oreg.). For each marker, the threshold of positivity was found beyond the non-specific binding observed in the presence of irrelevant isotype matched control antibody. Mean log fluorescence intensity (MFI) values were obtained by subtracting the MFI of the isotype control from the MFI of the positively stained sample. The Kolmogorov-Smirnov (K-S) test was used to evaluate whether the differences between the distributions of MFI were statistically significant with respect to controls.

J. Modeling of the SDF-1 Gradient Generated in the Tumor Microenvironment

The SDF-1 concentration within and around the periphery of a subcutaneous B16/OVA.SDF-1 tumor was mathematically modeled. The tumor was modeled as a spherical source of chemokine in an infinite homogeneous medium of normal tissue. The model proposes that SDF-1 is produced inside the tumor at the same time as it is dispersed by diffusion and degraded inside the tumor and the surrounding tissue. The chemokine concentration c at distance r from the center of the tumor was calculated at steady state from the mass balance on chemokine concentration around a radial shell of thickness Δr:

$$V\frac{\partial c}{\partial t} = (J \times A)|_r - (J \times A)|_{r+\Delta r} + V \times G - V \times E_g \tag{1}$$

where V is the volume of the tumor, c and J are the concentration and flux of chemokine, D the diffusion coefficient (0.6×10[−7] cm[2]/s) (Lankelma, J. et al. 2000. *Microvasc Res* 59:149-161). G the chemokine production per unit volume, and $E_g$ the rate of degradation of SDF-1.

The chemokine flux J was calculated from the Fick's first law of diffusion as:

$$J = -D\frac{\partial c}{\partial r} \tag{2}$$

The rate of generation G of SDF-1 was estimated experimentally from the measured amount of chemokine produced over 24 hours in a cell suspension (58±28.5 ng/10[6] cells/24 h). The rate of degradation of SDF-1 was estimated at between 6 and 24 hours and was based on previous reports from in vivo studies (Poznansky, M. C., et al. 2000. *Nature Med* 6:543-548).

Substituting the above in Equation (1) yielded the governing partial differential equation for SDF-1 concentration at distance r from the center of the tumor:

$$\frac{\partial c}{\partial t} = D\frac{\partial^2 c}{\partial r^2} + \frac{2}{r}\frac{\partial c}{\partial r} + G - E_g \tag{3}$$

Equation (3) was solved using the finite differences method by forward differencing in time and central differencing in space. The equation was solved in time until to a steady state, where further resolving in time did not change the concentration distribution of SDF-1.

K. Statistical Analysis

Statistical significance of numerical data was determined using the Wilcoxon signed rank exact test or Student's paired t-test. The statistical survival analysis was performed using die Mantel-Cox log-rank test.

II. Results

A. Engineered B16/OVA.SDF-1 Cells Express High or Low Levels of Functional SDF-1

Figure 1C:
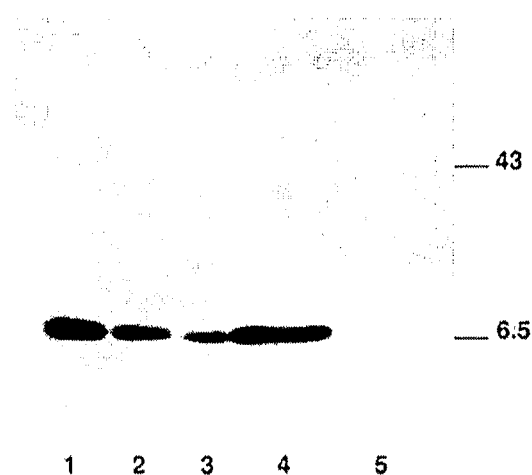

Cell sorting was performed to select the transduced B16/OVA.pc cells that were the brightest and dimmest B16/OVA.SDF-1 cells, termed B16/OVA.SDF-1-high and B16/OVA.SDF-1-low (FIG. 1B). The cells transduced with the MSCV vector encoding GFP alone were used as the control cell line in all experiments. Calculation of SDF-1 concentration in the conditioned media from B16/OVA-SDF-1-high and -low cultures as measured by Western blot and ELISA ranged from 35 to 110 ng/ml (mean=58±28.5 ng) and 2.4 to 13 ng/ml (mean=7.6±4.1), respectively, from $1\times10^6$ cells cultured for 24 hours (FIG. 1C). No SDF-1 was detected in conditioned media from untransduced B16/OVA cells or B16/OVA cells transduced with MSCV-GFP by Western blotting or ELISA (data not shown). No significant difference in class I MHC expression and OVA production between B16/OVA.SDF-1 transductants and B16/OVA.MSCV cells (Table 1, below) was detected. B16/OVA.MSCV and B16/OVA.SDF-1 cells expressed very low levels of CXCR4 by flow cytometry (Table 1, below).

TABLE 1

Table 1. FACS analysis of MHC class I and CXCR4 expression in B16/OVA.MSCV and B16/OVA.SDF-1 high and low cells. Results are shown as Mean Fluorescent Intensity values (MFI). Levels of SDF-1 and OVA secretion in the supernatant from $1 \times 10^6$ B16/OVA.MSCV and B16/OVA.SDF-1-high cells cultured for 24 hours are shown (mean ± SD).

|  | MHC-I (MFI ± SD) | OVA (pg/ml ± SD) | SDF-1 (ng/ml ± SD) | CXCR4 (MFI ± SD) |
|---|---|---|---|---|
| B16.OVA/MSCV | 16.2 ± 2.1 | 950 ± 70 | — | 3.06 ± 0.65 |
| B16.OVA/SDF-1-high | 17.1 ± 1.9 | 1200 ± 282 | 58 ± 28.5 | 2.45 ± 0.67 |
| B16.OVA/SDF-1-low | 17.9 ± 1.3 | 994 ± 34 | 7.6 ± 4.1 | 2.88 ± 0.96 |

The effect of the SDF-1/CXCR4 axis on tumor growth was evaluated in mice untreated and treated with the specific CXCR4 antagonist, AMD3100, in vivo from the first day after challenge with tumor cells until the appearance of tumors. The average time to tumor growth to a size of 200 mm² size was 22±2 days (average ±SD) and 24±1.3, respectively, for B16/OVA.MSCV treated or untreated with AMD3100 (p=0.32, not shown). The time for tumor growth to 200 mm² for AMD3100-untreated and -treated B16/OVA.SDF-1-high tumors, was 23±1.5 and 23.6±2.08 days, respectively (p=0.72, not shown).

Figure 2A:
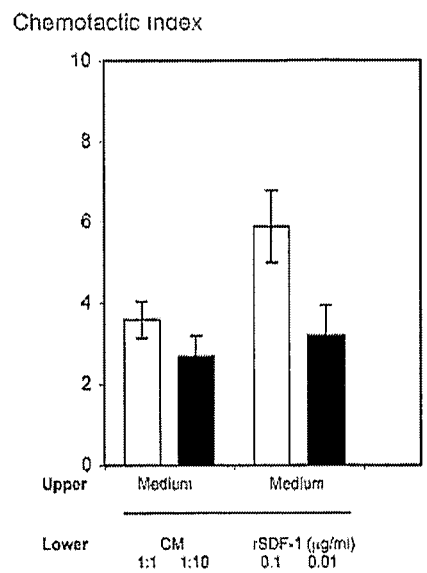
FIG. 2: Bar graphs depicting chemotactic and fugetactic indices calculated for murine CD8+ T cells subjected to in vitro transmigration assays in the presence of conditioned medium (wherein B16/OVA.SDF-1 high cells had been incubated), in comparison with rSDF-1 controls.
Figure 2B:
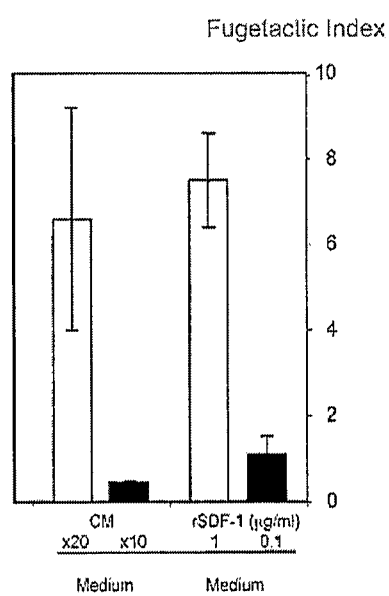

Conditioned media from B16/OVA.SDF-1-high cells and B16/OVA.MCSV cells were tested for functional activity in transmigration assays (FIG. 2). Undiluted and 1:10 diluted conditioned media from B16/OVA.SDF-1 cells generated a chemotactic index (CI) (ratio between the number of cells in the experimental setting divided by the number of cells in the control setting in which conditioned media was placed in the upper and lower chamber of the transwell) for primary marine CD8+T-cells of 3.6±0.46 (mean±SEM) and 2.7±0.5, respectively (FIG. 2A). Murine rSDF-1 (100 ng/ml) gave a CI of 5.9±0.9. Conditioned medium from B16/OVA.SDF-1-high cells was then added to the upper chamber for evaluation of fugetactic activity (FIG. 2B). The fugetactic index (FI) (ratio between the number of cells migrating away from conditioned medium in the experimental setting divided by the number of cells migrating in the control setting in which conditioned medium was placed in the upper and lower chambers of the transwell) was 6.6±2.6 in the presence of 20-fold concentrated and 0.45±0.025 for 10-fold concentrated conditioned media (FIG. 2B). Murine rSDF-1 (1 µg/ml) added to the upper chamber gave a FI of 7.5±1.1. No chemotactic or fugetactic activity was found when concentrated and undiluted conditioned media from B16/OVA.MSCV were tested in this system (data not shown).

Figure 3A:
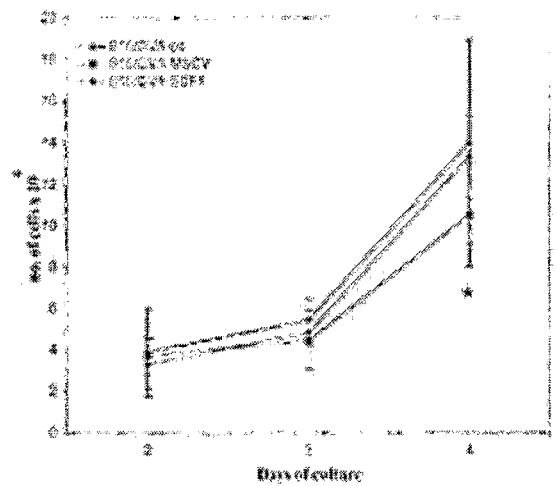
FIG. 3: In vitro growth (A) and in vivo tumorigenicity (B) of B16/OVA.pc, B16/OVA.MSCV, B16/OVA.SDF-1 tumor cells.
Figure 3B:
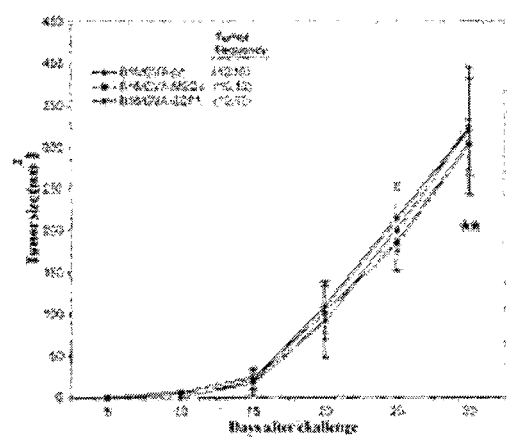

B. Expression of SDF-1 by B16/OVA Cells Does not Affect the Kinetics of Tumor Growth FACScan analysis of class I MHC expression (anti-H-$2K^{-b}$, clone AF6-88.5, BD Pharmingen) showed similar levels of expression in B16/OVA.SDF-1 cells (MFI 17.1±1.9 SD) and B16/OVA.MSCV (MFI 16.2±2.1 SD) (p=0.14; data not shown). B16/OVA cells transduced with MSCV or SDF-1 expressed very low levels of CXCR4 by flow cytometry (MFI: 3.06±0.65 and 2.45±0.67, respectively). The growth of B16/OVA.MSCV cells was not significantly different from B16/OVA.SDF-1 cells in vitro (FIG. 3A; p=0.13). B16/OVA.MSCV and B16/OVA.SDF-1 tumors showed similar growth kinetic in vivo, suggesting that SDF-1 had no major effect on tumor growth in syngeneic mice in the model described herein (FIG. 3B; p=0.23). In view of the very low level of CXCR4 expression in B16/OVA cells, the effect of the SDF-1/CXCR4 axis on tumour growth was also evaluated by in vivo treatment of naïve mice with the CXCR4 antagonist, AMD3100, from the first day after challenge until appearance of tumours. The average time to tumor growth to a size of 200 mm² size was 22±2 days (average ±SD) and 24±1.3, respectively, for B16/OVA.MSCV treated or untreated with AMD3100 (p=0.32). The time in B16/OVA.SDF-1 tumors was 23±1.5 and 23.6±2.08, respectively, for untreated and AMD3100-treated tumors (p=0.72).

C. Immunized Mice do not Control the Growth of B16OVA-SDF-1-High Tumors

Figure 4A:
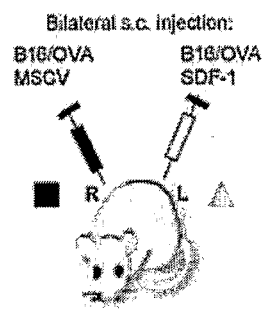
FIG. 4: Tumor sizes for each mouse at time of sacrifice are shown.
Figure 4B:
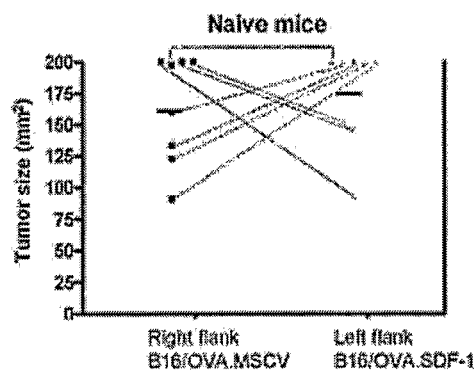
Figure 4C:
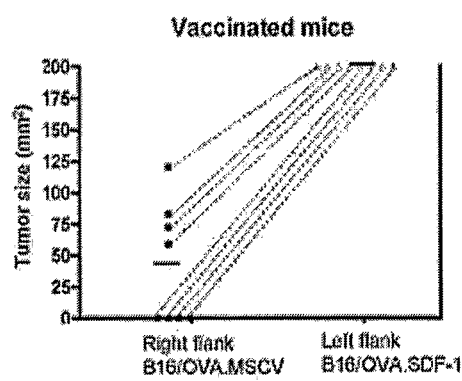

To study the local effect of SDF-1 secretion by a tumor, non-immunized or immunized mice were challenged with both $2\times10^5$ B16/OVA.MSCV and B16/OVA.SDF-1 tumor cells into the right and left flank, respectively (FIG. 4A). Subsequent tumor growth was measured every three or four days, and mice were sacrificed when at least one tumor reached 200 mm². When naive non-immunized mice were injected bilaterally with B16/OVA.MSCV and B16/OVA.SDF-1-high cells, tumors in all cases developed to a size of 200 mm², and all mice were sacrificed by d 25 following challenge. No mouse died of causes directly or indirectly related to the growth of the tumor itself. When comparing the bilateral tumor size in each mouse, a random pattern of growth was observed (FIG. 4B). In 50% of animals, B16/OVA.SDF-1-high tumors grew more rapidly than the contralateral B16/OVA.MSCV tumor, and there was no significant growth advantage of SDF-1-expressing tumors over control B16/OVA.MSCV tumors (FIG. 4B; p=0.7). In contrast, immunized mice demonstrated a strikingly different pattern of tumor growth (FIG. 4C). Fifty percent of immunized mice showed no evidence of B16/OVA.MSCV tumor development in the right flank at the end of follow-up, whereas all mice developed the B16/OVA.SDF-1-high tumor in the left flank. When comparing the tumor size in mice that developed bilateral tumors, all mice developed a >200 mm² B16/OVA.SDF-1-high tumor when the contralateral B16/OVA.MSCV tumor was significantly smaller in size (FIG. 4C; p=0.0001). B16/OVA.SDF-1-high tumor growth in immunized mice was significantly delayed in comparison to tumor growth in non immunized mice (respectively, 29.4±4.9 vs 12.8±2 d, mean±SD, p=0.0002), indicating that the immune system plays a role in the control of tumor growth in this model.

Immunohistochemistry was performed in order to quantitate T-cell infiltration into tumors that were not rejected. In non-immunized mice, there was minimal CD3+ T-cell infiltration into both B16/OVA.MSCV and B16/OVA.SDF-1-high tumors (data not shown). In contrast, there was consistent CD3+ T-cell infiltration into B16/OVA.MSCV tumors in immunized mice (FIG. 5, panels A-C). T-cell infiltration into B16/OVA.SDF-1-high tumors in immunized mice was markedly reduced (FIG. 5, panels D-F). The number of CD3+ T-cells (in four 200× fields from 3 mice per group) infiltrating B16/OVA.MSCV tumors was 92.2±28.8 cells/mm$^2$ (p=0.016), in contrast to 34.5±10.6 cells/mm$^2$, mean±SD, infiltrating B16/OVA.SDF-1-high tumors (p=0.001). These data indicate that intratumoral expression of high concentrations of SDF-1 leads to a reduction in TIL.

Figure 6A:
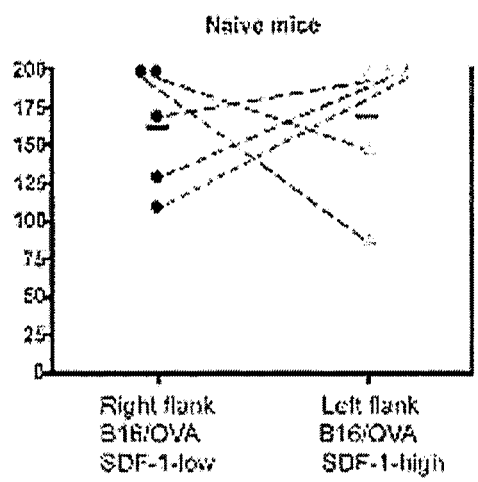
FIG. 6: Graphic depictions of results of challenge of immunized (with irradiated B16/OVA. SDF-1-high cells) vs. non-immunized mice with B16/OVA.SDF-1-low and -high tumor cells. Results are shown in terms of tumor development/growth and quantitation of T cell infiltrates.
Figure 6B:
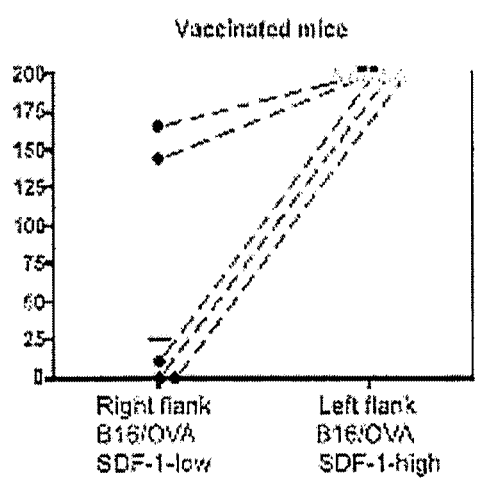
Figure 6C:
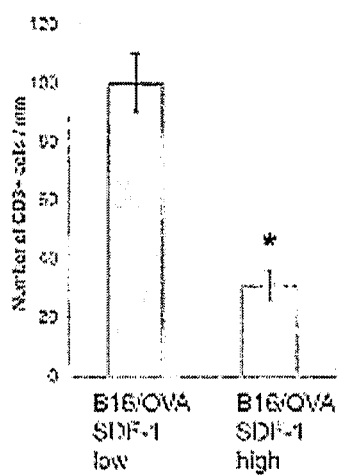

The effect of vaccination of mice with irradiated B16/OVA cells expressing high levels of SDF-1 to protect mice from bilateral challenge with B16/OVA.SDF-1-low and -high cells was also evaluated. As shown in FIG. 6A, naïve mice challenged with bilateral B16/OVA.SDF-1-low and -high cells showed a random pattern of growth (p=0.088). In contrast, vaccination with irradiated B16/OVA cells expressing high levels of SDF-1 resulted in rejection of 40% of B16/OVA.SDF-1-low tumors, whereas all mice developed B16/OVA.SDF-1-high tumors in the left flank (FIG. 6B; p=0.021). Furthermore, mice that developed bilateral tumors showed a slower rate of growth of B16/OVA.SDF-1-low compared to B16/OVA.SDF-1-high tumors (data not shown). Quantitation of T-cell infiltration by immunohistochemistry revealed a significantly greater infiltration of CD3+ cells into B16/OVA.SDF-1-low tumors (101±10 cells/mm$^2$) than into B16/OVA.SDF-1-high tumors (31±5.1 cells/mm$^2$; p=0.007; FIG. 6C). These data support the concept that, although SDF-1 does not affect the immunogenicity of B16/OVA cells, it can serve as a bidirectional cue for T-cells, attracting at low concentration and repelling at high concentration.

D. High, But not Low, Levels of SDF-1 Reduce Recruitment of Adoptively Transferred OVA-Specific CTL into Tumors Adoptive transfer of TCR transgenic T-cells into syngeneic recipients makes it possible to directly visualize and quantify T-cell responses in vivo. It has been shown previously that OT-I CD8+ cells can be efficiently and specifically recruited into tumors as early as 12 hours after adoptive transfer into C57BL/6 mice bearing OVA-expressing B16 tumors (Kircher, M. F., et al. 2003 *Cancer Res* 63:6838-6846). In this study, mice were implanted subcutaneously with control B16OVA-MSCV (right flank) and B16OVA-SDF-1-high cells (left flank), so that each animal served as its own control. Serial MR images were taken of the animals when tumors reached 10-15 mm in one diameter. Animals bearing tumors similar in size were imaged at 24 and 48 hours after adoptive transfer of CLIO-tat labeled OT-1 cells. Lymphocyte infiltration of tumors, as evidenced by quantitation of signal reduction, was consistently reduced in B16/OVA.SDF-1-high as compared to B16/OVA.MCSV tumors. In a representative axial slice (FIG. 7), a clear, although heterogeneous, signal reduction could be visualized in the B16/OVA.MSCV tumor 24 hours after injection of OT-I CD8+ T-cells, whereas a small change in signal intensity was observed in the contralateral B16/OVA.SDF-1-high tumor, indicating that few T-cells were recruited (T2 fit value ratio between the right and left tumor: 0.58). MRI at 48 hours after CTL injection did not differ significantly from 24-hour analysis for both B16/OVA.MSCV and B16/OVA.SDF-1-high tumors (data not shown). Tumors were harvested 48 hours after adoptive transfer of labeled T-cells, and sections were stained with H&E and anti-CD3 Ab (FIG. 8). CD3+ T-cell infiltration was clearly observed in B16/OVA.MSCV tumors (FIG. 8A-C), whereas only rare CD3+ T cells were found infiltrating the B16/OVA.SDF-1-high tumor in the same mouse (FIG. 8D-F). Quantitative analysis of CD3+ cells in immunohistochemical samples (FIG. 8G) showed a 3-fold difference in T-cell infiltration in B16/OVA.MSCV (115.2 cells/mm$^2$+35.5, mean±SD), compared to B16/OVA.SDF-1-high tumors (38 cells/mm$^2$+17) (p=0.018). No evidence of intravascular accumulation of T-cells was observed in B16/OVA.SDF-1-high or B16/OVA.MSCV tumors. CD3+ T-cells were very rarely seen in control mice that did not receive adoptively transferred T-cells (data not shown). Thus, early recruitment of tumor-specific CTL is reduced when SDF-1 is expressed at a high level in the tumor.

Figure 9:
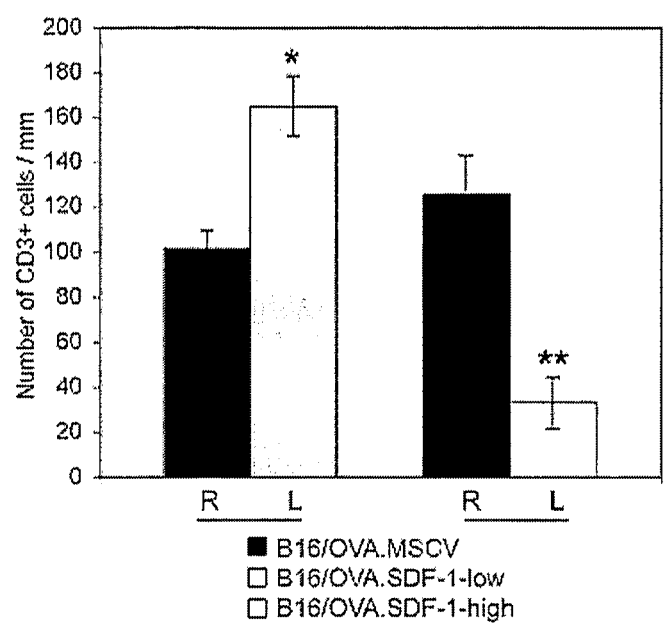
FIG. 9: Bar graph depicting the number of tumor infiltrating CD3+ cells found in mice challenged with B16/OVA.SDF-1-low vs. -high cells vs. B16/OVA.MSCV cells.

To confirm that SDF-1 impairs the recruitment of OT-I CD8+ T-cells when expressed at high but not low levels, the level of T-cell infiltration was evaluated in tumors expressing low levels of SDF-1. Mice bearing bilateral B16/OVA.MSCV and B16/OVA.SDF-1-low or B16/OVA.MSCV and B16/OVA.SDF-1-high tumors were adoptively transferred with OT-I CD8+ T-cells, and T-cell infiltration was quantitated 48 hours later by immunohistochemistry. Quantitation of T-cell infiltration showed that the expression of low levels of SDF-1 was associated with a higher number (164±14 cells/mm$^2$) of T-cells infiltrating B16/OVA.SDF-1-low tumors compared to control B16/OVA.MSCV tumors (101±8.5 cells/mm$^2$) growing in the contralateral thigh (FIG. 9; p=0.032). Therefore, recruitment of adoptively transferred activated tumor antigen-specific CTLs into B16/OVA tumors is significantly increased when SDF-1 is expressed at a low level and reduced when SDF-1 is expressed at a high level by the tumor.

E. Failure of T-Cells to Infiltrate SDF-1 Secreting Tumors is CXCR4-Mediated

Figure 10O:
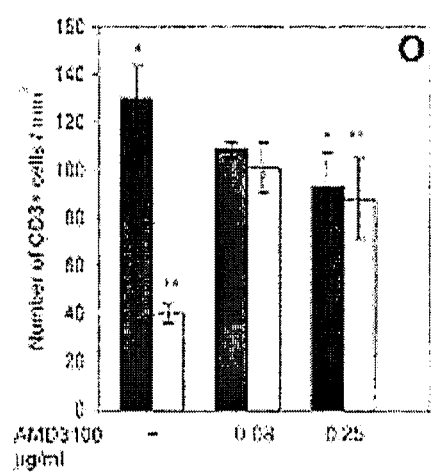
FIG. 10: Axial Magnetic Resonance (MR) images generated after adoptive transfer of OT-1 CD8+ T cells incubated with PBS or AMD3100 into mice bearing bilateral B16/OVA.MSCV and B16/OVA.SDF-1-high tumors. Images depicting CD3-specific staining of tissues collected after adoptive transfer and bar graph depicting quantitation of same.

In order to investigate whether the expression of high levels of SDF-1 did indeed have a direct fugetactic effect on tumor-specific T-cells, the effect was studied of CXCR4 blockade by AMD3100 on the early recruitment of OT-1 T-cells (FIG. 10) (Hatse, S., et al. 2002. *FEBS Lett* 527:255). CLIO-TAT labeled OT-1 CD8+ T-cells were incubated with AMD3100 at 0.08 and 0.25 μg/ml and adoptively transferred into mice bearing bilateral tumors. T-cell recruitment was evaluated by MRI and by immunohistochemistry. A clear MRI signal reduction was observed in the B16/OVA.MSCV tumor and not in the B16/OVA.SDF-1-high tumor 24 hours after adoptive transfer of OT-1 T-cells untreated with AMD3100 (FIGS. 10A, D). In contrast, T-cell recruitment was clearly visible in the B16/OVA.MSCV, as well as in the B16/OVA.SDF-1-high, tumor when OT-1 CD8+ T-cells were pretreated with AMD3100 (FIGS. 10B, E). Quantitation of the T2 fit value in the right and left tumors gave a ratio of 0.55±0.13 (mean±SD, n=3) in the AMD3100-pretreated setting, compared to a ratio close to 1 (I+0.12) when OT-1 T-cells were pretreated with AMD3100 before adoptive transfer (p=0.01). To rule out variabilities between mice, a second adoptive transfer with OT-1 T-cells pretreated with AMD3100 was performed in the same group of mice that received AMD3100-untreated OT-1 T-cells the day before (FIG. 10). Under these conditions, T-cells again infiltrated both tumors, confirming that CXCR4 antagonism by AMD3100 restores T cell recruitment into tumors expressing high levels of SDF-1 (FIGS. 10C, F).

Quantitation of T-cell infiltration by immunohistochemistry showed that incubation of OT-1 CD8+ T-cells with 0.08

μg/ml or 0.25 μg/ml AMD3100 before adoptive transfer resulted in a highly significant increase in CD3+ T-cell infiltration into B16/OVA.SDF-1-high tumors (101±10.6 and 88.1±16.9 cells/mm$^2$) (p=0.009 and p=0.0111), compared to 40±4.1 cells/mm$^2$ in AMD3100 untreated B16/OVA.SDF-1-high tumors (FIGS. 10M,N,O and I,J,O, respectively). In the same groups of mice, the number of T-cells infiltrating B16/OVA.MSCV tumors (FIGS. 10K, L, and O) was not significantly changed (109±3.2 and 93±14.8) compared to the AMD3100 untreated B16/OVA.MSCV controls (130±13.9 cells/mm$^2$; p=0.098) (FIGS. 10G, H, and O). These data confirm the finding that the primary effect of tumor secretion of SDF-1 is on T-cell infiltration into the tumor- and that a fugetactic effect of the chemokine was abrogated by pretreatment of the tumor antigen-specific T-cells with the CXCR4 antagonist, AMD 3100.

F. Secretion of High Levels of SDF-1 by Tumor Cells Impairs Infiltration and Immune Control by Antigen-Specific Memory T-Cells Having shown that early recruitment of tumor-specific effector T-cells is impaired when SDF-1 is present at high levels in the tumor microenvironment, it was explored whether expression of the chemokine had an effect on the long-term control of SDF-1-expressing tumors. Therapeutic efficacy of adoptively transferred tumor antigen-specific T-cells is dependent, in part, on the ability of donor cells to persist as long-term memory T-cells (Poznansky, M. C., et al. 2000 *Nature Med* 6:543-548. It has also been shown that the response of T-cells to SDF-1 can vary between naïve, effector, and memory CD8+ cells, and that this may be due to the fact that effector CD8+ T-cells express higher levels of CXCR4 than memory T-cells (Rempel, S. A., et al. 2000. *Clin Cancer Res* 6:102-111). Flow analysis of OT-I CD8+ cells after 5 d of in vitro stimulation and expansion showed that 67.2%±9.8 (mean±SEM) of effector cells express CXCR4 compared to 15.5%±1.5 of naïve OT-I cells (data not shown). Whether the recruitment of subpopulations of T-cells to the tumor is dependent on their differential response to SDF-1 was examined in a model where OT-I CD8+ memory cells are established after adoptive transfer. OT-I CD8+ cells generated in vitro persist long after adoptive transfer into syngeneic mice, with the phenotypic and functional characteristics of memory cells. In mice challenged with a thymoma cell line expressing OVA, persistent OT-I CD8+ T-cells showed potent antitumor activity (Bathe, O. F., et al. 2001. *J Immunol* 167:4511-4517). This model also allowed recovery of antigen-specific CD8+ cells and quantification of the level of T-cell infiltration. Twenty-one days following adoptive transfer of 1×10$^7$ OT-I CD8+ T-cells, two groups of mice were challenged s.c. with 2×10$^5$ B16/OVA.MSCV or B16/OVA.SDF-1-high cells. As in the vaccination protocol, adoptively transferred mice showed an initial control of B16/OVA.MSCV, as well as of B16/OVA.SDF-1-high, tumors, as compared to control mice that didn't receive adoptive transfer (FIG. 11A-D). However, 20% of adoptively-transferred mice ultimately developed B16/OVA.MSCV tumors by 60 days after challenge, as compared to 60% of mice challenged with B16/OVA.SDF-1-high tumors (p=0.036; FIGS. 11B, D and E). Intratumoral OT-I CD8+ T-cells from mice that developed tumors were recovered and underwent FACS analysis. The total fraction of intratumoral OT-I CD8+ T-cells was about 7-fold lower in the B16/OVA.SDF-1-high tumor (FIG. 12D) compared to B16/OVA-MSCV tumor (FIG. 12B) (respectively, 0.22%±0.4 vs. 1.7%±0.7, mean±SD). When calculating the total number of CD8+ T-cells expressing the transgenic Vα2-Vβ5.1/5.2 TCR, a 4.5-fold reduction was found in B16/OVA.SDF-1-high compared to B16/OVA.MSCV tumors (respectively, 12±5.4 vs. 55.5±17.6×10$^4$, mean±SD; p=0.005) (FIGS. 12B, D, and E). Analysis of OT-I CD8+ T-cells in the draining lymph node from mice bearing B16/OVA.MSCV or B16/OVA.SDF-1-high tumors, as well as from mice that rejected tumors, showed no significant difference in the fraction of transgenic CD8+ T-cells (p=0.7; FIG. 12E). These data support the view that long-term protection from adoptively transferred OT-I T-cells is overcome when growing tumors express fugetactic concentrations of SDF-1.

Figure 13A:
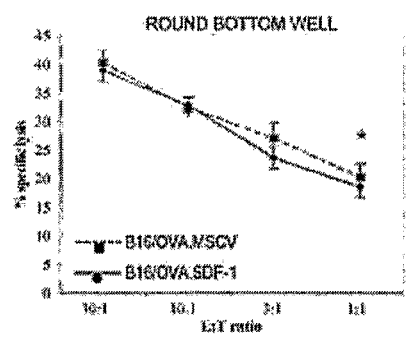
FIG. 13: Quantitation of the cytotoxicity of OT-I CD8+ T cells against B16/OVA.MSCV or B16/OVA.SDF-1 target cells was measured in a standard $^{51}$Cr-release assay (A) or in a previously described modified assay performed in flat bottom wells (B).
Figure 13B:
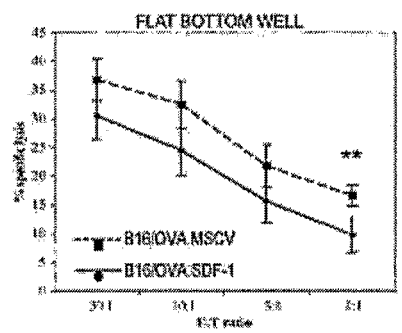
Figure 13C:
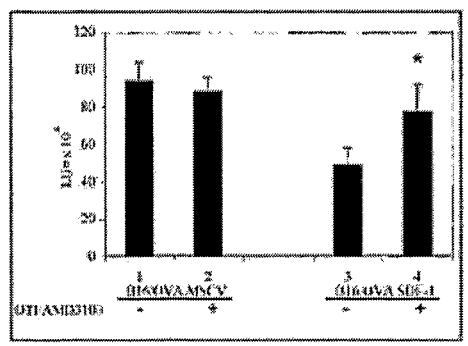

G. SDF-1 Expression at High Levels by Tumor Cells Affects CTL Migration and Cytotoxicity in Vitro High expression of SDF-1 by tumor cells protects them from CTL-mediated lysis in vitro as a result of repulsion of effector cells, mediated via the chemokine receptor, CXCR4. This was demonstrated by a standard $^{51}$Cr release assay, using the OT-I CTLs recognizing H-2K$^b$ MHC I and OVA$_{257-264}$ peptide, and in a recently developed modified assay, which takes account of the influence of effector cell migration on cytotoxicity (Brainard, D. M., et al. 2004. *J Virol* 78:5184-5193). Ova-specific CTLs killed B16/OVA.MSCV cells as effectively as they killed B16/OVA-SDF-1-high cells when target cells were effectively pelleted together in the standard $^{51}$Cr release assay performed in round-bottom wells (FIG. 13A; p=0.16), supporting the view that the production of SDF-1 by tumor cells did not influence the susceptibility of B16/OVA cells in CTL killing. In contrast, when killing activity was quantitated in flat-bottom wells in which the linear density of cells could be decreased and, therefore, the distance between effector and target cell increased, antigen-specific CTLs were significantly less effective at killing B16/OVA cells expressing SDF-1-high as compared to B16/OVA.MSCV cells (FIG. 13B; p=0.0004). To test whether preincubation of OT-I CD8+ T-cells with the CXCR4 antagonist, AMD3100, would restore the killing activity against B16/OVA cells expressing SDF-1, OT-1 CD8+ T-cells were preincubated with the CXCR4 antagonist, AMD3100, at a concentration of 5 μg/ml. This resulted in a significant increase in the killing of B16/OVA.SDF-1-high cells (LU30 of untreated OT-I: 49×10$^6$±9.2 SEM; LU30 of OT-I incubated with AMD3100: 77×10$^6$±15 SEM; p=0.045)(FIGS. 13C and D). These results were generated in experiments in which tumor cells were pulsed with the SIINFEKL peptide, which allows a higher level of specific lysis compared to the level of lysis observed from unpulsed tumor cells. Similar results were observed when killing activity was measured against B16/OVA.MSCV or B16/OVA.SDF-1 cells not pulsed with the peptide (FIG. 14), riling out any difference in OVA expression in the in vivo model.

High-level secretion of SDF-1 by tumors cells, therefore, impairs the efficacy of CTL killing in an assay in which CTL migration plays a critical role. Conversely, blockade of the CXCR4 receptor by the highly specific CXCR4 antagonist, AMD3100, restores the ability of CTL to engage a tumor cell expressing SDF-1-high. These data are consistent with the herein-described finding in vivo that blockade of the CXCR4 receptor by AMD3100 restores the ability of CTL to infiltrate and engage a tumor cell expressing SDF-1 at a high level.

H. Mathematical Modeling of Chemokine Gradients Predict that Chemokine Concentrations in the Tumor Microenvironment Could Induce T-Cell Fugetaxis.

The biological activity of SDF-1 depends on its absolute concentration and the presentation of a gradient of the chemokine within the microenvironment of the tumor. Precise measurements of local concentrations of chemokines in tumors are lacking. A model was established for making predictions about SDF-1 concentrations and gradients in the tumor microenvironment based on measured rates of production of SDF-1 by cells in vitro and SDF-1 degradation in vitro (Dunussi-Joannopoulos, K., et al. 2002. *Blood* 100: 1551-1558).

This model predicts that the SDF-1 concentration within 10 to 50 microns of the periphery of the tumor would be in the range of 0.2 to 0.8 µM for a degradation rate of 6 and 24 hours, respectively. This SDF-1 concentration range has been previously shown to induce fugetaxis of both resting and activated T-cells in vitro and in vivo (Poznansky, M. C., et al. 2000. *Nature Med* 6:543-548).

I. SDF-1 Does not Increase Apoptosis or Impair Activation, Proliferation, and Killing Activity of Stimulated OT-I CD8+ T-Cells Effector OT-I CD8+ cells were incubated for 24 or 72 hours with recombinant SDF-1 to address the question whether the chemokine had a direct pro-apoptotic effect on T-cells. The percentage of apoptotic OT-I CD8+ cells (PI-negative and annexin V-positive) at 24 hours was 7.9±3.07 (mean±SEM) in 10 ng/ml SDF-1, 6.1±3.16 in 100 ng/ml SDF-1, 6.51±2.05 in 1 µg/ml SDF-1. These levels of apoptosis did not differ significantly from those seen with OT-I CD8+ cells cultured without SDF-1 (6.67±3.27) (p=0.94, control versus SDF-1 at 1 µg/ml, data not shown). The fraction of apoptotic T-cells was higher after 72 hour incubation in the presence of 10, 100, or 1000 ng/ml SDF1 (respectively, 19±0.8, 20.3±0.9 and 22.9±0.8%), but the level was not significantly different compared to the fraction of apoptotic cells in the absence of SDF-1 (21.3±1.6, p=0.22, not shown).

Figure 14A:
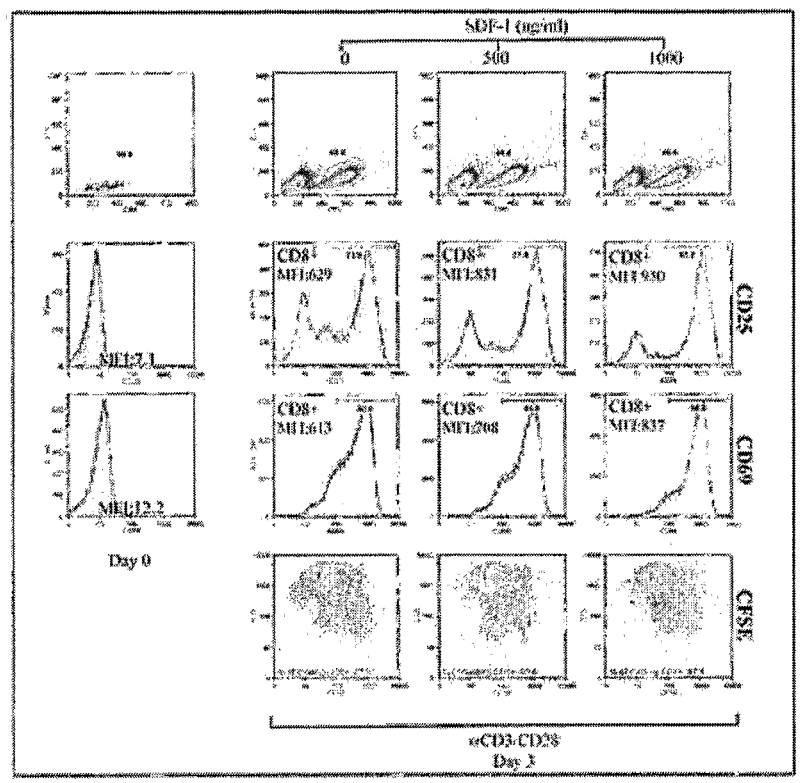
FIG. 14: Effect of SDF-1 on activation, proliferation and killing efficacy of OT-I T cells.

Antibody-induced proliferation of OT-I T-cells was measured in the presence of SDF-1 at chemotactic and fugetactic concentrations (FIG. 14A). The level of CD69 and CD25 expression on OT-1 T-cells after three days of proliferation progressively increased in the presence of SDF-1 at concentrations of 500 and 1000 ng/ml (79.4±3.1 vs 89.3±1.74%, respectively, in the absence or presence of SDF-1 at 1000 ng/ml) (p=0.031) (FIG. 14A and Table 2, below). The level of CD25 also increased from 71.9±1.7 in CTL proliferating in the absence of SDF-1 to 82.5±1.1 in the presence of 1000 ng/ml SDF-1 (p=0.011). The fraction of cells that underwent at least one cell division as evaluated by CFSE was not significantly different in OT-I CD8+ T-cells proliferating in the presence of SDF-1 at 500 ng/ml (95.7±1.3%, average ±S.E.M.) and at 1000 ng/ml (95.2±2.6%), compared to cells proliferated in absence of SDF-1 (95.9±1.9%) (p=0.13) (FIG. 14A and Table 2, below).

TABLE 2

Table 2. Fraction of OT-1 CD8+ T-cells expressing CD25 and CD69 and fraction of cells undergoing cell divisions (as measured by CFSE) after activation in the presence of rSDF-1 at different concentrations (A). Fraction of apoptotic OT-1 CD8+ T-cells (PI-negative and annexin V-positive) activated in the presence of rSDF-1 at different concentrations (B). Killing activity of OT-I CD8+ T-cells exposed to B16/OVA.MSCV or B16/OVA.SDF-1-high cells. OT-1 T-cells proliferated in the lower chamber of a transwell system and B16/OVA.MSCV or B16/OVA.SDF-1-high cells were cocultured in the upper chamber (C). Killing activity is expressed as Lytic Unit 30 (LU30) × $10^6$.

| (A) | rSDF-1 (ng/ml) | | |
|---|---|---|---|
| | 0 | 500 | 1000 |
| CD25 | 71.9 ± 1.77 | 77.4 ± 0.65 | 82.5 ± 1.08 |
| CD69 | 79.4 ± 3.1 | 85.2 ± 1.7 | 89.3 ± 1.74 |
| CFSE (% dividing cells) | 95.9 ± 1.9 | 95.7 ± 1.27 | 95.2 ± 2.6 |

| (B) | rSDF-1 (ng/ml) | | | |
|---|---|---|---|---|
| | 0 | 10 | 100 | 1000 |
| % apoptosis | 21.3 ± 1.69 | 18.5 ± 0.7 | 21 ± 0.98 | 22.9 ± 0.84 |

| (C) | Activation in presence of B16/OVA.MSCV | Activation in presence of B16/OVA.SDF-1-high |
|---|---|---|
| Killing activity against B16/OVA.MSCV | 32.8 ± 3.64 | 31.1 ± 3.5 |
| Killing activity against B16/OVA.SDF-1-high | 30.8 ± 0.9 | 30.5 ± 3.8 |

Figure 14B:
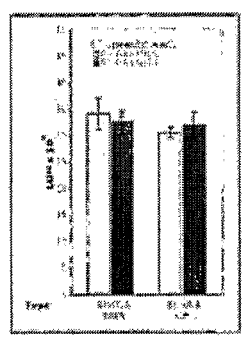

Whether the ability of OT-I CD8+ T-cells to kill B16/OVA cells was affected by the presence of SDF-1 (FIG. 14B, Table 2, above) was also tested. This question was addressed by exposing proliferating OT-I CD8+ T-cells during proliferation in vitro to soluble SDF-1 or to SDF-1 produced by B16/OVA.SDF-1-high cells growing in the upper chamber of a transwell system. As shown in FIG. 14B, OT-I CD8+ T-cells cocultured in the presence of SDF-1-high produced by melanoma cells showed the same level of killing activity against B16/OVA.MSCV or B16/OVA.SDF-1-high target cells compared to the killing activity of T-cells which were exposed to B16/OVA cells not producing rSDF-1 (respectively, p=0.75 and p=0.31). Similar results were observed when incubating OT-I T-cells with soluble SDF-1 (data not shown). Therefore, the activation, proliferation, and functional antitumor activity of tumor-specific T-cells was not impaired by high levels of SDF-1.

Local expression of high levels of SDF-1 by engineered tumor cells abrogates infiltration of the tumor by antigen-specific T-cells. This is the result of the active movement of T-cells away from the chemokine (i.e., fugetaxis) (Poznansky, M. C. 2000. *Nature Med* 6:543-548) SDF-1, eotaxin-3, and the HIV-1 envelope protein gp120 have been shown to repel specific leukocyte subpopulations (Ogilvie, P., et al. 2003. *Blood* 102:789-794, Xiang, Y. Li, et al. 2002. *Nature Neurosci* 5:843-848, and Brainard, D. M. et al. 2004. *J Virol* 78:5184-5193). It has been demonstrated that repulsion of T-cells by high levels of SDF-1 at concentrations in excess of 100 nM is CXCR4-mediated, pertussis toxin-sensitive, phophatidyl inositol-3 kinase-dependent, and that the signaling pathway for T-cell fugetaxis is differentially sensitive to intracytoplasmic cAMP concentrations in comparison to SDF-1-induced T-cell chemotaxis (Poznansky, M. C., et al. 2000. *Nature Med* 6:543-548). SDF-1 acts as a repellent for T-cells at concentrations that are higher than the Kd of SDF-1 for CXCR4 in vitro. This occurs in part because of the previously reported rapid recycling of the wild type CXCR4 receptor to the cell surface and the postulated existence of a low affinity binding site for SDF-1 on CXCR4

(Zlatopolskiy, A., et al. 2001. *Immunol Cell Biol* 79:340-344 and Cyster, J. G. 2002. *J Cl Invest* 109:1011-1012).

Concentration gradients of SDF-1 predicted to be generated in this system in vivo by B16/OVA.SDF-1 cells were mathematically modeled based on measured levels of production and documented degradation rates for SDF-1 in vivo (Poznansky, M. C., et al. 2000. *Nature Med* 6:543-548). This model predicts that SDF-1 concentrations would be high enough at the periphery of the tumor to induce T-cell fugetaxis. The effect on T-cell migration was expected to be predominantly within the local microenvironment of the tumor, in view of the fact that SDF-1 has recently been shown to be inactivated in the bloodstream and in view of its high affinity binding to matrix proteins including fibronectin (Villalba, S., et al. 2003. *J Leukoc Biol* 74:880-888 and Pelletier, A. J., et al. 2000 *Blood* 96:2682-2690).

SDF-1 regulates the local immune response and is a potent chemoattractant for T cells, pre-B lymphocytes, and dendritic cells (Bleul, C. C., et al. 1996. *J Exp Med* 184: 1101-1109 and D'Apuzzo, M., et al. 1997. *Eur J Immunol* 27:1788-1793). The expression of SDF-1 by tumor cells would, therefore, be expected to upregulate an immune response against tumor cells. The data presented herein support the view that SDF-1 may have a bimodal effect on T-cell migration, which includes attraction of T-cells at low concentrations between 10 and 100 nM and repulsion at concentrations of the chemokine above 100 nM. The immune response to tumor cells, which have been engineered by other groups to express SDF-1, has also revealed a dose-dependent effect of the chemokine on this response. Dunussi-Joannopoulos, et al. demonstrated that low expression of SDF-1 (2 ng/ml) secreted at the tumor site by genetically modified B16F1 melanoma cells resulted in delayed tumor growth and supported the development of long-lived tumor-specific CTL responses. However, therapeutic immunity against tumors was not observed when a high number ($>2\times10^5$) of irradiated tumor cells expressing high levels of SDF-1 was used in the vaccination protocol (Dunussi-Joannopoulos, K., et al. 2002. *Blood* 100:1551-1558). Similarly, immunogenic MethA fibrosarcoma and HM-1 ovarian carcinoma secreting high levels of SDF-1 (90 ng/mL and 55 ng/mL, respectively) were able to induce a significant immune response only when tumors were engineered to coexpress IL-2 or granulocyte-macrophage colony-stimulating factor, as well as SDF-1 (Nomura, T., et al. 2001. I 91:597-606). Shrikant, et al. recently reported that antigen-specific T-cells adoptively transferred into mice are able to migrate to the site of tumor challenge where they proliferate and exert lytic activity only for a short time, but that they eventually fail to control tumor growth due to migration away from the tumor bulk. Similarly, Hanson, et al. found that tumor-specific CTL adoptively transferred into mice bearing two CMS5 fibrosarcoma tumors established for 3 or 7 d were able to reject early but not late tumors due to transient lymphocytic presence at the site of tumors (Cyster, J. G. 2002. *J Cl Invest* 109:1011-1012). These data are consistent with recent immunotherapeutic paradigms that predict that early tumors can be rejected by the transfer of tumor-specific T-cells, whereas late tumors are resistant to immune control due to reduced infiltration of tumor-specific T-cells into the tumor itself (Cyster, J. G. 2002. *J Cl Invest* 109:1011-1012). Shown herein is an addition to this model, in which growing tumors initially generate SDF-1 at a level which induces T-cell chemotaxis but ultimately establish an immune privileged site through the activity of high levels of SDF-1 and the repulsion of effector T-cells.

Importantly, abrogation of CXCR4 signaling in tumor-specific CTL by the highly specific CXCR4 antagonist, AMD3100, resulted in restoration of tumor cell lysis, supporting the view that the effects of SDF-1 on CTL repulsion and killing are CXCR4-mediated.

SDF-1 has been shown to promote the adhesion of lymphocytes to endothelial cells via the induction of the intercellular adhesion molecule-1 (ICAM-1). However, increased adhesion of T-cells to vessel walls within tumors expressing high levels of SDF-1 was not evident in either non-immunized or immunized mice in this study. Results presented herein support the view that high-level SDF-1 expression in the tumor microenvironment may result in tight adhesion of a tumor-specific T-cell to the endothelium, but that this is readily followed by SDF-1-mediated repulsion from the tumor. Finally, the concomitant challenge of mice with both control and SDF-1-expressing tumors excludes the possibility of any functional defect of tumor-specific T-cells. Data from combined MRI and immunohistochemical analysis indicate that local dysregulation of the migration of tumor-specific T-cells results in the failure of the immune system to control the growth of SDF-1-expressing tumors.

Tumor cells engineered to express high levels of SDF-1 were examined. Primary human melanoma, ovarian and prostate carcinoma, and glioblastoma have been shown to constitutively express high levels of chemokines including SDF-1 and IL-8 (Scotton, C. J., et al. 2002. *Cancer Res* 62:5930-5938, Barbero, S., et al. 2003. *Cancer Res* 63:1969-1974, Mellado, M., et al. 2001 *Curr Biol* 11:691-696, and Sun, Y. X., et al. 2003 *J Cell Biochem* 89:462-473). Primary tumor cells including melanomas produce up to 25.6 ng/ml (per $1\times10^6$ cells) of SDF-1 in various systems. These rates of production would generate peak chemokine concentrations that are greater than 0.1 µM within and at the periphery of the tumor based on the mathematical model (Mellado, M., et al. 2001 *Curr Biol* 11:691-696).

Chemokines secreted by primary tumors have been shown to play roles in tumorigenesis and the homing of metastasizing tumor cells to specific extratumoral sites in the body. SDF-1 secretion by glioblastoma cell lines or ovarian cancer cells has been shown to lead to an autocrine/paracrine regulation of cell growth via the activation of the ERK1/2 and Akt pathways and the stimulation of DNA synthesis (Scotton, C. J., et al. 2002. *Cancer Res* 62:5930-5938 and Barbero, S., et al. 2003. *Cancer Res* 63:1969-1974). Secretion of high levels of SDF-1 by B16 OVA tumors did not affect tumor cell growth in vitro and in vivo in this study.

In conclusion, these findings further demonstrate the role of this chemokine as a T-cell fugetactic at a high concentration in a novel mechanism of immune evasion by cancer cells. If repulsion of immune cells from high levels of chemokines elaborated in the microenvironment around primary tumors including melanomas contributes to immune evasion, then strategies that overcome this mechanism, including the selective antagonism of chemokine/receptor interactions, will be a useful and novel adjunct to increase the efficacy of cancer vaccines and other anti-cancer immunotherapeutic approaches.

III. Further Description of the Drawings

FIG. 1: SDF-1 expression construct used for transduction of B16/OVA melanoma cells (A). GFP expression in sorted B16/OVA.MSCV and B16/OVA.SDF-1 tumor cells by FACScan analysis (B). B16/OVA.pc: (dotted line); B16/OVA.MSCV: (solid line) B16/OVA.SDF-1: (dashed line).

Western blotting analysis of SDF-1 levels secreted by B16/OVA.SDF-1 cells (lane 4), compared to rSDF-1 50 ng (lane 1), 20 ng (lane 2), 5 ng (lane 3), and B16/OVA.MSCV (lane 5) (C). M: molecular weight marker.

FIG. 2: B16/OVA.SDF-1-high cells were incubated for 24 hours in DMEM containing 0.5% FCS. Conditioned media were then collected and used undiluted, 1:10 diluted or 20× concentrated in transmigration assays. rSDF-1 at concentrations of 100 ng/ml and 1 µg/ml were used as controls. To evaluate chemotaxis (A) and fugetaxis (B), conditioned media were placed in the lower or upper chamber, respectively, and purified murine CD8+ T cells ($6\times10^4$ cells) were added to the upper chamber of each well in a total volume of 150 µl. The chemotactic and fugetactic indices were calculated as the ratio between the number of cells in the experimental setting divided by the number of cells in the control setting in which conditioned media were placed in the upper and lower chambers of the transwell.

FIG. 3: In vitro growth (A) and in vivo tumorigenicity (B) of B16/OVA.pc, B16/OVA.MSCV, B16/OVA.SDF-1 tumor cells. *p=0.13; **p=0.23.

FIG. 4: Non-immunized mice were simultaneously inoculated with B16/OVA.MSCV (■, right flank) and B16/OVA.SDF-1 cells (σ, left flank) (A). Mice (n=8) were sacrificed when at least one tumor reached 200 mm$^2$ in size. Tumor sizes for each mouse at time of sacrifice are shown (B). No significant trend in tumor development was observed in naïve mice (B16/OVA.MSCV vs. B16/OVA.SDF-1 tumors) (p=0.7). Tumor growth was also recorded in mice that were immunized with irradiated B16/OVA.pc (n=8) prior to inoculation with B16/OVA.MSCV (■, right flank) and B16/OVA.SDF-1 cells (G, left flank) (C). Tumor growth was absent in immunized animals B16/OVA.MSCV in 50% of cases and limited the growth of 4/8 B16/OVA.MSCV tumors. All (8/8) B16/OVA.SDF-1 tumors implanted in the opposite flank of each immunized mouse rapidly progressed to 200 mm$^2$ in size (p=0.0001).

FIG. 5: Paraffin-embedded sections of tumors from immunized mice were stained with H&E (A and D) or with polyclonal α-CD3 Ab (B, C, E, and F). Prominent infiltrates of CD3-positive cells were observed in B16/OVA.MSCV tumors (B and C), but not in tumors expressing SDF-1 (E and F). (Magnification=40× or 200×).

FIG. 6: Mice (groups of 5) were prophylactically immunized with irradiated B16/OVA.SDF-1-high cells prior to inoculation with B16/OVA.SDF-1-low (●, right flank) and B16/OVA.SDF-1-high cells (σ, left flank) (B). Non-immunized mice were challenged bilaterally with both tumors as control (A). 40% of mice did not develop the B16/OVA.SDF-1-low tumors implanted in the right flank (B). All mice showed growth of the B116/OVA.SDF-1-high tumors in the left flank (p=0.021) (B). No significant difference in tumor development was observed in naïve mice (A; p=0.88). α-CD3 staining of tumor sections showed T-cell infiltrates in B16/OVA.SDF-1-low tumors but not in tumors expressing high levels of SDF-1 (C; *p=0.007).

Figure 7:
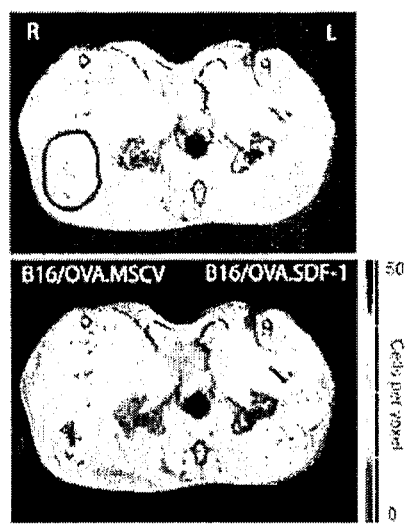
FIG. 7: Early recruitment of CLIO-tat labelled OT-I CD8+ T cells is impaired in B16/OVA tumors expressing SDF-1.

FIG. 7: Early recruitment of CLIO-tat labeled OT-I CD8+ T-cells is impaired in B16/OVA tumors expressing SDF-1. Axial MRI slices through mouse thighs showed a significant signal reduction in the B16/OVA.MSCV tumor compared to the B16/OVA.SDF-1 tumor, indicating that more labeled OT-I T-cells had been recruited into the B16/OVA.MSCV tumor. The intensity of T-cell recruitment corresponding to dark areas (A) is also shown as a T2 spectral color map (B). Number of cells/voxel is indicated in the color scale. The result shown is representative of four independent experiments.

FIG. 8: Immunohistochemical studies of T-cell infiltration in B16/OVA tumors correlates with MR imaging. Tissues were collected 48 hours after adoptive transfer and sections stained with H&E (A,D) or with polyclonal anti-CD3 Ab (B,C,E,F). Numerous CD3+ T-cells were present within the B16/OVA.MSCV tumor (B,C). In contrast, very few CD3+ T-cells could be detected in the B16/OVA.SDF-1 tumor (E,F). Results are representative of 6 independent experiments. Quantitation of CD3+ cell infiltration into tumors was performed. The mean number (+/−SD) of CD3+ cells per mm$^2$ from six animals is shown. (G). Magnification=40× or 200×. *: p=0.018.

FIG. 9: Two groups of mice (n=3) were challenged with B16/OVA.MSCV cells in the right (R) flank and with B16/OVA.SDF-1-low or SDF-1-high cells in the left (L) flank. After 48 hours from adoptive transfer of OT-1 CD8+ T-cells, tumors were collected and sections stained with polyclonal anti-CD3 Ab. A significantly higher number of tumor infiltrating CD3+ cells was found in B16/OVA.SDF-1-low compared to B16/OVA.MSCV tumors. As expected, mice bearing B16/OVA.MSCV and B16/OVA.SDF-1-high tumors showed a T cell infiltrate in the B16/OVA.MSCV, but not in the B16/OVA.SDF-1-high, tumor. The mean number (+/−SD) of CD3+ cells per mm$^2$ from three animals is shown. *: p=0.032; **: p=0.005.

FIG. 10: CLIO-tat-labeled activated OT-1 CD8+ T-cells were incubated with PBS (A,D) or AMD3100 (0.08 and 0.25 µg/ml)(B,E and C,F) prior to adoptive transfer into mice bearing bilateral B16/OVA.MSCV and B16/OVA.SDF-1-high tumors. Axial MRI shown in this figure were generated 24 hours after adoptive transfer. Panels C and F show MR images of a representative mouse (#1), that initially received T-cells untreated with AMD3100 and subsequently received a second adoptive transfer with AMD3100-treated OT-1 CD8+ T-cells 24 hours from the first one. MRI images were obtained again at 24 hours after this second adoptive transfer. Significant T2 reduction was observed in B16/OVA.MSCV as compared to B16/OVA.SDF-1-high tumors (D: low T2 fit value ratio). Equivalent T2 reduction was seen when OT-1 T-cells were preincubated with AMD3100 with equivalent infiltration of T-cells into B16/OVA.MSCV and B16/OVA.SDF-1-high tumors (E; T2 fit value close to 1). As expected, a second adoptive transfer of AMD3100-pretreated OT-1 CD8+ T-cells performed to mouse 1 showed a bilateral T2 signal reduction (F; T2 fit value close to 1). Tissues were collected 48 hours after adoptive transfer and stained with anti-CD3 Ab (G-J; AMD3100 untreated and K-N; AMD3100 treated). The mean number (+/−SD) of CD3+ cells per mm$^2$ from three animals per group after adoptive transfer of OT-1 T-cells pretreated with AMD3100 at 0.08 and 0.25 ng/ml concentration is shown (O). Magnification=40 and 100×. * p=0.098; ** p=0.011.

FIG. 11: Potent antitumor activity of persistent adoptively transferred OT-I CD8+ cells is overcome when SDF-1 is locally expressed. Groups of mice (n=6) were challenged with B16/OVA.MSCV (A and B) or B16/OVA.SDF-1 (C and D) cells 21 d after intravenous (i.v.) adoptive transfer of $1\times10^7$ OT-I CD8+ T-cells. Control mice were challenged 21 d after i.v. HBSS alone (A and C). Tumor growth (A-D) and the survival analysis (E) are shown. 35% of B16/OVA.SDF-1-bearing mice (D and E) rejected the tumor, compared to 90% of mice that were challenged with B16/OVA.MSCV tumors (B and E). *: p=0.04.

FIG. 12: FACScan identification of adoptively transferred OT-I CTL from recovered tumors and lymph nodes (LN). Each dot plot reports the mean fraction (±SD) of CD8+ cells expressing Vβ5.1/5.2 and Vα2 TCR in the total number of B16/OVA.MSCV or B16/OVA.SDF.1 tumor cells analyzed, from control (A and C) and adoptively transferred mice (B and D). The number of persistent OT-I CD8+ cells in each tumor and in 2 draining LN was determined (E). AU mice had OT-I CD8+ T-cells in LN without any significant difference between groups bearing B16/OVA.MSCV or B16/OVA.SDF-1 tumors (p=0.7). The total number of OT-I CTL in SDF-1-expressing tumors was significantly reduced 4-fold compared to cells recovered from B16/OVA.MSCV tumors (*: p=0.005). Results are expressed as the mean+/− SD from three independent experiments and three or four mice per group.

FIG. 13: Quantitation of the cytotoxicity of OT-I CD8+ T-cells against B16/OVA.MSCV (■) or B16/OVA.SDF-1 (●) target cells was measured in a standard 51Cr-release assay (A) or in a previously described modified assay performed in flat-bottom wells (B). (*: p=0.16, **: p=0.0004). Results of six independent experiments are shown. Cytotoxicity of OT-I CD8+ T-cells pretreated with the specific CXCR4 antagonist, AMD3100 (5 µg/ml) (lanes 2 and 4), or untreated (lanes 1 and 3) and incubated with B16/OVA.MSCV (lanes 1 and 2) or B16/OVA.SDF-1 (lanes 3 and 4) was also assessed in $^{51}$Cr-release assays in flat-bottom wells (C). Results are reported as $LU_{30}/10^6$ OT-I cells, and data are shown as mean±SEM. (*: p=0.045). Results representing mean values+/−SEM from three independent experiments are shown.

FIG. 14: Effect of SDF-1 on activation, proliferation, and killing efficacy of OT-I T-cells. Splenocytes or purified CD8+ T-cells from OT-I mice were preincubated for 3 hours with SDF-1 at two indicated concentrations. Cells were proliferated for three days in 96-well plates in the presence of bound anti-CD3, soluble anti-CD28, and 50 U/ml IL-2, and SDF-1 at the indicated concentration was added to each culture every 24 hours (A, upper color dot plots). For analysis of T-cell activation, cells were labeled with anti-CD25 (red histograms), anti-CD69 (A, blue histograms). Proliferation was measured after 3 days stimulation in CFSE-prelabeled T-cells (A, lower color dot plots). The killing activity of OT-I CD8+ T-cells was evaluated after antibody-induced proliferation of T-cells for 5 days in the presence of B16/OVA-MSCV or B16/OVA.SDF-1 cells growing in a 0.4 µM pore polycarbonate membrane placed in the upper chamber from the first day of culture (B). The killing activity of OT-I CD8+ T-cells stimulated in the presence or absence of SDF-1 was measured against B16/OVA.MSCV or B16/OVA.SDF-1 target cells (not pulsed with SIINFEKL peptide) in round-bottom well plates after 5 hours incubation with the chemokine.

Example II: Emigration of CD4 Cells from the Fetal Thymus is Abrogated by the Anti-fugetactic, CXCR4Antagonist AMD3100

Developing thymocytes undergo maturation whilst migrating through the thymus and, ultimately, emigrate from the thymus to populate peripheral lymphoid organs. The process of thymic emigration is controlled in part by the receptor/ligand interaction between SDF-1 and its cognate receptor CXCR-4. The precise mechanism by which CXCR4/SDF-1 contributes to thymic emigration has now been determined to be regulated by a CXCR4-dependent fugetactic signal that can be abrogated by the anti-fugetactic agent AMD3100.

I. Materials and Methods

A. Mice

E15.5 CXCR4$^{-/-}$ embryos were generated by breeding CXCR4-deficient heterozygous mice on a C57BL/6 background. Presence of the vaginal plug was considered to represent gestational day 0.5. Mice and embryos were genotyped as previously described (Ma, Q., et al. 1998. *Proc Natl Acad Sci USA* 95:9448; Ma, Q., et al. 1999. *Immunity* 10:463). Mice used in the study described in the present part were bred in a pathogen-free facility, in accordance with NIH animal research guidelines.

B. Fetal Thymus Organ Culture

Pregnant females at day 15.5 of gestation were sacrificed by $CO_2$ asphyxiation, and embryos were chilled on ice. Fetal thymuses were carefully removed under a dissecting microscope, taking care to keep the anatomically identifiable lobes joined together. Thymuses were placed in HBSS and kept on ice. Individual thymuses were gently transferred onto the surface of a polycarbonate membrane of a 6.5 mm transwell insert with a 3.0 µm pore size (Corning Incorporated Life Sciences Acton, Mass.). DMEM (360 µl) supplemented with 2 mM glutamine, 100 U/ml penicillin, 100 µg/ml streptomycin, $2×10^{-5}$ M 2-mercaptoethanol, 0.1 mM non-essential amino acids, 10% HEPES, and 10% FBS (Sigma) was added to the lower chamber of the transwell. This amount of medium allowed the thymus to be at the interface of medium and air. The cultures were incubated at 37° C. in 5% CO, and medium was replaced every 3 days. Thymic emigrants were collected from each thymus by transferring each transwell insert containing one thymus onto to a new well 24 hours before harvesting emigrants present in the lower chamber for analysis. On the day of analysis, two thymuses were harvested, and emigrants were pooled from at least 4 thymic lobes from CXCR4$^{+/-}$ and CXCR4$^{-/-}$ mice. For each time-point, CXCR4$^{+/-}$ and CXCR4$^{-/-}$ thymuses from one or two pregnant females bred at the same time were analyzed, aiming to minimize differences in the stage of maturation and total cell recovery. E15.5 WT (CXCR4$^{+/+}$) thymuses were obtained from fetuses from C57BL/6 mice breedings. For inhibition studies on thymic emigration, PTX (100 ng/ml, Sigma) or murine recombinant SDF-1 (50, 500, 1000 nM, PeproTech, Rocky Hill, N.J.) was added to WT FTOC at day 14 and thymus and emigrants were harvested at day 15 of culture (Poznansky, M. C., et al. 2002. *J Clin Invest* 109:1101). FTOC from DPC 15.5 CXCR4+/− or CXCR4−/− embryos were also prepared as above, and AMD3100 (0.5 or 1 gg/ml; Sigma) was added to the lower chamber of day 14 FTOC. Thymic emigrants were then collected after 24 hours (Hatse, S., et al. 2002. *FEBS Lett* 527:255).

C. Immunofluorescence Staining and Flow Cytometric Analysis

Thymic lobes were harvested and transferred to a 4-ml round bottom polystyrene tube containing 0.4 mg/ml collagenase (from *Clostridium histolyticum*, type V, clostridiopeptidase A, SIGMA Chemicals), 10% FBS, EDTA 0.2 mg/ml and 0.2 M phosphate. After 30 minutes incubation at 37° C., thymuses were disaggregated by gentle pipetting until no visible fragments remained. Cell suspensions were washed once in HBSS and 10% FBS to prevent further enzyme action. Cells were resuspended in PBS containing 0.1% bovine serum albumin and counted using a hemocytometer. After incubation for 30 minutes on ice with 0.5 gg of 2.4G2 antibody to block Fc binding, direct staining for three or four color analysis was performed. Cell suspensions were incubated for 15 minutes at 4° C. and then washed twice with staining buffer and analyzed using a FACSCalibur (BD Biosciences). Data analysis was performed with FlowJo software (Tree Star, Inc. Ashland, Oreg.). The following monoclonal antibodies were used: Anti-CD4 (clone RM4-5), anti-CD8 (clone 53-6.7), anti-CD62L (clone MEL-14), anti-CD3c (clone 145-2C11), and anti-CXCR4 (clone 2B11/CXCR4), (BD PharMingen, Mountain View, Calif.). For annexin V and PI staining, an Annexin V-FITC Apoptosis Detection Kit I was used (BD Pharmingen). For each marker, the threshold of positivity was found beyond the non-specific binding observed in the presence of irrelevant control antibody. Mean log fluorescence intensity (MFI) values were obtained by subtracting the MFI of the isotype control from the MFI of the positively stained sample. To evaluate whether the differences between the peaks of cells were statistically significant with respect to controls, the Kolmogorov-Smirnov test for analysis of histograms was used.

D. Transmigration Assays

Quantitative transmigration assays were performed using a transwell system (Corning Costar Inc., Corning, N.Y., USA) (6.5-mm diameter, 5-μm pore size, polycarbonate membrane) as described previously (Poznansky, M. C., et al. 2000. *Nat Med* 6:543). Purified fetal (E.16) thymocyte subpopulations ($5 \times 10^4$ cells) (double negative (DN), double positive (DP) and single positive (SP) thymocytes were prepared by FACS sorting as previously described (Poznansky, M. C., et al. 2002. *J Clin Invest* 109:1101) and were added to the upper chamber of each well in a total volume of 150 gL of DMEM containing 0.5% FCS. Cell populations were shown to be >99.9% pure by flow cytometric analysis (data not shown). Human SDF-1 (PeproTech Inc., Rocky Hill, N.J., USA) was used at concentrations of 100 ng/ml, 1 and 10 gg/ml in the lower, upper, or both lower and upper chambers of the transwell to generate a checkerboard analysis matrix of positive, negative, and absent gradients of SDF-1, respectively. Thymocyte subpopulations were also pretreated with PTX (100 ng/ml) or anti-CXCR4 monoclonal antibody (10 μg/ml) as previously described and prior to addition into the transmigration assay (Poznansky, M. C., et al. 2002. *J Clin Invest* 109:1101).

II. Results

A. The CXCR4 Antagonist AMD3100 Impairs Normal CD4 Cell Emigration from Fetal Thymus Organ Culture (FTOC)

The specific non-peptide CXCR4 antagonist, AMD3100, a bicyclam derivative first described for its potent activity against HIV infection (Hatse, S., et al. 2002. *FEBS Left* 527:255; De Clercq, E., et al. 1992. *Proc Natl Acad Sci USA* 89:5286), has been shown to inhibit intracellular Ca+ flux and chemotactic responses of murine splenocytes to SDF-1 (Matthys, P., et al. 2001. *J Immunol* 167:4686). CXCR4 expression was measured in SP and DP thymocytes from day 14 FTOC (not shown). As expected, CXCR4 was expressed at a higher level in DP thymocytes (MFI $52.1 \pm 11.3$) compared to SP cells. SP CD4 thymocytes showed significantly higher expression of CXCR4 compared to SP CD8 cells (MFI $29.1 \pm 6.5$ vs. $15.5 \pm 7.3$, respectively, $p=0.01$). FTOC at day 14 of culture were incubated for 24 hours with 1 μg/ml of AMD3100. Treatment of FTOC with 1 μg/ml AMD3100 significantly increased the total number of cells in the thymus as compared to untreated FTOC (FIG. 15A; $349 \pm 99.5$ vs. $247 \pm 72.9 \times 10^3$/lobe, respectively, $p=0.022$). The total number of SP CD8 emigrants did not differ between AMD3100-treated and untreated FTOC ($p=0.93$). However, in contrast, SP CD4 thymocytes were severely impaired in their ability to emigrate from AMD3100-treated thymuses as compared to untreated controls (FIGS. 15A, C, $1.1 \pm 0.15$ vs. $4.07 \pm 0.12 \times 10^3$/lobe, respectively; $p=0.005$).

Analysis of CD62L expression revealed that retention of $CD62L^{high}$ CD4 SP cells in the thymus of AMD3100-treated FTOC had occurred in comparison to untreated CXCR4+/+ thymuses (FIGS. 15B, D; $p=0.017$). CD62L expression by SP CD8 thymocytes was not affected in AMD3100 treated thymuses (FIGS. 15B, D; $p=0.56$). In effect, blockade of the CXCR4 receptor in normal thymocytes by AMD3100 led to the retention of mature T cells in the thymus, in vitro and in vivo. Thus, the anti-fugetactic agent AMF3100 also works to inhibit fugetaxis of T cells emigrating from the thymus.

III. Further Description of the Drawings

FIG. 15: CXCR4$^{+/-}$ E15.5 FTOC (n=4) were cultured for 14 days and then treated for 24 hours with 1 μg/ml AMD3100. Thymic cells and RTE were collected and stained for CD4 and CD8 (A, C) and CD62L (B, D). The absolute number (mean±SEM) of SP CD4 and CD8 RTE (C, *p=0.005) and the fraction (mean±SEM) of $CD62L^{high}$ SP intrathymic thymocytes (D, **p=0.017) from AMD3100-treated and untreated FTOC are shown.

Example III: Protein Kinase C Inhibitors Have Anti-Fugetactic Effects on Neutrophils Neutrophil chemotaxis can serve as a prototype for understanding higher eukaryotic cell migration and gradient sensing (Iijima, M., et al. 2002. *Dev Cell* 3:469-78; Parent, C. A., et al. 1999. *Science* 284:765-70). It is well established that neutrophils undergo chemoattraction, or persistently directionally biased movement towards a number of chemokinetic agents elaborated at sites of tissue injury, including the chemokine IL-8 (Baggiolini, M., et al. 1992. *FEBS Lett* 307:97-101; Rot, A. 1993. *Eur J Immunol* 23:303-6; Luster, A. D. 1998. *N Engl J Med* 338:436-45). It has now been determined that neutrophil fugetaxis can be abrogated by anti-fugetactic Protein Kinase C inhibitors such as GF109203X.

I. Materials and Methods

A. Neutrophil Isolation

Human whole blood was obtained from healthy volunteers by venipuncture into tubes containing sodium heparin (Becton Dickinson, San Jose, Calif.). Neutrophils were isolated by density gradient centrifugation and purified by hypotonic lysis, as previously described (Tager, A. M., et al. 1998. *Am J Respir Cell Mol Biol* 19:643-52).

B. Fabrication, Preparation, and Characterization of Microfluidic Linear Gradient Generator The microfluidic linear gradient generators were fabricated in poly(dimethylsiloxane) (PMDS; Sylgard 184, Dow Corning, N.Y.), and gradient generation was verified with fluorescin isothiocyanate (FITC; Sigma-Aldrich), as previously described (Li Jeon, N., et al. 2002. *Nat Biotechnol* 20:826-30; Whitesides, G. M., et al. 2001. *Annu Rev Biomed Eng* 3:335-73).

C. Microfluidic Migration Assay and Time-Lapse Microscopy

Neutrophils at a concentration of $5 \times 10^6$ cells/ml were loaded uniformly across the migration channel and allowed to migrate in the absence or presence of a linear gradient of human Interleukin-8 (72 amino acids; Pepro-Tech, Rocky Hill, N.J.) in Iscove's Modified Dulbecco's Medium (IMDM; Mediatech, Herndon, Va.) with 0.5% (w/v) fetal bovine serum (FBS; Mediatech) flowing at 0.1 mm/sec, with peak concentrations of 12 nM, 120 nM, and 1.2 μM.

Migration was observed in a Nikon Eclipse TE2000-S microscope (Nikon, Japan). Brightfield images (10×) were taken every 30 seconds using a digital camera (Hamamatsu, Japan) controlled by IPLab 3.6.1 (Scanalytics, Fairfax, Va.). Cell movement and gradient verification were always observed at a set point along the migration channel. Secondary effects of chemokinetic agents secreted by cells during the course of the experiments were effectively ruled out previously and were considered unlikely in view of the flow rate of fluid through the device throughout the assay. In certain experiments, cells were pre-incubated with GF109203X (25 mM for 30 minutes at 25° C.), and then washed and loaded into the device.

D. Mathematical Analysis of Cell Migration in Linear Gradient Generator

Cell movement was tracked using MetaMorph 4.5 (Universal Imaging, Dowington, Pa.) object tracking application, which generated tables of Cartesian coordinate data for each cell. Tracking data was analyzed in Excel (Microsoft, USA) and MATLAB 13 (The Mathworks, Inc., Nowton, Mass.) to determine angular frequencies, mean squared displacements, migration velocities, persistence times, random motility coefficients, and random walk path lengths. Cell movement was characterized based on a persistent random walk model as follows (Moghe, P. V., et al. 1995. *J Immunol Methods* 180:193-211; McCutcheon, M. 1946. *Physiological Reviews* 26:319). For each cell, the squared displacement R(t) was calculated at time interval t, $$R^2(t)=(x(t_0+t)-x(t_0))^2+(y(t_0+t)-y(t_0))^2, \quad (1)$$

where $t_0$ is the time at the origin. The origin was shifted along the data set and the displacements were averaged for overlapping time intervals. A global average was performed over all cells in the set to calculate the mean squared displacement. Mathematically modeling cell movement as a correlated, biased random walk, this can be written as $$R^2(t)=2S^2P[t-P(1-e^{-t/P})], \quad (2)$$

where S and P are measures of the mean speed of movement and persistence time respectively. When time interval t is much greater than persistence time P, the mean squared displacement becomes linearly proportional to 1, analogous to Brownian diffusion, $$R^2(t)=2S^2Pt=4\mu t3, \quad (3)$$

where μ is the motility coefficient. The slope and intercept of a least squares regression fitted to the linear section of the mean squared displacement give an estimate of μ and P, respectively. Further, a "persistence index" (PI) of the motion or mean free path, was calculated as the total displacement of the cell divided by the total path length. The PI is an indicator of turning behavior, with 1 indicating motion in a straight line and 0 indicating no net displacement. To quantify directional bias of neutrophil migration in defined IL-8 gradients in microfabricated devices, we calculated a "chemotropism index" (CI) based on McCutcheon, et al. (Mc Cutcheon, M. 1946. *Physiological Reviews* 26, 319; Nossal, R., et al. 1976. *Biophys J* 16, 1171-82) and defined as the net path length traversed by a cell with respect to the direction of the established gradient divided by the total distance traveled and modified to include a measurement of directionality towards or away from the maximal chemokine concentration:

$$CI = \frac{\sum l_i \cos\varphi_i}{\sum l_i} \quad (4)$$

where, li is the length of a cell's movement vector and $\varphi_i$ is the angle the movement vector makes with respect to the established gradient. The CI is therefore an indicator of accuracy of orientation with respect to the gradient and will be 1 if a cell moved directly up the gradient, 0 if there is no preferred orientation, and −1 for migration directly down the gradient. The index was calculated for each cell and then averaged over the population of migrating cells to obtain the "mean chemotropism index" (MCI).

II. Results

A. Protein Kinase C Inhibitor GF109230X Impacts Neutrophil Migration

In an effort to determine if Protein Kinase C (PKC) secondary messenger signal amplification or dampening could control directional bias of neutrophil fugetaxis, and in light of the finding that calcium-dependent PKCs have been shown to be involved in directional cell migration (Jin, M. et al. 2005. *J Neurosci* 25:2338-47; Sun, X. G., et al. 1999. *Cell Growth Differ* 10:343-52; Battle, E., et al. 1998. *J Biol Chem* 273:15091-8; Carnevale, K. A., et al. 2003. *J Biol Chem* 278:25317-22), neutrophils were pretreated with the selective calcium-dependent PKC inhibitor, GF109203X (Toullec, D., et al. 1991. *J Biol Chem* 266:15771-81), and then exposed to gradients of IL-8 in which neutrophil fugetaxis (600 nM to 1.2 mM) or chemoattraction was predominant (0 to 120 nM). GF109230X at a concentration of 25 μM selectively inhibited fugetaxis and converted a fugetactic response into a predominantly chemoattractant response (FIG. 16) (p<0.0001). Thus, PKC inhibitors also function as anti-fugetactic agents.

III. Further Description of the Drawings

Figure 16:
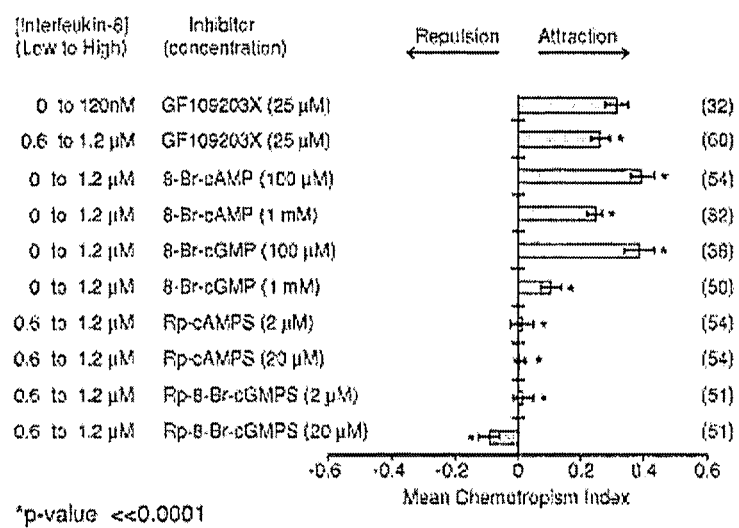
FIG. 16: Mean chymotrypsin index (MCI) calculated for each IL-8 gradient in the presence of GF109203X, 8-Br-cAMP, Rp-cAMPS, or Rp-8-Br-cGMPS.

FIG. 16: The mean chemotropism index (MCI) (+/− standard error) for each indicated condition are shown for each IL-8 gradient condition including in the absence or presence of an IL-8 gradient in the presence of GF 109230X, 8-Br-cAMP, 8-Br-cGMP, Rp-cAMPS, and Rp-8-Br-cGMPS. The number of cell tracks analysed to generate the MCI are shown in brackets to the right of the figure and are derived from triplicate experiments for each condition. MCI values less than −0.1 indicate directionally biased down the gradient (fugetaxis) and MCI values greater than +0.1 indicate directionally biased movement up the gradient (chemotaxis or attraction). †p<0.005 or *p<<0.0001: Student t text comparison of MCI for each inhibitor condition as compared to the relevant control gradient without inhibitor.

Example IV: Assay for Fugetactic and Anti-Fugetactic Agents

T-cells are repelled by fugetactic agents in a concentration-dependent manner. In culture, repulsion of T-cells by fugetactic agents results in the formation of a zone of clearance around the cells. When pre-treated with an anti-fugetactic inhibitor, the zone of clearance does not form around T-cells despite the presence of the fugetactic agent. Accordingly, a binary assay for fugetactic and anti-fugetactic agents is described herein.

I. Materials and Methods

A. Formation of SDF-1 Gradients

For the analysis of T-cell responses in SDF-1 gradients generated by β-TC3 cells, murine T-cells were added to microwells with SDF-1 secreting and control β-TC3 cells, preliminary grown as round 6 mm patches on fibronectin or laminin coated 24-well and 48-well plates (BD BioSciences, Bedford, Mass.), incubated for 15 hours at 37° C. and observed using timelapse videomicroscopy. Images were taken every 30 seconds using a Hamamatsu camera (Hamamatsu, Japan) controlled by IPLab software. The CXCR4 receptor was blocked by pre-incubation of T-cells with 5 μg/ml AMD3100 (Sigma, St. Louis, Mo.) for 30 min at 37° C. as previously described (70). Trajectories of migration were determined for randomly selected T-cells using Metamorph software. Cell path tracking and mean chemotropic indices (MCI) as a measurement of directionality of movement towards or away from β-TC3 cells were calculated using MetaMorph and MatLab software as previously described where an MCI of +0.1 to −0.1 indicates chemokinesis, >+0.1 indicates chemotaxis and <−0.1 indicates fugetaxis (Moghe, P. V., et al. 1995 *J Immunol Methods* 180, 193-211; Mc Cutcheon, M. (1946) *Physiological Reviews* 26, 319).

II. Results

An assay allowing examination of the fugetactic effect of a steep continuous SDS-1 gradient on T-cell migration has been designed, where T-cells were added to MSCV.SDF-1 bright cells or control cells and their active movement observed directly for 15 hours using time-lapse microscopy. T-cells were evenly distributed within the wells with control MSCV cells as well as SDF-1 secreting MSCV.SDF-1 bright cells at the beginning of experiments. In the wells with control cells, distribution of T-cells remained random by the end of the experiment and cell migration was documented to be chemokinetic in nature by time-lapse video microscopy and by cell path tracking and MCI (−0.018+/−0.012) (FIGS. 17A and D). In contrast, T-cells migrated away from MSCV.SDF-1 bright cells and formed zones of clearance of T-cells around the patches of SDF-1 secreting cells at 15 hours of incubation. T-cells tended to migrate towards SDF-1 secreting cells during the first 1.5 hours of incubation (MCI=+0.08+/−0.018) but subsequently changed to a fugetactic response (MCI=−0.268+/−0.019) (FIGS. 17B and E). To confirm that fugetaxis of T-cells was directly related to SDF-1 secretion by MSCV.SDF-1 bright cells, T-cells were pretreated with the specific CXCR4 antagonist AMD3100. T-cells treated in this way failed to migrate away from SDF-1 secreting cells and remained randomly distributed around MSCV.SDF-1 bright cells (FIG. 17C). In this way, it has been shown that MSCV.SDF-1 bright cells and not control. MSCV cells elicited migrational responses from T-cells, and that the high level of SDF-1 secretion by MSCV.SDF-1 bright cells was sufficient to repel T-cells in vitro via a CXCR4 mediated mechanism.

III. Further Description of the Drawings

Figure 17:
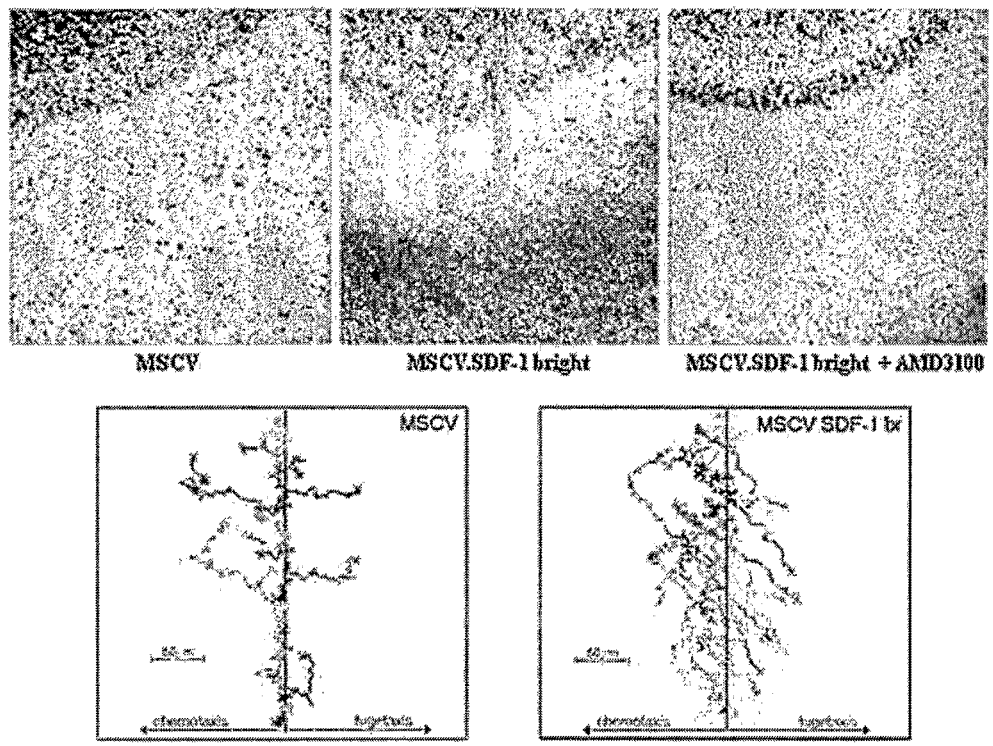
FIG. 17: Demonstration of T-cell fugetaxis from MSCV.SDF-1 bright cells producing high levels of SDF-1 using time-lapse microscopy.

FIG. 17: Demonstration of T-cell repulsion from MSCV.SDF-1 bright cells producing high levels of SDF-1 using time-lapse microscopy. Pan-T cells were randomly distributed in the wells with control MSCV or MSCV.SDF-1 bright cells and incubated for 15 hours. FIGS. 24a-24c represent final distribution of T-cells by the end of experiment, which remained random in the wells with control MSCV cells (A) and MSCV.SDF-1 bright cells when T-cells were pretreated with CXCR4 antagonist AMD3100 (C), whereas the repulsion of untreated T-cells from MSCV.SDF-1 bright cells producing high levels of SDF-1 cells resulted in formation of a "clearance zone" (B). FIG. 17D-E represent migratory paths of untreated T-cells observed within first 2.5 hours of co-incubation with control MSCV (D) or MSCV.SDF-1 bright cells (E). The start points of migration tracks are distributed along the axis, the end points are marked with crosses. In the control MSCV wells T-cell migration was chemokinetic by nature whereas in the wells with MSCV.SDF-1 bright cells T-cells migration was chemotactic towards SDF-1 secreting cells within first hour but subsequently changed to fugetactic.

Example V: Fugetactic Effects of Ligand Dimerization

High levels of intracytoplasmic calcium flux in neutrophils are shown herein to be associated with the fugetactic action of chemokines. Drawing parallels between these conditions of intracytoplasmic calcium flux and the conditions under which the fugetactic agents IL8 and SDF-1 are dimerized indicates that such agents are dimerized when mediating their fugetactic effects.

I. Materials and Methods

A. Materials and methods for the isolation of neutrophils are described in Part I of Example III, above.

B. Intracellular Calcium Measurements and CXCR2 staining following IL-8 105

Calcium flux in neutrophils in response to IL-8 was measured as previously described (Mahon, M. J., et al. 2004 *J Biol Chem* 279:23550-8). Briefly, isolated cells (~$10^7$/ml) were transferred into a balanced salt solution (127 mM NaCl, 3.8 mM KCl, 1.2 mM $KH_2PO_4$, 1.2 mM $CaCl_2$, 0.8 mM $MgCl_2$, 5 mM glucose, and 10 mM HEPES, pH 7.4), incubated for 45 min at room temperature with 1.25 μM Fura-2 acetoxymethyl ester (Molecular Probes, Eugene, Oreg.), washed with the balanced salt solution, and unloaded for 15 min at room temperature. Cells were then washed twice with the balanced salt solution, resuspended at $10^6$/mL, and plated in Lab-Tek II chambered cover glass (Nalge Nunc International, Naperville, Ill.). Calcium flux in response to indicated concentrations of IL-8 (Akahoshi, T., et al. 1994 *Lymphokine Cytokine Res* 13:113-6) was measured by fluorescence of cells excited at 340 and 380 nm using a PTI Deltascan dual-wavelength fluorimeter (Photon Technologies Incorporated, Lawrenceville, N.J.), observed through a Nikon Diaphot 200 microscope (Melville, N.Y.) and Sensys charge-coupled device camera (Photometrics, Ltd., Tucson, Ariz.), and analyzed using the Poenie-Tsien ratio with Imagemaster 2 software (Photon Technologies Incorporated). Signaling responses to IL-8 at designated concentrations were calibrated against maximal calcium flux as determined by treatment with 5 μM ionomycin (Sigma). CXCR2 expression on neutrophils pre- and post-exposure to 120 nM, 1.2 μM and 2.4 μM IL-8 was determined using PE-labelled anti-CXCR2 IgG1 antibody (R & D systems). Neutrophils were also stained with a PE-labelled IgG1 isotype control antibody to quantify non-specific staining. Mean fluorescent intensity (MFI) was determined using FloJo software (Tree Star, San Carlos, Calif.). Statistical differences between MFI values generated from isotype control staining and specific CXCR2 staining under experimental conditions was determined by Kolmogrov-Smirnoff test.

II. Results

A. Low and High Concentrations of IL-8 Generate Differential Levels of Calcium Flux Measurement of intracellular calcium flux serves as an indicator of the magnitude of signal transduction by a GPCR, and both calcium and cyclic nucleotides can serve as secondary messengers of these signals. In order to ascertain whether signaling output could be generated by chemotactic and fugetactic IL-8 doses, cells were loaded with 1.25 µM Fura2-AM, exposed to 120 nM, 1.2 µM, or 2.4 µM IL-8, and ratio of calcium-bound Fura2-AM to unbound was measured by fluorimeter in real time. Peak calcium flux responses were almost two-fold greater for 1.20 µM (83%+/−7.9%: percentage of maximal calcium flux) than for 120 nM IL-8 (48%+/−5.1%) ($p<0.05$). Previous reports had revealed maximal calcium 60 fluxes up to 100 nM concentrations without exploring higher concentrations. The maximal peak of calcium flux was seen at chemokine concentrations of 1.2 µM and 2.4 µM and was associated with differential rates of recovery, supporting the view that the cell could discriminate between these concentrations of the chemokine (FIG. 18). Interestingly, the recovery periods for all doses of IL-8 tested demonstrated differential levels of bound Fura2-AM, indicating different levels of intracellular calcium flux after each peak period. Thus, signal magnitude during the recovery period, as measured by calcium flux through CXCR2 and CXCR1, was greater with increasing concentrations of IL-8, indicating that neutrophils are capable of detecting and generating differential intracellular responses to concentrations of IL-8 above 100 nM. Differential levels of calcium flux to concentrations of a chemokine that are known to induce directional migratory responses and at least 10-fold greater than the estimated Kd of the recombinant chemokine receptor have been clearly demonstrated for the chemokine, SDF-1 (CXCL12) and its interaction with CXCR4 (Princen, K., et al. 2003 *Cytometry A* 51:35-45).

Figure 18A:
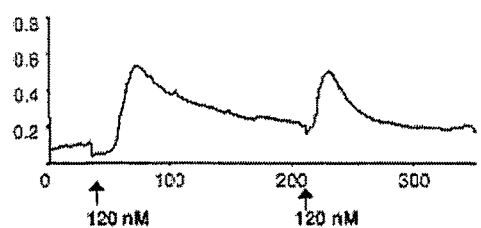
FIG. 18: Fluorescence measurement of calcium flux in neutrophils in response to various concentrations of IL-8.
Figure 18B:
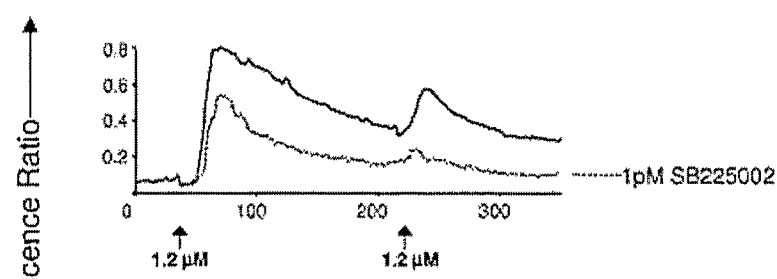
Figure 18C:
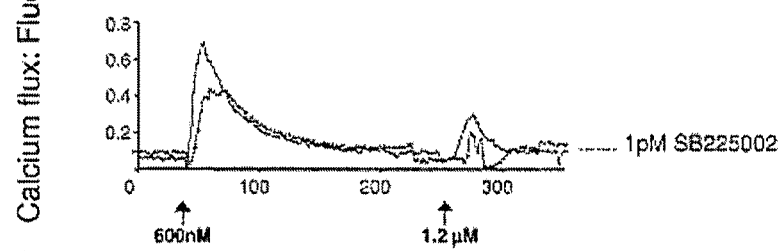
Figure 18D:
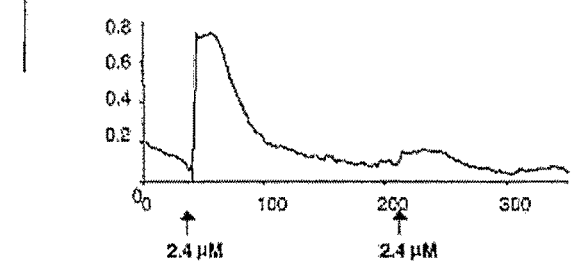

In order to determine whether signal output as measured by calcium flux could be generated from sequential low or high doses of IL-8, neutrophils were exposed to two pulses of IL-8 at low and high concentration (FIGS. 18A-D). Sequential calcium fluxes were seen in cells exposed to repeated pulses of low dose (120 nM) which had been seen to induce maximal chemoattraction (FIG. 18A) and high dose (1.2 µM) IL-8 (FIG. 18B) and a dose of 600 nM followed by a dose of 1.24 µM (FIG. 18C) which were associated with a maximal fugetactic response. Sequential calcium flux was not seen when cells were exposed to the highest dose of 2.4 µM, and this was then followed by a further high concentration of chemokine, implying that receptor saturation occurred at concentrations above 1.2 µM (FIG. 18D). These data were consistent with the finding that neutrophils were capable of directional migration and gradient sensing up to a peak concentration of 1.2 µM but underwent only chemokinetic movement in gradients with peak concentrations above this.

Given the presence of a sequential calcium flux with fugetactic concentrations of IL-8, it was examined whether CXCR2 was still detectable on the surface of the neutrophil after the first pulse of chemokine. Neutrophils were immunostained for CXCR2 following a single pulse of IL-8 at concentrations of 12 nM, 120 nM, 1.2 µM and 2.4 µM. CXCR2 was downregulated from baseline expression levels immediately after chemokine exposure, with both chemoattractant and fugetactic concentrations of IL-8 with consistent 2- to 3-fold reductions in mean fluorescent intensities (data not shown) and remained 4- to 5-fold greater than MFI values for control isotype antibody staining ($p<0.01$) (data not shown). CXCR2 was clearly still detectable on the cell surface following exposure to low or high concentrations of IL-8.

In view of the effect of the ability of picomolar concentrations of the non=peptide CXCR2 antagonist SB225002 (Calbiochem, CA) to influence neutrophil directional decision-making, it was examined whether ultralow concentrations of SB225002 could reduce the level of sequential calcium flux to high concentrations of chemokine. Treatment with 1 pM SB225002 significantly reduced sequential peaks of calcium flux following stimulation with concurrent doses of IL-8 at concentrations of 1.2 µM and 1.2 µM (FIG. 18B) ($p<0.05$) or 600 nM and 1.2 µM (FIG. 18C) ($p<0.05$), as compared to calcium flux magnitudes in the absence of the receptor antagonist. The magnitude of calcium flux following SB225002 treatment in conditions shown in (FIG. 18B) and (FIG. 18C) were of similar size to those seen with sequential pulses of lower concentrations of chemokine associated with a chemoattractant response. These data validate the observed exquisite sensitivity of receptor-mediated generation of directional bias in the motile response of cells exposed to fugetactic conditions.

Chemokines, including IL-8 and SDF-1 can serve as fugetactic agents at concentrations above 100 nM. Moreover, at such concentrations IL-8 and SDF-1 are known to exist in a dimerized state. (Lowman, H. B. et al., 1997 *Protein Science* 6:598-608; Veldkamp, C. T. et al. 2005 *Protein Science* 14:1071-1081; Horcher, M. et al. 1998 *Cytokine* 10:1-12). As shown herein, high levels of chemokine also induce intracytoplasmic calcium flux in neutrophils, which is associated with the fugetactic action. Thus, a signaling paradigm can be envisioned, wherein binding of a dimeric chemokine and dimerization of the cognate receptor on the cell surface elicits a differential signal in the cell, including an increase in calcium flux, which result in the fugetactic response.

III. Further Description of the Drawings

FIG. 18: Differential Calcium Flux. Primary human neutrophils were loaded with 1.25 µM Fura2-AM and exposed to sequential pulses of chemokine 120 seconds apart (A-C) and calcium flux measured by fluorimeter. Calcium flux in neutrophils was monitored following exposure to a single pulse of chemokine at a concentration of 120 nM followed by a subsequent pulse of 120 nM (A), 1.2 µM followed by 1.2 µM (B), 600 nM followed by 1.2 µM (C) or 2.4 µM followed by 2.4 µM (D) (solid lines). Calcium flux was also monitored in neutrophils pretreated with 1 pM SB225002 prior to treatment, as in (B) and (C) (dotted lines). The results of a representative experiment of three that were performed in this way are shown. Initial and secondary pulses of chemokine (indicated by arrows along the y-axis) are shown.

Although the foregoing invention has been described in some detail by way of illustration and example for purposes of clarity and understanding, it will be apparent to those skilled in the art that certain changes and modifications can be practiced. Therefore, the description and examples should not be construed as limiting the scope of the invention, which is delineated by the appended numbered claims.

Each of the applications and patents cited in this text, as well as each document or reference cited in each of the applications and patents (including during the prosecution of each issued patent; "application cited documents"), and each of the PCT and foreign applications or patents corresponding to and/or claiming priority from any of these applications and patents, and each of the documents cited or referenced in each of the application cited documents, are hereby expressly incorporated herein by reference. More generally, documents or references are cited in this text, either in a Reference List before the claims, or in the text itself; and, each of these documents or references ("herein-cited references"), as well as each document or reference cited in each of the herein-cited references (including any manufacturer's specifications, instructions, etc.), is hereby expressly incorporated herein by reference.

REFERENCES

1. Chaffin K E and Perlmutter R M. A pertussis toxin-sensitive process controls thymocyte emigration. Eur. J. Immunol. 21: 2565-2573 (1991)
2. Craddock C F, Nakamoto B, Andrews R G, Priestley G V and Papayannopoulou T Antibodies to VLA4 integrin mobilize long-term repopulating cells and augment cytokine-induced mobilization in primates and mice. Blood 90, 4779-4788 (1997)
3. Doetsch R N and Seymour W F. Negative chemotaxis in bacteria. Life Sciences 9:1029-1037 (1970)
4. Bailey G B, Leitch G J and Day D B. Chemotaxis by *entamoeba histolytica*. J Protozool 32:341-346 (1985)
5. Tsang N, Mcnab R and Koshland D E Jr. Common mechanism for repellents and attractants in bacterial chemotaxis. Science 181:60-69 (1973)
6. Repaske D and Adler J. Change in intracellular pH of *Escherischia coli* mediates the chemotactic response to certain attractants and repellents. J Bacteriol 145:1196-1208 (1981)
7. Tisa L S and Adler J. Cytoplasmic free-Ca2+ level rises with repellents and falls with attractants in *Escherischia coli* chemotaxis. Proc Natl Aca Sci U.S.A. 92:10777-10781 (1995)
8. Taylor B L and Johnson M S. Rewiring a receptor: negative output from positive input. FEBS Lett 425:377-381 (1998)
9. Wells T N. Power C A and Proudfoot A E. Definition, function and pathophysiological significance of chemokine receptors. Trends Pharmacol Sci 19:376-380 (1998)
10. Luster A D. Chemokines—chemotactic cytokines that mediate inflammation. N Engl J Med 338:436-445 (1998)
11. Baggiolini M. Chemokines and leukocyte traffic. Nature 392:565-568 (1998)
12. Bleul C C, Fuhlbrigge R C, Casasnovas J M, Aiuiti A and Springer T A. A highly efficacious lymphocyte chemoattractant, stromal cell-derived factor 1 (SDF-1). J Exp Med 184: 1101-1109 (1996)
13. Kim C H, Pelus L M, White J R and Broxmeyer H E. Differential chemotactic behavior of developing T-cells in response to thymic chemokines. Blood. 91: 4434-4443 (1998)
14. Tashiro K, Tada H, Heilker R, Shirozu M, Nakano T and Honjo F. Signal sequence trap: cloning strategy for secreted proteins and type 1 membrane proteins. Science, 261: 600-603
15. Shirozu M, Nakano T, Inazawa J, Tashiro K, Tado H, Shinohara T and Honjo T. Structure and chromosomal localization of the human stromal cell-derived factor 1 (SDF1) gene. Genomics 28:495-500 (1995)
16. Bacon K B, Premack B A, Gardner P and Schall T J. Activation of dual T cell signaling pathways by the chemokine RANTES. Science, 269:1727-30 (1995)
17. Noble P B and Bentley K C. Locomotory characteristics of human lymphocytes undergoing negative chemotaxis to oral carcinomas. Exp Cell Res 133; 457-461 (1981)

We claim:

1. A method for increasing the migratory capacity of immune cells into a mammalian ovarian tumor exhibiting fugetactic activity on said immune cells due to CXCL12 secretion, wherein said immune cells comprise tumor antigen-specific T-cells, which method comprises:
    a) selecting a mammal having said tumor which secretes a fugetactic effective amount of CXCL12 around said tumor wherein said concentration of CXCL12 is greater than 100 nM;
    b) contacting said T-cells with an anti-fugetactic concentration of 1,1'-[1,4-phenylenebis-(methylene)]bis[1,4,8,11-tetraazacyclotetradecane] of from 0.08 μg/mL up to 5 μg/mL wherein said T-cells are now capable of increasing their migration into said tumor through the fugetactic activity of said tumor.

2. The method of claim 1, wherein said method further comprises administering anti-cancer therapy to the said patient.

3. The method of claim 2, wherein said anti-cancer therapy is a chemotherapeutic agent selected from the group consisting of paclitaxel, cisplatin, and doxorubicin.

4. The method of claim 3, wherein the chemotherapeutic agent is paclitaxel.

5. The method of claim 1, wherein the anti-fugetactic agent is in a sustained release formulation.

6. The method of claim 1, wherein the mammal is a human.

* * * * *

UNITED STATES PATENT AND TRADEMARK OFFICE
CERTIFICATE OF CORRECTION

PATENT NO. : 9,789,171 B2
APPLICATION NO. : 11/667410
DATED : October 17, 2017
INVENTOR(S) : Poznansky et al.

Page 1 of 1

It is certified that error appears in the above-identified patent and that said Letters Patent is hereby corrected as shown below:

On the Title Page

Item (75) Inventors: Please correct "Natalia Papeta, Brookline, MA (US)" to read -- Natalia Papeta, New York, NY (US) --

Signed and Sealed this
Seventh Day of August, 2018

Andrei Iancu
*Director of the United States Patent and Trademark Office*